(12) United States Patent
Hu et al.

(10) Patent No.: US 11,608,497 B2
(45) Date of Patent: Mar. 21, 2023

(54) METHODS FOR CELL LABEL CLASSIFICATION

(71) Applicant: Becton, Dickinson and Company, Franklin Lakes, NJ (US)

(72) Inventors: Jing Hu, Menlo Park, CA (US); Christina Fan, Menlo Park, CA (US); David Rosenfeld, Menlo Park, CA (US); Jue Fan, Menlo Park, CA (US); Elisabeth Marie Walczak, Menlo Park, CA (US)

(73) Assignee: Becton, Dickinson And Company, Franklin Lakes, NJ (US)

( * ) Notice: Subject to any disclaimer, the term of this patent is extended or adjusted under 35 U.S.C. 154(b) by 684 days.

(21) Appl. No.: 15/806,174

(22) Filed: Nov. 7, 2017

(65) Prior Publication Data
US 2018/0127744 A1    May 10, 2018

Related U.S. Application Data

(60) Provisional application No. 62/445,546, filed on Jan. 12, 2017, provisional application No. 62/419,194, filed on Nov. 8, 2016.

(51) Int. Cl.
  *C12N 15/10*        (2006.01)
  *G16B 45/00*        (2019.01)
  *C12Q 1/6869*       (2018.01)
  *G16B 20/00*        (2019.01)

(52) U.S. Cl.
  CPC ....... *C12N 15/1065* (2013.01); *C12Q 1/6869* (2013.01); *G16B 20/00* (2019.02); *G16B 45/00* (2019.02); *C12Q 2525/161* (2013.01); *C12Q 2535/122* (2013.01)

(58) Field of Classification Search
  None
  See application file for complete search history.

(56) References Cited

U.S. PATENT DOCUMENTS

| | | |
|---|---|---|
| 4,510,244 A | 4/1985 | Parks et al. |
| 4,725,536 A | 2/1988 | Fritsch et al. |
| 5,124,246 A | 6/1992 | Urdea et al. |
| 5,149,625 A | 9/1992 | Church et al. |
| 5,200,314 A | 4/1993 | Urdea |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,114,149 A | 9/2000 | Fry et al. |
| 6,117,631 A | 9/2000 | Nilsen |
| 6,124,092 A | 9/2000 | O'neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,235,475 B1 | 5/2001 | Brenner et al. |

(Continued)

FOREIGN PATENT DOCUMENTS

| | | |
|---|---|---|
| CN | 102576020 | 7/2012 |
| CN | 105492627 | 4/2016 |

(Continued)

OTHER PUBLICATIONS

Macosko et al. Cell, vol. 161, Issue 5, 1202-1214, 2015.*
D'haeseleer, Dec. 2005, How does gene expression clustering work?, Nature Biotechnology, pp. 1499-1501.
Sorlie et al., Sep. 11, 2001, Gene expression patterns of breast carcinomas distinguish tumor subclasses with clinical implications, Proceedings National Academy of Sciences PNAS, 98(19):10869-10874.
International Search Report and Written Opinion dated Feb. 22, 2018 in PCT/US2017/060451.
International Search Report and Written Opinion dated Jan. 18, 2018 in PCT/US2017/060447.

(Continued)

*Primary Examiner* — Michael L Borin
(74) *Attorney, Agent, or Firm* — Knobbe, Martens, Olson & Bear, LLP

(57) ABSTRACT

Disclosed herein are methods and systems for classifying cell labels, for example identifying a signal cell label. In some embodiments, the method comprises: obtaining sequencing data of barcoded targets created using targets in cells barcoded using barcodes, wherein a barcode comprises a cell label and a molecular label. After ranking the cell labels, a minimum of a second derivative plot of a cumulative sum plot can be determined. Using the methods, a cell label can be classified as a signal cell label or a noise cell label based on the number of molecular labels with distinct sequences associated with the cell label and a cell label threshold.

24 Claims, 20 Drawing Sheets

(56) References Cited

U.S. PATENT DOCUMENTS

| | | |
|---|---|---|
| 6,268,152 B1 | 7/2001 | Fodor et al. |
| 6,284,460 B1 | 9/2001 | Fodor et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,489,114 B2 | 12/2002 | Laayoun et al. |
| 6,492,121 B2 | 12/2002 | Kurane et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,849,404 B2 | 2/2005 | Park et al. |
| 6,852,488 B2 | 2/2005 | Fodor et al. |
| 6,858,412 B2 | 2/2005 | Willis et al. |
| 7,155,050 B1 | 12/2006 | Sloge |
| 7,393,665 B2 | 7/2008 | Brenner |
| 7,424,368 B2 | 9/2008 | Huang et al. |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,822,555 B2 | 10/2010 | Huang et al. |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,148,068 B2 | 4/2012 | Brenner |
| 8,168,385 B2 | 5/2012 | Brenner |
| 8,241,850 B2 | 8/2012 | Brenner |
| 8,298,767 B2 | 10/2012 | Brenner et al. |
| 8,318,433 B2 | 11/2012 | Brenner |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet |
| 8,679,756 B1 | 3/2014 | Brenner et al. |
| 8,685,678 B2 | 4/2014 | Casbon et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,358 B2 | 9/2014 | Fodor et al. |
| 8,841,071 B2 | 9/2014 | Link |
| 8,856,410 B2 | 10/2014 | Park |
| 9,150,852 B2 | 10/2015 | Samuels et al. |
| 9,175,303 B2 | 11/2015 | Molinaro |
| 9,228,229 B2 | 1/2016 | Olson et al. |
| 9,290,808 B2 | 3/2016 | Fodor et al. |
| 9,290,809 B2 | 3/2016 | Fodor et al. |
| 9,315,857 B2 | 4/2016 | Fu et al. |
| 9,567,645 B2 | 2/2017 | Fan et al. |
| 9,567,646 B2 | 2/2017 | Fan et al. |
| 9,582,877 B2 | 2/2017 | Fu et al. |
| 9,598,736 B2 | 3/2017 | Fan et al. |
| 9,637,799 B2 | 5/2017 | Fan et al. |
| 9,708,657 B2 | 7/2017 | Asbury et al. |
| 9,708,659 B2 | 7/2017 | Fodor et al. |
| 9,787,810 B1 | 8/2017 | Fodor et al. |
| 9,951,386 B2 | 4/2018 | Hindson et al. |
| 2002/0072058 A1 | 6/2002 | Voelker et al. |
| 2002/0168665 A1 | 11/2002 | Okawa |
| 2003/0003490 A1 | 1/2003 | Fan et al. |
| 2003/0049616 A1 | 3/2003 | Brenner et al. |
| 2003/0082818 A1 | 5/2003 | Bahnson et al. |
| 2003/0104436 A1 | 6/2003 | Morris et al. |
| 2003/0175908 A1 | 9/2003 | Linnarson |
| 2003/0186251 A1 | 10/2003 | Dunn et al. |
| 2003/0207300 A1 | 11/2003 | Matray et al. |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0259118 A1 | 12/2004 | Macevicz |
| 2005/0019776 A1 | 1/2005 | Callow et al. |
| 2005/0170373 A1 | 8/2005 | Monforte |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0041385 A1 | 2/2006 | Bauer |
| 2006/0073506 A1 | 4/2006 | Christians et al. |
| 2006/0078941 A1 | 4/2006 | Santin |
| 2006/0141493 A1 | 6/2006 | West et al. |
| 2006/0211030 A1 | 9/2006 | Brenner |
| 2006/0211036 A1 | 9/2006 | Chou |
| 2006/0263709 A1 | 11/2006 | Matsumura et al. |
| 2006/0263789 A1 | 11/2006 | Kincaid |
| 2007/0020640 A1 | 1/2007 | Mccloskey et al. |
| 2007/0065823 A1 | 3/2007 | Dressman et al. |
| 2007/0117134 A1 | 5/2007 | Kou |
| 2007/0172873 A1 | 7/2007 | Brenner et al. |
| 2007/0178478 A1 | 8/2007 | Dhallan et al. |
| 2008/0010304 A1 | 1/2008 | Vempala |
| 2008/0070303 A1 | 3/2008 | West et al. |
| 2008/0194414 A1 | 8/2008 | Albert et al. |
| 2008/0261204 A1 | 10/2008 | Lexow |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0061513 A1 | 3/2009 | Andersson et al. |
| 2009/0105959 A1 | 4/2009 | Braverman et al. |
| 2009/0137407 A1 | 5/2009 | Church et al. |
| 2009/0170075 A1 | 7/2009 | Petrovics |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0298709 A1 | 12/2009 | Ma |
| 2010/0069250 A1 | 3/2010 | White, III |
| 2010/0105049 A1 | 4/2010 | Ehrich et al. |
| 2010/0105886 A1 | 4/2010 | Woudenberg et al. |
| 2010/0120630 A1 | 5/2010 | Huang et al. |
| 2010/0145893 A1 | 6/2010 | Semizarov |
| 2010/0255471 A1 | 10/2010 | Clarke |
| 2010/0291666 A1 | 11/2010 | Collier et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0294689 A1 | 12/2011 | Namsaraev |
| 2012/0010091 A1 | 1/2012 | Linnarson |
| 2012/0040843 A1 | 2/2012 | Ducree et al. |
| 2012/0045844 A1 | 2/2012 | Rothberg et al. |
| 2012/0065081 A1 | 3/2012 | Chee |
| 2012/0071331 A1 | 3/2012 | Casbon |
| 2012/0156675 A1 | 6/2012 | Lueerssen et al. |
| 2012/0163681 A1 | 6/2012 | Lohse |
| 2012/0173159 A1 | 7/2012 | Davey et al. |
| 2012/0190020 A1 | 7/2012 | Oliphant et al. |
| 2012/0220022 A1 | 8/2012 | Ehrlich et al. |
| 2012/0220494 A1 | 8/2012 | Samuels |
| 2012/0316074 A1 | 12/2012 | Saxonov |

(56) References Cited

U.S. PATENT DOCUMENTS

| | | |
|---|---|---|
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1 | 5/2013 | Fu |
| 2013/0190206 A1 | 7/2013 | Leonard |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0143186 A1 | 5/2014 | Fan |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0206547 A1 | 7/2014 | Wang |
| 2014/0216128 A1 | 8/2014 | Neat |
| 2014/0227684 A1 | 8/2014 | Hindson et al. |
| 2014/0227705 A1 | 8/2014 | Vogelstein et al. |
| 2014/0228255 A1 | 8/2014 | Hindson et al. |
| 2014/0235506 A1 | 8/2014 | Hindson et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0344013 A1 | 11/2014 | Karty |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0066385 A1 | 3/2015 | Schnall-levin et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0225778 A1 | 8/2015 | Hindson et al. |
| 2015/0298091 A1 | 10/2015 | Weitz |
| 2015/0299784 A1 | 10/2015 | Fan |
| 2015/0307874 A1 | 10/2015 | Jaitin |
| 2015/0376609 A1 | 12/2015 | Hindson et al. |
| 2016/0026758 A1 | 1/2016 | Jabara et al. |
| 2016/0046986 A1 | 2/2016 | Eltoukhy et al. |
| 2016/0244828 A1 | 8/2016 | Mason |
| 2016/0257993 A1 | 9/2016 | Fu et al. |
| 2016/0289669 A1 | 10/2016 | Fan et al. |
| 2016/0289740 A1 | 10/2016 | Fu et al. |
| 2016/0312276 A1 | 10/2016 | Fu et al. |
| 2016/0320720 A1 | 11/2016 | Fan et al. |
| 2016/0326584 A1 | 11/2016 | Fodor et al. |
| 2016/0376583 A1 | 12/2016 | Fodor et al. |
| 2016/0376648 A1 | 12/2016 | Fodor et al. |
| 2017/0073730 A1 | 3/2017 | Betts et al. |
| 2017/0154421 A1 | 6/2017 | Fu et al. |
| 2017/0204406 A1 | 7/2017 | Kato et al. |
| 2017/0247689 A1 | 8/2017 | Brown |
| 2017/0344866 A1 | 11/2017 | Fan et al. |
| 2018/0137242 A1 | 5/2018 | Fan et al. |
| 2018/0276332 A1 | 9/2018 | Fan et al. |
| 2019/0095578 A1 | 3/2019 | Shum |
| 2019/0218276 A1 | 7/2019 | Regev |

FOREIGN PATENT DOCUMENTS

| | | |
|---|---|---|
| DE | 102008025656 | 12/2009 |
| EP | 0 799 897 | 10/1997 |
| EP | 1 473 080 | 11/2004 |
| EP | 1 647 600 | 4/2006 |
| EP | 1 845 160 | 10/2007 |
| EP | 2 623 613 | 8/2013 |
| EP | 2 805 769 | 11/2014 |
| WO | WO 89/01050 | 2/1989 |
| WO | WO 97/10365 | 3/1997 |
| WO | WO 99/15702 | 4/1999 |
| WO | WO 99/28505 | 6/1999 |
| WO | WO 00/58516 | 10/2000 |
| WO | WO 02/056014 | 7/2002 |
| WO | WO 02/070684 | 9/2002 |
| WO | WO 04/017374 | 2/2004 |
| WO | WO 05/042759 | 5/2005 |
| WO | WO 05/071110 | 8/2005 |
| WO | WO 05/080604 | 9/2005 |
| WO | WO 05/111242 | 11/2005 |
| WO | WO 06/071776 | 7/2006 |
| WO | WO 06/102264 | 9/2006 |
| WO | WO 07/087310 | 8/2007 |
| WO | WO 07/087312 | 8/2007 |
| WO | WO 08/096318 | 8/2008 |
| WO | WO 09/148560 | 12/2009 |
| WO | WO 09/152928 | 12/2009 |
| WO | WO 10/117620 | 10/2010 |
| WO | WO 11/123246 | 10/2011 |
| WO | WO 11/143659 | 11/2011 |
| WO | WO 11/155833 | 12/2011 |
| WO | WO 12/038839 | 3/2012 |
| WO | WO 12/042374 | 4/2012 |
| WO | WO 12/047297 | 4/2012 |
| WO | WO 12/048341 | 4/2012 |
| WO | WO 12/083225 | 6/2012 |
| WO | WO 12/108864 | 8/2012 |
| WO | WO 12/129363 | 9/2012 |
| WO | WO 12/140224 | 10/2012 |
| WO | WO 12/142213 | 10/2012 |
| WO | WO 12/148477 | 11/2012 |
| WO | WO 12/149042 | 11/2012 |
| WO | WO 12/162267 | 11/2012 |
| WO | WO 13/019075 | 2/2013 |
| WO | WO 13/117595 | 8/2013 |
| WO | WO 13/130674 | 9/2013 |
| WO | WO 13/173394 | 11/2013 |
| WO | WO 13/176767 | 11/2013 |
| WO | WO 13/177206 | 11/2013 |
| WO | WO 13/188831 | 12/2013 |
| WO | WO 13/188872 | 12/2013 |
| WO | WO 13/191775 | 12/2013 |
| WO | WO 14/015084 | 1/2014 |
| WO | WO 14/015098 | 1/2014 |
| WO | WO 14/018460 | 1/2014 |
| WO | WO 14/028537 | 2/2014 |
| WO | WO 14/071361 | 5/2014 |
| WO | WO 14/093676 | 6/2014 |
| WO | WO 14/108850 | 7/2014 |
| WO | WO 14/124336 | 8/2014 |
| WO | WO 14/124338 | 8/2014 |
| WO | WO 14/126937 | 8/2014 |
| WO | WO 14/144495 | 9/2014 |
| WO | WO 14/201273 | 12/2014 |
| WO | WO 14/210353 | 12/2014 |
| WO | WO 15/002908 | 1/2015 |
| WO | WO 15/031691 | 3/2015 |
| WO | WO 15/035087 | 3/2015 |
| WO | WO 15/044428 | 4/2015 |
| WO | WO 15/047186 | 4/2015 |
| WO | WO 15/103339 | 7/2015 |
| WO | WO 15/134787 | 9/2015 |
| WO | WO 15/177570 | 11/2015 |
| WO | WO 15/200869 | 12/2015 |
| WO | WO 16/040476 | 3/2016 |
| WO | WO 16/118915 | 7/2016 |
| WO | WO 16/149418 | 9/2016 |

(56) References Cited

FOREIGN PATENT DOCUMENTS

| WO | WO 16/162309 | 10/2016 |
|---|---|---|
| WO | WO 17/205691 | 11/2017 |
| WO | WO 18/226293 | 12/2018 |

OTHER PUBLICATIONS

Achim et al., May 2015, High-throughput spatial mapping of single-cell RNA-seq data to tissue of origin. Nature Biotechnology, 33(5):503-511.
Alkan et al., Oct. 2009, Personalized copy number and segmental duplication maps using next-generation sequencing. Nat Genet., 41(10):1061-1067.
Anderson, Feb. 11, 2014, Study describes RNA sequencing applications for molecular indexing methods, genomeweb.com, 5 pp.
Ansorge, 2009, Next-generation DNA sequencing techniques. New Biotechnology, 25(4):195-203.
Atanur et al., Jun. 2010, The genome sequence of the spontaneously hypertensive rat: Analysis and functional significance. Genome Res., 20(6):791-803.
Audic et al., 1997, The Significance of Digital Gene Expression Profiles. Genome Research, 7:986-995.
Bendall et al., May 6, 2011, Single-cell mass cytometry of differential immune and drug responses across a human hematopoietic continuum. Science, 332(6030):687-696.
Bionumbers, Aug. 21, 2010, Useful fundamental numbers in molecular biology, http://bionumbers.hms.harvard.edu/KeyNumbers/aspx, 4 pp.
Bioscribe, Feb. 5, 2015, Massively parallel sequencing technology for single-cell gene expression published (press release), 3 pp.
Blainey, May 2013, The future is now: single-cell genomics of bacteria and archaea, FEMS Microbiol Rev., 37(3):407-427.
Bogdanova et al., Jan. 2008, Normalization of full-length enriched cDNA, Molecular Biosystems, 4(3):205-212.
Bonaldo et al., Sep. 1996, Normalization and subtraction: two approaches to facilitate gene discovery. Genome Res., 6(9):791-806.
Braha et al., 2000, Simultaneous stochastic sensing of divalent metal ions. Nature Biotechnology, 17:1005-1007.
Bratke et al., Sep. 2005, Differential expression of human granzymes A, B, and K in natural killer cells and during CD8+ T cell differentiation in peripheral blood. Eur J Immunol., 35(9):2608-2616.
Brenner et al., 2000, Gene expression analysis by massively parallel signature sequencing (MPSS) on microbead arrays. Nature Biotechnology, 18:630-634.
Brenner et al., Feb. 15, 2000, In vitro cloning of complex mixtures of DNA on microbeads: physical separation of differentially expressed cDNAs. Proc Natl Acad Sci, 97(4):1665-1670.
Brisco et al., Jun. 25, 2012, Quantification of RNA integrity and its use for measurement of transcript number, Nucleic Acids Research, 40(18):e144.
Brodin et al., 2015, Challenges with using primer IDs to improve accuracy of next generation sequencing, 19(3):1-12.
Butkus, Feb. 6, 2014, Cellular research set to launch first gene expression platform using 'molecular indexing' technology, genomeweb.com, 5 pp.
Cai, Mar. 2013, Turning single cells in microarrays by super-resolution bar-coding, Brief Funct Genomics, 12(2):75-80.
Carr et al., Dec. 15, 2009, Inferring relative proportions of DNA variants from sequencing electropherograms. Bioinformatics, 25(24):3244-3250.
Casbon et al., Jul. 2011, A method for counting PCR template molecules with application to next-generation sequencing. Nucleic Acids Res., 39(12):e81.
Castellarnau et al., Jan. 2015, Stochastic particle barcoding for single-cell tracking and multiparametric analysis, Small, 11(4):489-498.
Castle et al., Apr. 16, 2010, DNA copy number, including telomeres and mitochondria, assayed using next-generation sequencing. BMC Genomics, 11:244. doi: 10.1186/1471-2164-11-244.
Chamberlain et al., Dec. 9, 1988, Deletion screening of the Duchenne muscular dystrophy locus via multiplex DNA amplification. Nucleic Acids Res., 16(23):11141-11156.
Chang et al., Aug. 2002, Detection of allelic imbalance in ascitic supernatant by digital single nucleotide polymorphism analysis. Clin Cancer Res., 8(8):2580-2585.
Chee et al., 1996, Accessing genetic information with high-density DNA arrays, Science, 274:610-614.
Chee, 1991, Enzymatic multiplex DNA sequencing. Nucleic Acids Research, 19(12): 3301-3305.
Chen et al., Apr. 9, 2015, Spatially resolved, highly multiplexed RNA profiling in single cells. Science Express, pp. 1-21.
Church et al., 1988, Multiplex DNA sequencing. Science, 240:185-188.
Costello et al., Apr. 1, 2013, Discovery and characterization of artefactual mutations in deep coverage targeted capture sequencing data due to oxidative DNA damage during sample preparation. Nucleic Acids Res, 41(6):e67.
Cox. May 2001, Bar coding objects with DNA. Analyst, 126(5):545-547.
Craig et al., Oct. 2008, Identification of genetic variants using bar-coded multiplexed sequencing. Nat Methods, 5(10):887-893.
Cusanovich et al., May 7, 2014, Multiplex single-cell profiling of chromatin accessibility by combinatorial cellular indexing. Science Express, pp. 1-9.
Daines et al., Aug. 2009, High-throughput multiplex sequencing to discover copy number variants in Drosophila. Genetics, 182(4):935-941.
Dalerba et al., 2011, Single-cell dissection of transcriptional heterogeneity in human colon tumors, Nat Biotechnol., 29(12):1120-1127 and Supplementary Material.
D'Antoni et al., May 1, 2006, Rapid quantitative analysis using a single molecule counting approach. Anal Biochem. 352(1):97-109.
Daser et al., 2006, Interrogation of genomes by molecular copy-number counting (MCC). Nature Methods, 3(6):447-453.
De Saizieu et al., 1998, Bacterial transcript imaging by hybridization of total RNA to oligonucleotide arrays. Nature Biotechnology, 16:45-48.
Dirks et al., Oct. 26, 2004, Triggered amplification by hybridization chain reaction., Proc Natl Acad Sci U S A, 101(43), 15275-15278.
Fan et al., Feb. 6, 2015, Combinatorial labeling of single cells for gene expression cytometry. Science, 347(6222): 1258367-8.
Fan et al., 2000, Parallel Genotyping of Human SNPs Using Generic High-density Oligonucleotide Tag Arrays. Genome Research, 10:853-860.
Fan et al., 2009, Microfluidic digital PCR enables rapid prenatal diagnosis of fetal aneuploidy. Am Obstet Gynecol. 200:543.e1-543.e7.
Fan et al., Jul. 19, 2012, Non-invasive prenatal measurement of the fetal genome. Nature, 487(7407):320-324.
Fan, Nov. 2010, Molecular counting: from noninvasive prenatal diagnostics to whole-genome haplotyping, doctoral dissertation, Stanford University, 185 pp.
Feldhaus et al., Jan. 15, 2000, Oligonucleotide-conjugated beads for transdominant genetic experiments, Nucleic Acids Res., 28(2):534-543.
Fox-Walsh et al., Oct. 2011, A multiplex RNA-seq strategy to profile poly(A+) RNA: application to analysis of transcription response and 3' end formation., Genomics, 98(4),266-271.
Fu et al., Mar. 18, 2014, Digital encoding of cellular mRNAs enabling precise and absolute gene expression measurement by single-molecule counting. Anal Chemn., 86(6):2867-2870.
Fu et al., May 31, 2011, Counting individual DNA molecules by the stochastic attachment of diverse labels. Proc Natl Acad Sci, 108(22):9026-9031.
Gerry et al., 1999, Universal DNA microarray method for multiplex detection of low abundance point mutations. Journal of Molecular Biology, 292(2): 251-262.
Gillespie, 1977, Exact stochastic simulation of coupled chemical reactions. The Journal of Physical Chemistry, 81(25):2340-2361.

(56) References Cited

OTHER PUBLICATIONS

Gong et al., 2010, Massively parallel detection of gene expression in single cells using subnanolitre wells, Lab Chip, 10:2334-2337.
Grant et al., Nov. 15, 2002, SNP genotyping on a genome-wide amplified DOP-PCR template. Nucleic Acids Res, 30(22):e125.
Gunderson et al., May 2004, Decoding randomly ordered DNA arrays. Genome Res. 14(5):870-877.
Gundry et al., Jan. 3, 2012, Direct mutation analysis by high-throughput sequencing: from germline to low-abundant, somatic variants. Mutat Res. 729(1-2):1-15.
Gundry et al., Mar. 2012, Direct, genome-wide assessment of DNA mutations in single cells. Nucleic Acids Res., 40(5):2032-40.
Hacia et al., 1999, Determination of ancestral alleles for human single-nucleotide polymorphisms using high-density oligonucleotide arrays. Nature Genetics, 22:164-167.
Haff, 1994, Improved quantitative PCR using nested primers, PCR Methods and Applications, 3:332-337.
Hamady et al., Mar. 2008, Error-correcting barcoded primers for pyrosequencing hundreds of samples in multiplex. Nat Methods, 5(3):235-237.
Harrington et al., 2009, Cross-sectional characterization of HIV-1 env compartmentalization in cerebrospinal fluid over the full disease course, AIDS, 23(8) 907-915.
Hashimshony et al., Sep. 27, 2012, CEL-Seq: single-cell RNA-Seq by multiplexed linear amplification Cell Rep. 2(3):666-673.
Hensel et al., Jul. 21, 1995, Simultaneous identification of bacterial virulence genes by negative selection. Science. 269(5222):400-403.
Hiatt et al., Feb. 2010, Parallel, tag-directed assembly of locally derived short sequence reads. Nat Methods, 7(2):119-122.
Hiatt et al., May 2013, Single molecule molecular inversion probes for targeted, high-accuracy detection of low-frequency variation. Genome Res., 23(5):843-854.
Hollas et al., 2003, A stochastic approach to count RNA molecules using DNA sequencing methods. Lecture Notes in Computer Science, 2812:55-62.
Hug et al., 2003, Measure of the number of molecular of a single mRNA species in a complex mRNA preparation, Journal of Theoretical Biology, 221:615-624.
Ingolia et al., Apr. 10, 2009, Genome-wide analysis in vivo of translation with nucleotide resolution using ribosome profiling. Science, 324(5924):218-223.
Islam et al., 2011, Characterization of the single-cell transcriptional landscape by highly multiplex RNA-seq. Genome Research, 21:1160-1167.
Islam et al., 2014, Quantitative single-cell RNA-seq with unique molecular identifiers, Nature Methods, 11(2):163-168.
Jabara et al., Dec. 3, 2011, Accurate sampling and deep sequencing of the HIV-1 protease gene using a Primer ID, PNAS, 108(50):20166-20171.
Jabara, Apr. 23, 2010, Capturing the cloud: High throughput sequencing of multiple individual genomes from a retroviral population. Biology Lunch Bunch Series, Training Initiatives in Biomedical & Biological Sciences of the University of North Carolina at Chapel Hill.
Junker et al., May 21, 2015, Single-cell transcriptomics enters the age of mass production, Molecular Cell, 58:563-564.
Kanagawa, 2003, Bias and artifacts in multitemplate polymerase chain reactions (PCR), Journal of Bioscience and Bioengineering, 96(4):317-323.
Kebschull et al., Jul. 17, 2015, Sources of PCR-induced distortions in high-throughput sequencing data sets, Nucleic Acids Research, 15 pp.
Keys et al., Jun. 2015, Primer ID informs next-generation sequencing platforms and reveals preexisting drug resistance mutations in the HIV-1 reverse transcriptase coding domain, AIDS Research and Human Retroviruses, 31(6):658-668.
Kim et al., Jun. 8, 2007, Polony multiplex analysis of gene expression (PMAGE) in mouse hypertrophic cardiomyopathy, Science, 316(5830):1481-1484.
Kinde et al., Jun. 7, 2011, Detection and quantification of rare mutations with massively parallel sequencing, Proc. Natl Acad Sci, 108(23):9530-0535.
Kivioja et al., Jan. 2012, Counting absolute numbers of molecules using unique molecular identifiers. Nature Methods, 9(1):72-76.
Klein et al., May 21, 2015, Droplet barcoding for single-cell transcriptomics applied to embryonic stem cells, Cell, 161:1187-1201.
Koboldt et al., Sep. 1, 2009, VarScan: variant detection in massively parallel sequencing of individual and pooled samples. Bioinformatics. 25(17):2283-2285.
Kolodziejczyk et al., May 21, 2015, The technology and biology of single-cell RNA sequencing, Molecular Cell, 58:610-620.
Konig et al., Jul. 2010, iCLIP reveals the function of hnRNAP particles in splicing at individual nucleotide resolution, Nature Structural & Molecular Biology, 17(7):909-916.
Kotake et al., 1996, A simple nested RT-PCR method for quantitation of the relative amounts of multiple cytokine mRNAs in small tissue samples, Journal of Immunological Methods, 199:193-203.
Kurimoto et al., Mar. 17, 2006, An improved single-cell cDNA amplification method for efficient high-density oligonucleotide microarray analysis, Nucleic Acids Res., 34(5):e42.
Lambie et al., Nov. 20, 2013, Improved workflows for high throughput library preparation using the transposome-based nextera system, BMC Biotechnology, 13(1):104.
Larson et al., Nov. 2009, A single molecule view of gene expression. Trends Cell Biol. 19(11):630-637.
Leamon et al., Nov. 2003, A massively parallel Pico TiterPlate based platform for discrete picoliter-scale polymerase chain reactions, Electrophoresis, 24(21):3769-3777.
Lee et al., 2010, Large-scale arrays of picolitre chambers for single-cell analysis of large cell populations, Lab Chip, 10:2952-2958.
Lee et al., Mar. 21, 2014, Highly multiplexed subcellular RNA sequencing in situ. Science. 343(6177): 1360-1363.
Liu et al., Single-cell transcriptome sequencing: recent advances and remaining challenges, F1000Research 2016, 5(F1000 Faculty Rev):182, 9 pp.
Lizardi et al., Jul. 1998, Mutation detection and single-molecule counting using isothermal rolling-circle amplification. Nat Genet. 19(3):225-32.
Lockhart et al., 1996, Expression monitoring by hybridization to high-density oligonucleotide arrays. Nature Biotechnology, 14:1675-1680.
Lovatt et al., Feb. 2014, Transcriptome in vivo analysis (TIVA) of spatially defined single cells in live tissue. Nat Methods. 11(2):190-196.
Lucito et al., 1996, Representational Oligonucleotide Microarray Analysis: A High-Resolution Method to Detect Genome Copy numner Variation. Genome Research, 13: 2291-2305.
Maamar et al., 2007, Noise in Gene Expression Determines Cell Fate in Bacillus subtilis. Science, 317:526-529.
Macaulay et al., 2015, G&T-seq: parallel sequencing of single-cell genomes and transcriptomes. Nature Methods, pp. 1-7.
Macosko et al., 2015, Highly parallel genome-wide expression profiling of individual cells using nanoliter droplets, Cell 161:1202-1214 (and supplemental information).
Makrigiorgos et al., Sep. 2002, A PCR-Based amplification method retaining quantities difference between two complex genomes. Nature Biotech, 20(9):936-939.
Marcus et al., 2006, Microfluidic single-cell mRNA isolation and analysis, Ana. Chem. 78:3084-3089.
Margulies et al., Sep. 15, 2005 Genome sequencing in microfabricated high-density picolitre reactors, Nature, 437:376-380.
Martinez et al., Jul. 2012, A microfluidic approach to encapsulate living cells in uniform alginate hydrogel microparticles, Macromol. Biosci, 12(7):946-951.
McCloskey et al., Dec. 2007, Encoding PCR products with batch-stamps and barcodes. Biochem Genet. 45(11-12):761-767.
Medvedev et al., Nov. 2010, Detecting copy number variation with mated short reads. Genome Res. 20(11):1613-1622.

(56) References Cited

OTHER PUBLICATIONS

Mei et al., Mar. 22, 2010, Identification of recurrent regions of Copy-Number Variants across multiple individuals. BMC Bioinformatics. 11:147.

Merriam-Webster, definition of associate,: http://www.merriam-webster.com/dictionary/associate, accessed Apr. 5, 2016.

Miller et al., 2006, Directed evolution by in vitro compartmentalization, Nature Methods, 3:561-570.

Miner et al., 2004, Molecular barcodes detect redundancy and contamination in hairpin-bisulfite PCR, Nucleic Acids Research, 32(17):e135.

Mortazavi et al., 2008, Mapping and quantifying mammalian transcriptomes by RNA-Seq. Nat. Methods. 5:621-628.

Nadai et al., 2008, Protocol for nearly full-length sequencing of HIV-1 RNA from plasma, PLoS ONE, 3(1):e1420.

Nagai et al., 2001, Development of a microchamber array for picoleter PCR, Anal. Chem., 73:1043-1047.

Navin et al., 2015, The first five years of single-cell cancer genomics and beyond, Genome Research, 25(10):1499-1507.

Newell et al., Jan. 27, 2012, Cytometry by time-of-flight shows combinatorial cytokine expression and virus-specific cell niches within a continuum of CD8+ T cell phenotypes. Immunity. 36(1):142-152.

Novak et al., Jan. 20, 2011, Single-cell multiplex gene detection and sequencing with microfluidically generated agarose emulsions, Angew Chern Int Ed Engl., 50(2):390-395.

Ogino et al., Nov. 2002, Quantification of PCR bias caused by a single nucleotide polymorphism in SMN gene dosage analysis. J Mol Diagn. 4(4):185-190.

Parameswaran et al., 2007, A pyrosequencing-tailored nucleotide barcode design unveils opportunities for large-scale sample multiplexing. Nucleic Acids Res. 35(19):e130.

Park et al., May 2010, Discovery of common Asian copy number variants using integrated high-resolution array CGH and massively parallel DNA sequencing. Nat Genet. 42(5):400-405.

Patanjali et al., Mar. 1991, Construction of a uniform-abundance (normalized) CNDA library, Proceedings of the National Academy of Sciences, 88(5):1943-1947.

Peng et al., Mar. 11, 2016, Reducing amplification artifacts in high multiplex amplicon sequencing by using molecular barcodes, BMC Genomics, retrieved from the internet: url:http://bmcgenomics.biomedcentral.com/articles/0.1186/s12864-015-1806-8, 14 pp.

Pfaffl et al., Mar. 2004, Determination of stable housekeeping genes, differentially regulated target genes and sample integrity: BestKeeper—Excel-based tool using pair-wise correlations, Biotechnology Letters, 26(6):505-515.

Picelli et al., Jul. 30, 2014, Tn5 transposase and tagmentation procedures for massively scaled sequencing projects, Genome Research 24(12):2033-2040.

Pihlak et al., 2008, Rapid genome sequencing with short universal tiling probes. Nature Biotechnology, 26:676-684.

Pinkel et al., 2005, Comparative Genomic Hybridization. Annual Review of Genomics and Human Genetics, 6:331-354.

Pleasance et al., Jan. 14, 2010, A small-cell lung cancer genome with complex signatures of tobacco exposure. Nature. 463(7278):184-190.

Plessy et al., Feb. 2013, Population transcriptomics with single-cell resolution: a new field made possible by microfluidics: a technology for high throughput transcript counting and data-driven definition of cell types, Bioessays, 35(2):131-140.

Qiu et al., Oct. 2003, DNA sequence-based "bar codes" for tracking the origins of expressed sequence tags from a maize cDNA library constructed using multiple mRNA sources. Plant Physiol. 133(2):475-481.

Rajeevan et al., Oct. 2003, Global amplification of sense RNA: a novel method to replicate and archive mRNA for gene expression analysis, Genomics, 82(4):491-497.

Roche Diagnostics GmbH, 2006, Genome Sequencer 20 System: First to the Finish (product brochure), 40 pp.

Sasagawa et al., 2013, Quartz-Seq: a highly reproducible and sensitive single-cell RNA sequencing method, reveals non-genetic gene-expression heterogeneity. Genome Biology, 14:R31.

Sasuga et al., Dec. 2008, Single-cell chemical lysis method for analyses of intracellular molecules using an array of picoliter-scale microwells, Anal Chern, 80(23):9141-9149.

Satija et al., May 2015, Spatial reconstruction of single-cell gene expression data. Nature Biotechnology, 33(5):495-508.

Schmitt et al., Sep. 4, 2012, Detection of ultra-rare mutations by next-generation sequencing. Proc Natl Acad Sci U S A. 109(36):14508-14513.

Sebat et al., 2004, Large-Scale Copy Number Polymorphism in the Human Genome. Science, 305:525-528.

Shalek et al., Jun. 13, 2013, Single-cell transcriptomics reveals bimodality in expression and splicing in immune cells. Nature. 498(7453):236-240.

Shiroguchi et al., Jan. 24, 2012, Digital RNA sequencing minimizes sequence-dependent bias and amplification noise with optimized single-molecule barcodes. Proc Natl Acad Sci U S A. 109(4):1347-1352.

Shoemaker et al., 1996, Quantitative phenotypic analysis of yeast deletion mutants using a highly parallel molecular bar-coding strategy. Nature Genetics, 14:450-456.

Simpson et al., Feb. 15, 2010, Copy number variant detection in inbred strains from short read sequence data. Bioinformatics. 26(4):565-567.

Smith et al., 2010, Highly-multiplexed barcode sequencing: an efficient method for parallel analysis of pooled samples. Nucleic Acids Research, 38(13):e142.

Soumillon et al., Mar. 5, 2014, Characterization of directed differentiation by high-throughput single-cell RNA-Seq, bioRxiv preprint, http://biorxiv.org/content/early/2014/03/05/003236.full.pdf, 13 pp.

Speicher et al., Oct. 2005, The new cytogenetics: blurring the boundaries with molecular biology, Nature Reviews Genetics, 6(10):782-792.

Stratagene 1998 Catalog, Gene Characterization Kits, p. 39.

Takahashi et al., Mar. 2006, Novel technique of quantitative nested real-time PCR assay for *mycobacterium* tuberculosis DNA, Journal of Clinical Microbiology, 44(3):1029-1039.

Tan et al., Apr. 2013, Genome-wide comparison of DNA hydroxymethylation in mouse embryonic stem cells and neural progenitor cells by a new comparative hMeDIP-seq method. Nucleic Acids Res. 41(7):e84.

Taudien et al., Apr. 19, 2010, Haplotyping and copy number estimation of the highly polymorphic human beta-defensin locus on 8p23 by 454 amplicon sequencing. BMC Genomics. 11:252.

The Tibbs Times, UNC bioscience newsletter, Apr. 2010, 17 pp.

Tomaz et al., Aug. 2010, Differential methylation as a cause of allele dropout at the imprinted GNAS locus. Genet Test Mol Biomarkers. 14(4):455-460.

Treutlein et al., May 15, 2014, Reconstructing lineage hierarchies of the distal lung epithelium using single-cell RNA-seq. Nature. 509(7500):371-375.

Vandesompele et al., Jun. 18, 2002, Accurate normalization of real-time quantitative RT-PCR data by geometric averaging of multiple internal control genes, Genome Biology, 3(7).

Velculescu et al., 1995, Serial Analysis of Gene Expression. Science, 270:484-487.

Velculescu et al., 1997, Characterization of the Yeast Transcriptome. Cell, 88:243-251.

Vogelstein et al., 1999, Digital PCR. Proc. Natl. Acad. Sci., 96(16):9236-9241.

Walker et al., Jan. 1, 1992, Isothermal in vitro amplification of DNA by a restriction enzyme/DNA polymerase system. Proc Natl Acad Sci U S A., 89(1):392-396.

Walsh et al., Jul. 13, 2010, Detection of inherited mutations for breast and ovarian cancer using genomic capture and massively parallel sequencing. Proc Natl Acad Sci U S A. 107(28):12629-12633.

Wang et al., 2009, RNA-Seq: a revolutionary tool for transcriptomics. Nature Reviews Genetics, 10:57-63.

Wang et al., May 21, 2015, Advances and applications of single-cell sequencing technologies, Molecular Cell, 58(4):598-609.

(56) References Cited

OTHER PUBLICATIONS

Wang et al., Oct. 2010, iCLIP predicts the dual splicing effects of TIA-RNA interactions, PLoS Biol, 8(10):e1000530.
Warren et al., Nov. 21, 2006, Transcription factor profiling in individual hematopoietic progenitors by digital RT-PCR, PNAS, 103(47):17807-17812.
Weber et al., Sep. 15, 2003, A real-time polymerase chain reaction assay for quantification of allele ratios and correction of amplification bias. Anal Biochem. 320(2):252-258.
Weiner et al., Apr. 2008, Kits and their unique role in molecular biology: a brief retrospective, BioTechniques, 44:701-704.
White et al., Aug. 23, 2011, High-throughput microfluidic single-cell RT-qPCR, PNAS, 108(34):13999-14004.
Wittes et al., 1999, Searching for Evidence of Altered Gene Expression: a Comment on Statistical Analysis of Microarray Data. Journal of the National Cancer Institute, 91(5):400-401.
Wodicka et al., 1997, Genome-wide expression monitoring in *Saccharomyces cerevisiae*. Nature Biotechnology, 15:1359-1367.
Wojdacz et al., May 16, 2009, Primer design versus PCR bias in methylation independent PCR amplifications. Epigenetics. 4(4):231-234.
Wood et al., Aug. 2010, Using next-generation sequencing for high resolution multiplex analysis of copy number variation from nanogram quantities of DNA from formalin-fixed paraffin-embedded specimens. Nucleic Acids Res. 38(14):e151.
Wu et al., Jan. 2014, Quantitative assessment of single-cell RNA-sequencing methods. Nat Methods. 11(1):41-46.
Yandell et al., Sep. 2011, A probabilistic disease-gene finder for personal genomes. Genome Res. 21(9):1529-1542.
Ye et al., 2001, Fluorescent microsphere-based readout technology for multiplexed human single nucleotide polymorphism analysis and bacterial identification. Human Mutation, 17(4):305-316.
Yoon et al., Sep. 2009, Sensitive and accurate detection of copy number variants using read depth of coverage. Genome Res. 19(9):1586-1592.
Zhang et al., Jun. 19, 2012, DNA-based hybridization chain reaction for amplified bioelectronic signal and ultrasensitive detection of proteins. Anal Chem., 84(12),5392-5399.
Zhang et al., Mar. 20, 2011, The impact of next-generation sequencing on genomics. J Genet Genomics. 38(3):95-109.
Zhao et al., 2005, Homozygous Deletions and Chromosome Amplifications in Human Lung Carcinomas Revealed by Single Nucleotide Polymorphism Array Analysis. Cancer Research, 65:5561-5570.
Zheng et al., Feb. 2016, Haplotyping germline and cancer genomes with high-throughput linked-read sequencing, Nature Biotechnology, 34(3):303-311.
Zhou et al., 2001, Counting alleles reveals a connection between chromosome 18q loss and vascular invasion. Nature Biotechnology, 19:78-81.
International Search Report and Written Opinion dated May 3, 2016 in PCT/US16/018354.
Office action dated Oct. 3, 2013 for U.S. Appl. No. 12/969,581.
Response with allowed claims dated Mar. 4, 2014 for U.S. Appl. No. 12/969,581.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Dec. 3, 2015 for U.S. Appl. No. 14/281,706.
Office Action dated Oct. 11, 2016 in U.S. Appl. No. 15/224,460.
Office action dated Jul. 20, 2016 for U.S. Appl. No. 14/281,706.
Office Action dated May 8, 2017 in U.S. Appl. No. 15/224,460.
Office Action dated May 7, 2015 for U.S. Appl. No. 13/327,526.
Notice of allowance dated Jan. 21, 2016 for U.S. Appl. No. 13/327,526.
Office action dated Feb. 18, 2015 for U.S. Appl. No. 14/540,007.
Office action dated Sep. 24, 2015 for U.S. Appl. No. 14/540,007.
Notice of allowance dated Dec. 15, 2015 for U.S. Appl. No. 14/540,007.
Office action dated Mar. 19, 2015 for U.S. Appl. No. 14/540,018.
Office action dated Oct. 6, 2015 for U.S. Appl. No. 14/540,018.
Notice of allowance dated Dec. 21, 2015 for U.S. Appl. No. 14/540,018.
Office Action dated Feb. 26, 2015 for U.S. Appl. No. 14/540,029.
Office action dated Sep. 1, 2015 for U.S. Appl. No. 14/540,029.
Office Action dated Jul. 28, 2017 in U.S. Appl. No. 14/975,441.
International Search Report and Written Opinion dated Jun. 6, 2012 in PCT/US11/065291.
Restriction Requirement dated Mar. 15, 2016 in U.S. Appl. No. 14/381,488.
Office Action dated May 10, 2016 in U.S. Appl. No. 14/381,488.
Office Action dated Aug. 12, 2016 in U.S. Appl. No. 14/381,488.
Office Action dated Feb. 13, 2017 in U.S. Appl. No. 14/381,488.
Office Action dated Jun. 7, 2017 in U.S. Appl. No. 14/381,488.
International Search Report and Written Opinion dated Sep. 6, 2013 in PCT/US13/028103.
Office Action dated Feb. 17, 2017 in Canadian patent application No. 2,865,575.
Office Action dated Jun. 6, 2016 in Chinese patent application No. 201380022187.9.
Office Action dated Dec. 27, 2016 in Chinese patent application No. 201380022187.9.
Office Action dated Jul. 14, 2017 in Chinese patent application No. 201380022187.9.
European search report and search opinion dated Jul. 17, 2015 for European patent application No. 13755319.4.
Examination report dated Jul. 12, 2016 in European patent application No. 13755319.4.
Search and Examination Report dated Aug. 6, 2014 for GB patent application No. 1408829.8.
Search and Examination Report dated Jan. 27, 2016 in GB patent application No. 1408829.8.
Examination Report dated Jun. 8, 2016 in GB patent application No. 1408829.8.
Official Action dated Dec. 28, 2016 in Japanese patent application No. 2014-558975.
Search Report and Written Opinion dated Mar. 1, 2016 in Singapore patent application No. 11201405274W.
Written Opinion dated May 26, 2017 in Singapore patent application No. 11201405274W.
International search report and written opinion dated Aug. 16, 2013 for PCT/US2013/027891.
Extended European Search Report dated Dec. 15, 2015 in European patent application No. 13754428.4.
Restriction Requirement dated Mar. 17, 2016 in U.S. Appl. No. 14/472,363.
Office Action dated Apr. 11, 2016 in U.S. Appl. No. 14/472,363.
Office action dated Dec. 31, 2015 for U.S. Appl. No. 14/800,526.
Office action dated Apr. 11, 2016 for U.S. Appl. No. 14/800,526.
Office action dated Aug. 17, 2016 for U.S. Appl. No. 14/800,526.
Office Action dated Oct. 25, 2016 in U.S. Appl. No. 14/872,337.
Office action dated Sep. 26, 2016 in U.S. Appl. No. 15/167,807.
International Search Report and Written Opinion dated Feb. 3, 2015 in PCT/US/14/053301.
Examination Report dated Apr. 10, 2017 in European patent application No. 14761937.3.
Search and Examination Report dated Aug. 26, 2015 in GB patent application No. 1511591.8.
Examination Report dated Feb. 19, 2016 in Great Britain patent application No. GB1511591.8.
Examination Report dated Jun. 15, 2016 in Great Britain patent application No. GB1511591.8.
Combined Search and Examination Report dated Feb. 21, 2017 in GB patent application No. 1609740.4.
Office Action dated May 13, 2016 in U.S. Appl. No. 14/508,911.
Office Action dated Mar. 24, 2017 in U.S. Appl. No. 15/409,355.
International search report and written opinion dated Dec. 19, 2014 for PCT Application No. US2014/059542.
International Search Report and Written Opinion dated Jun. 20, 2016 in PCT/US16/14612.

(56) References Cited

OTHER PUBLICATIONS

Office Action dated Jan. 19, 2017 in U.S. Appl. No. 15/055,445.
International Search Report and Written Opinion dated Jun. 17, 2016 in PCT/US16/019962.
Written Opinion dated Jul. 5, 2016 in PCT/US16/019962.
Written Opinion dated Sep. 27, 2016 in PCT/US16/019962.
Invitation to Pay Additional Search Fees dated Jun. 2, 2016 in PCT/US16/019971.
International Search Report and Written Opinion dated Aug. 9, 2016 in PCT/US16/019971.
International Search Report and Written Opinion dated Jun. 9, 2016 in PCT/US16/022712.
International Search Report and Written Opinion dated Dec. 5, 2016 in PCT/US16/024783.
International Search Report and Written Opinion dated Sep. 28, 2016 in PCT/US16/028694.
International Search Report and Written Opinion dated Sep. 27, 2016 in PCT/US16/034473.
International Search Report and Written Opinion dated Jan. 31, 2017 in PCT/US16/050694.
International Search Report and Written Opinion dated Aug. 7, 2017 in PCT/US2017/034576.
International search report and written opinion dated May 7, 2012 for PCT/IB2011/003160.
Notice of opposition dated Jul. 22, 2015 for European patent application No. 11810645.9.
Notice of opposition dated Jul. 9, 2015 for European patent application No. 11810645.9.
Written Opinion dated Oct. 7, 2020 in Singapore patent application No. 11201903158R.
Office Action dated Oct. 30, 2020 in U.S. Appl. No. 15/806,223.
Written Opinion dated Oct. 8, 2020 in Singapore patent application No. 11201903139S.
Examination Report dated Nov. 5, 2020 in European patent application No. 18716453.8.
Di Carlo et al., Dec. 1, 2008, Dynamic single-cell analysis for quantitative biology, Analytical Chemistry, 78(23):7918-7925.
Lau et al., Sep. 21, 2017, Single molecule counting and assessment of random molecular tagging errors with transposable giga-scale error-correcting barcodes, BMC Genomics, 18(1):1-13.
Peng et al. Aug. 7, 2015 Supplemental Material BMC Bioinformatics 16:589.
Shiroguchi et al. (2012) Supplemental Material PNAS 109 4.
Smith et al., Jan. 18, 2017, UMI-tools: modeling sequencing errors in unique molecular identifiers to improve quantification accuracy, Genome Research, 27(3):491-499.
Tung et al., Jan. 3, 2017, Batch effects and the effective design of single-cell gene expression studies. Nature Scientific Reports, 7:39921, 15 pp.
Zorita et al., Jan. 31, 2015 Starcode: sequence clustering based on all pairs search. Bioinformatics, 13(12):1913-1919.
Third Party Observation dated Jun. 14, 2018 in Japanese patent application No. 2016-537867.
Official Action dated Jul. 30, 2018 in Japanese patent application No. 2016-537867.
Office Action dated Jul. 20, 2020 in U.S. Appl. No. 15/605,874.
Examination Report dated Apr. 2, 2020 in European patent application No. 17805040.7.
Office Action dated Apr. 15, 2020 in U.S. Appl. No. 15/806,223.
International Search Report and Written Opinion dated Jul. 18, 2018 in PCT/US2018/023387.
International Search Report and Written Opinion dated Feb. 28, 2019 in PCT/US2018/052365.
Johnson, Sep. 1967, Hierarchical clustering schemes, Psychometrika, 32(3):241-254.
Murtagh et al., 2012, Algorithms for hierarchical clustering: an overview, WIREs Data Mining and Knowledge Discovery, 2:86-97.
Office Action dated Jan. 6, 2021 in U.S. Appl. No. 15/605,874.
First Office Action dated Jun. 18, 2021 in Chinese patent application No. 201780028283.2.
Examination report dated Dec. 22, 2020 in European patent application No. 17728398.3.
Notice of Reasons for Rejection dated Jul. 8, 2021 in Japanese patent application No. 2018-561218.
Examination Report dated May 27, 2021 in European patent application No. 17805040.7.
Examination report dated Apr. 15, 2021 in European patent application No. 17805344.3.
Office Action with English Translation dated Jun. 29, 2022, in Japanese Patent Application No. 2019-523874.
Office Action dated Jul. 1, 2022, in Singapore Patent Application No. 11201903158R.
Final Office Action dated Apr. 26, 2022 in U.S. Appl. No. 15/926,977 in 20 pages.
Office action dated Mar. 2, 2022 in U.S. Appl. No. 16/139,699 in 93 pages.
Anders et al., Jan. 7, 2010, Differential expression analysis for sequence count data. Nature Precedings, pp. 1-13.
Becton, Dickinson and Company, 2016, BD™ Precise Assays pamphlet, www.bdbiosciences.com, 2 pp.
Bolotin et al., 2015. MiXCR software for comprehensive adaptive immunity profiling. MiXCR Documentation, pp. 1-3.
Bolotin et al., 2015. MiXCR software for comprehensive adaptive immunity profiling. Nature methods Supplemental, 12(5), pp. 1-14.
Bolotin, D.A., Poslavsky, S., Mitrophanov, I., Shugay, M., Mamedov, I.Z., Putintseva, E.V. and Chudakov, D.M., 2015. MiXCR software for comprehensive adaptive immunity profiling. Nature methods, 12(5), pp. 380-381. (Year: 2015).
Edgar, 2016. UNOISE2: improved error-correction for Illumina 16S and ITS amplicon sequencing. BioRxiv, p. 081257, pp. 1-21.
Fu, Oct. 15, 2015, Molecular indexing with precise assays: Technique enables single-cell gene analysis eliminating amplification bias. Genetic Engineering & Biotechnology News, 35(18):28-29.
Grun et al., Nov. 5, 2015, Design and analysis of single-cell sequencing experiments, Cell, 163:799-810.
Ilicic et al., 2016, Classification of low quality cells from single-cell RNA-seq data, Genome Bioloigy, 127:29.
Jaitin et al., 2015, Each cell counts: hematopoiesis and immunity reseach in the era of single cell genomics, Seminars in Immunology, 27:67-71.
Smyth et al., 2010, Reducing chimera formation during PCR amplification to ensure accurate genotyping. Gene, 469(1-2):45-51.
Wagner et al., 2013, A model based criterion for gene expression calls using RNA-seq data, Theory in Biosciences, 132(3):159-164.
Wang et al., 2016, A complete workflow from single cell isolation to mRNA sequencing analysis. Becton Dickinson/genomics White Paper, www.bd.com/genomics, 7 pp.
Notification of Reasons for Refusal dated Oct. 4, 2021 in Japanese patent application No. 2019-523874.
Examination Report No. 1 dated Oct. 29, 2021 in Australian patent application No. 2017359048.
Notice of Reasons for Rejection dated Dec. 15, 2021 in Japanese patent application No. 2019-523873.
Office action dated Nov. 23, 2021 in U.S. Appl. No. 15/926,977.
Notice of Reasons for Rejection dated Nov. 29, 2021 in Japanese patent application No. 2019-552517.
Office Action with English Translation dated Mar. 3, 2022 in Chinese Patent Application No. 2017800682996.
Notice of Allowance dated Mar. 23, 2022 in U.S. Appl. No. 15/605,874 in 11 pages.
Office Action dated Dec. 5, 2022 in Chinese Patent Application No. 2017800682996 in 5 pages, with English translation.

* cited by examiner

METHODS FOR CELL LABEL CLASSIFICATION

RELATED APPLICATIONS

The present application claims priority under 35 U.S.C. § 119(e) to U.S. Provisional Application No. 62/419,194, filed on Nov. 8, 2016; and U.S. Provisional Application No. 62/445,546, filed on Jan. 12, 2017. The content of each of these related applications is herein expressly incorporated by reference in its entirety.

BACKGROUND

Field

The present disclosure relates generally to the field of molecular barcoding and more particularly identifying and correcting noise cell labels.

Description of the Related Art

Methods and techniques such as stochastic barcoding are useful for cell analysis, in particular deciphering gene expression profiles to determine the states of cells using, for example, reverse transcription, polymerase chain reaction (PCR) amplification, and next generation sequencing (NGS). However, these methods and techniques can introduce errors, if uncorrected, may result in overestimated cell counts.

SUMMARY

Disclosed herein are methods for identifying a signal cell label. In some embodiments, the method comprises: (a) barcoding (e.g., stochastically barcoding) a plurality of targets in a sample of cells using a plurality of barcodes (e.g., stochastic barcodes) to create a plurality of barcoded targets (e.g., stochastically barcoded targets), wherein each of the plurality of barcodes comprises a cell label and a molecular label; (b) obtaining sequencing data of the plurality of barcoded targets; (c) determining the number of molecular labels with distinct sequences associated with each of the cell labels of the plurality of barcodes; (d) determining a rank of each of the cell labels of the plurality of barcodes based on the number of molecular labels with distinct sequences associated with each of the cell labels; (e) generating a cumulative sum plot based on the number of molecular labels with distinct sequences associated with each of the cell labels determined in (c) and the rank of each of the cell labels determined in (d); (f) generating a second derivative plot of the cumulative sum plot; (g) determining a minimum of the second derivative plot of the cumulative sum plot, wherein the minimum of the second derivative plot corresponds to a cell label threshold; and (h) identifying each of the cell labels as a signal cell label or a noise cell label based on the number of molecular labels with distinct sequences associated with each of the cell labels determined in (c) and the cell label threshold determined in (g).

In some embodiments, the method comprises, if a cell label of the plurality of barcodes is identified as a noise cell label in (h), removing sequencing information associated with the identified cell label from the sequencing data obtained in (b). The method can comprise removing sequencing information associated with molecular labels with distinct sequences associated with a target of the plurality of targets from the sequencing data obtained in (b) if the number of the molecular labels with distinct sequences associated with the target of the plurality of targets is above a molecular label occurrence threshold.

In some embodiments, wherein determining the number of molecular labels with distinct sequences associated with each of the cell labels in (c) comprises removing sequencing information associated with non-unique molecular labels associated with each of the cell labels from the sequencing data. The cumulative sum plot can be a log-log plot. The log-log plot can be a log 10-log 10 plot.

In some embodiments, generating the cumulative sum plot based on the number of molecular labels with distinct sequences associated with each of the cell labels determined in (c) and the rank of each of the cell labels determined in (d) comprises: determining a cumulative sum for each rank of the cell labels, wherein the cumulative sum for the rank comprises a summation of a number of molecular labels with distinct sequences associated with each of the cell labels with a lower rank. Generating the second derivative plot of the cumulative sum plot can comprise determining a difference between a cumulative sum of a first rank of the cell labels and a cumulative sum of a second rank of the cell labels over a difference between the first rank and the second rank. The difference between the first rank and the second rank can be one.

In some embodiments, the minimum is a global minimum. Determining the minimum of the second derivative plot comprises determining a minimum of the second derivative plot above a threshold of a minimum number of molecular labels associated with each of the cell labels.

In some embodiments, the threshold of the minimum number of molecular labels associated with each of the cell labels is a percentile threshold. The threshold of the minimum number of molecular labels associated with each of the cell labels is determined based on the number of cells in the sample of cells.

In some embodiments, determining the minimum of the second derivative plot comprises determining a minimum of the second derivative plot below a threshold of a maximum number of molecular labels associated with each of the cell labels. The threshold of the maximum number of molecular labels associated with each of the cell labels can be a percentile threshold. The threshold of the maximum number of molecular labels associated with each of the cell labels can be determined based on the number of cells in the sample of cells.

In some embodiments, each of the cell labels is identified as the signal cell label if the number of molecular labels with distinct sequences associated with the each of the cell labels determined in (c) is greater than the cell label threshold. Each of the cell labels can be identified as a noise cell label if the number of molecular labels with distinct sequences associated with the each of the cell labels determined in (c) is not greater than the cell label threshold.

In some embodiments, the method comprises: (i) for one or more of the plurality of targets: (1) counting the number of molecular labels with distinct sequences associated with the target in the sequencing data; and (2) estimating the number of the target based on the number of molecular labels with distinct sequences associated with the target in the sequencing data counted in (1).

Disclosed herein are methods for determining a signal cell label. In some embodiments, the method comprises: (a) obtaining sequencing data of a plurality of barcoded targets (e.g., stochastically barcoded targets), wherein the plurality of barcoded targets is created from a plurality of targets in a sample of cells that are barcoded (e.g., stochastically barcoded) using a plurality of barcodes (e.g., stochastic barcodes), and wherein each of the plurality of barcodes comprises a cell label and a molecular label; (b) determining a rank of each of the cell labels of the plurality of barcoded targets (or barcodes) based on the number of molecular labels with distinct sequences associated with each of the cell labels of the plurality of barcoded targets (or barcodes); (c) determining a cell label threshold based on the number of molecular labels with distinct sequences associated with each of the cell labels and the rank of each of the cell labels of the plurality of barcoded targets (or barcodes) determined in (b); and identifying each of the cell labels as a signal cell label or a noise cell label based on the number of molecular labels with distinct sequences associated with each of the cell labels and the cell label threshold determined in (c).

In some embodiments, the method comprises determining the number of molecular labels with distinct sequences associated with each of the cell labels. Determining the number of molecular labels with distinct sequences associated with each of the cell labels can comprise removing sequencing information associated with non-unique molecular labels associated with the cell label from the sequencing data.

In some embodiments, determining the cell label threshold based on the number of molecular labels with distinct sequences associated with each of the cell labels of the plurality of barcoded targets comprises: determining the cell label with the largest change in a cumulative sum for the cell label with a rank n and a cumulative sum for the cell label with the next rank n+1, wherein a number of molecular labels with distinct sequences associated with the cell label corresponds to the cell label threshold.

In some embodiments, determining the cell label threshold based on the number of molecular labels with distinct sequences associated with each of the cell labels of the plurality of barcoded targets and the rank of each of the cell labels of the plurality of barcoded targets determined in (b) comprises: determining a cumulative sum for each rank of the cell labels, wherein the cumulative sum for the rank comprises a summation of a number of molecular labels with distinct sequences associated with each of the cell labels with a lower rank; and determining a rank n of the cell labels with the largest change in a cumulative sum for the rank n and a cumulative sum for the next rank n+1, wherein the rank n of the cell labels with the largest change in the cumulative sum and the cumulative sum for the next rank n+1 corresponds to the cell label threshold.

In some embodiments, determining the cell label threshold based on the number of molecular labels with distinct sequences associated with each of the cell labels of the plurality of barcoded targets and the rank of each of the cell labels of the plurality of barcoded targets determined in (b) comprises: generating a cumulative sum plot based on the number of molecular labels with distinct sequences associated with each of the cell labels and the rank of each of the cell labels determined in (b); generating a second derivative plot of the cumulative sum plot; and determining a minimum of the second derivative plot of the cumulative sum plot, wherein the minimum of the second derivative plot corresponds to the cell label threshold. Generating the cumulative sum plot based on the number of molecular labels with distinct sequences associated with each of the cell labels and the rank of each of the cell labels determined in (b) can comprise: determining a cumulative sum for each rank of the cell labels, wherein the cumulative sum for the rank comprises a summation of a number of molecular labels with distinct sequences associated with each of the cell labels with a lower rank. Generating the second derivative plot of the cumulative sum plot can comprise determining a difference between a cumulative sum of a first rank of the cell labels and a cumulative sum of a second rank of the cell labels over a difference between the first rank and the second rank.

In some embodiments, the difference between the first rank and the second rank is one. In some embodiments, the method comprises removing, if a cell label of the plurality of barcoded targets is identified as a noise cell label in (d), sequencing information associated with the identified cell label from the sequencing data obtained in (a). The method can comprise removing sequencing information associated with molecular labels with distinct sequences associated with a target of the plurality of targets from the sequencing data obtained in (a) if the number of the molecular labels with distinct sequences associated with the target of the plurality of targets is above a molecular label occurrence threshold. The cumulative sum plot can be a log-log plot. The log-log plot can be a log 10-log 10 plot.

In some embodiments, the minimum is a global minimum. Determining the minimum of the second derivative plot can comprise determining a minimum of the second derivative plot above a threshold of a minimum number of molecular labels associated with each of the cell labels. The threshold of the minimum number of molecular labels associated with each of the cell labels can be a percentile threshold. The threshold of the minimum number of molecular labels associated with each of the cell labels can be determined based on the number of cells in the sample of cells.

In some embodiments, determining the minimum of the second derivative plot comprises determining a minimum of the second derivative plot below a threshold of a maximum number of molecular labels associated with each of the cell labels. The threshold of the maximum number of molecular labels associated with each of the cell labels can be a percentile threshold. The threshold of the maximum number of molecular labels associated with each of the cell labels can be determined based on the number of cells in the sample of cells.

In some embodiments, each of the cell labels is identified as the signal cell label if the number of molecular labels with distinct sequences associated with the each of the cell labels determined in (c) is greater than the cell label threshold. Each of the cell labels can be identified as a noise cell label if the number of molecular labels with distinct sequences associated with the each of the cell labels determined in (c) is not greater than the cell label threshold.

In some embodiments, the method comprises: (e) for one or more of the plurality of targets: (1) counting the number of molecular labels with distinct sequences associated with the target in the sequencing data; and (2) estimating the number of the target based on the number of molecular labels with distinct sequences associated with the target in the sequencing data counted in (1).

Disclosed herein are embodiments of a method for identifying a signal cell label. In some embodiments, the method comprises: (a) obtaining sequencing data of a plurality of targets of cells, wherein each target is associated with a number of molecular labels with distinct sequences associated with each cell label of a plurality of cell labels; (b) determining a cell label threshold based on the number of molecular labels with distinct sequences associated with each of the cell labels; and (c) identifying each of the cell labels as a signal cell label or a noise cell label based on the number of molecular labels with distinct sequences associated with each of the cell labels and the cell label threshold.

In some embodiments, obtaining sequencing data comprises: barcoding the plurality of targets of the cells using a plurality of barcodes to create a plurality of barcoded targets, wherein each of the plurality of barcodes comprises a cell label of the plurality of cell labels and a molecular label; and determining the number of molecular labels with distinct sequences associated with each of the cell labels of the plurality of barcodes. In some embodiments, the method comprises: for one or more of the plurality of targets: (1) counting the number of molecular labels with distinct sequences associated with the target in the sequencing data; and (2) estimating the number of the target based on the number of molecular labels with distinct sequences associated with the target in the sequencing data counted in (1). The method can comprise, if a cell label of the plurality of barcodes is identified as a noise cell label: removing sequencing information associated with the identified cell label from the sequencing data. The method can comprise: removing sequencing information associated with molecular labels with distinct sequences associated with a target of the plurality of targets from the sequencing data if the number of the molecular labels with distinct sequences associated with the target of the plurality of targets is above a molecular label occurrence threshold. In some embodiments, determining the number of molecular labels with distinct sequences associated with each of the cell labels in (c) comprises removing sequencing information associated with non-unique molecular labels associated with each of the cell labels from the sequencing data.

In some embodiments, determining the cell label threshold comprises: determining an inflection point of a cumulative sum plot, wherein the cumulative sum plot is based on the number of molecular labels with distinct sequences associated with each of the plurality of cell labels and a rank of each of the cell labels, and wherein the inflection point corresponds to the cell label threshold. Determining the inflection point of the cumulative sum plot can comprise: generating the cumulative sum plot based on the number of molecular labels with distinct sequences associated with each of the plurality of cell labels and the rank of each of the cell labels; generating a second derivative plot of the cumulative sum plot; and determining a minimum of the second derivative plot of the cumulative sum plot, wherein the minimum of the second derivative plot corresponds to a cell label threshold. Determining the cell label threshold can comprise: determining the rank of each of the plurality of cell labels based on the number of molecular labels with distinct sequences associated with each of the cell labels. The cumulative sum plot can be a log-log plot, such as a log 10-log 10 plot.

In some embodiments, generating the cumulative sum plot based on the number of molecular labels with distinct sequences associated with each of the cell labels and the rank of each of the cell labels comprises: determining a cumulative sum for each rank of the cell labels, wherein the cumulative sum for the rank comprises a summation of a number of molecular labels with distinct sequences associated with each of the cell labels with a lower rank. Generating the second derivative plot of the cumulative sum plot can comprise determining a difference between a cumulative sum of a first rank of the cell labels and a cumulative sum of a second rank of the cell labels over a difference between the first rank and the second rank. The difference between the first rank and the second rank can be one. The minimum can be a global minimum. Determining the minimum of the second derivative plot can comprise: determining a minimum of the second derivative plot above a threshold of a minimum number of molecular labels associated with each of the cell labels. The threshold of the minimum number of molecular labels associated with each of the cell labels can be a percentile threshold. The threshold of the minimum number of molecular labels associated with each of the cell labels can be determined based on the number of the plurality of cells.

In some embodiments, determining the minimum of the second derivative plot comprises determining a minimum of the second derivative plot below a threshold of a maximum number of molecular labels associated with each of the cell labels. The threshold of the maximum number of molecular labels associated with each of the cell labels can be a percentile threshold. The threshold of the maximum number of molecular labels associated with each of the cell labels can be determined based on the number of the plurality of cells.

In some embodiments, each of the cell labels can be identified as the signal cell label if the number of molecular labels with distinct sequences associated with the each of the cell labels is greater than the cell label threshold. Each of the cell labels can be identified as a noise cell label if the number of molecular labels with distinct sequences associated with each of the cell labels is not greater than the cell label threshold.

Disclosed herein are methods for identifying a signal cell label. In some embodiments, the method comprises: (a) barcoding (e.g., stochastically barcoding) a plurality of targets in a sample of cells using a plurality of barcodes (e.g., stochastic barcodes) to create a plurality of barcoded targets (e.g., stochastically barcoded targets), wherein each of the plurality of barcodes comprises a cell label and a molecular label, wherein barcoded targets created from targets of different cells of the plurality of cells have different cell labels, and wherein barcoded targets created from targets of the same cell of the plurality of cells have different molecular labels; (b) obtaining sequencing data of the plurality of barcoded targets; (c) determining a feature vector of each cell label of the plurality of barcodes (or barcoded targets), wherein the feature vector comprise numbers of molecular labels with distinct sequences associated with the each cell label; (d) determining a cluster for the each cell label of the plurality of barcodes (or barcoded targets) based on the feature vector; and (e) identifying the each cell label of the plurality of stochastic barcodes (or barcoded targets) as a signal cell label or a noise cell label based on a number of cell labels in the cluster and a cluster size threshold.

In some embodiments, determining the cluster for the each cell label of the plurality of barcoded targets based on the feature vector comprises clustering the each cell label of the plurality of barcoded targets into the cluster based on a distance of the feature vector to the cluster in a feature vector space. Determining the cluster for each cell label of the plurality of barcoded targets based on the feature vector can comprise: projecting the feature vector from a feature vector space into a lower dimensional space; and clustering the each cell label into the cluster based on a distance of the feature vector to the cluster in the lower dimensional space.

In some embodiment, the lower dimensional space is a two dimensional space. Projecting the feature vector from the feature vector space into the lower dimensional space can comprise projecting the feature vector from the feature vector space into the lower dimensional space using a t-distributed stochastic neighbor embedding (tSNE) method. Clustering the each cell label into the cluster based on the distance of the feature vector to the cluster in the lower dimensional space can comprise clustering the each cell label into the cluster based on the distance of the feature vector to the cluster in the lower dimensional space using a density-based method. The density-based method can comprise a density-based spatial clustering of applications with noise (DBSCAN) method.

In some embodiments, the cell label is identified as the signal cell label if the number of cell labels in the cluster is below the cluster size threshold. The cell label can be identified as a noise cell label if the number of cell labels in the cluster is not below the cluster size threshold. The method can comprise: (f) for one or more of the plurality of targets: (1) counting the number of molecular labels with distinct sequences associated with the target in the sequencing data; and (2) estimating the number of the target based on the number of molecular labels with distinct sequences associated with the target in the sequencing data counted in (1).

In some embodiments, the method comprises determining the cluster size threshold based on the number of cell labels of the plurality of barcoded targets. The cluster size threshold can be a percentage of the number of cell labels of the plurality of barcoded targets. In some embodiments, the method comprises determining the cluster size threshold based on the number of cell labels of the plurality of barcodes. The cluster size threshold is a percentage of the number of cell labels of the plurality of barcodes. In some embodiments, the method comprises determining the cluster size threshold based on numbers of molecular labels with distinct sequences associated with each cell label of the plurality of barcodes.

Disclosed herein are methods for identifying a signal cell label. In some embodiments, the method comprises: (a) obtaining sequencing data of a plurality of barcoded targets (e.g., stochastically barcoded targets), wherein the plurality of barcoded targets is create from a plurality of targets in a sample of cells that are barcoded (e.g., stochastically barcoded) using a plurality of barcodes (e.g., stochastic barcodes), wherein each of the plurality of barcodes comprises a cell label and a molecular label, wherein barcoded targets created from targets of different cells of the plurality of cells have different cell labels, and wherein barcoded targets created from targets of the same cell of the plurality of cells have different molecular labels; (b) determining a feature vector of each cell label of the plurality of barcoded targets, wherein the feature vector comprise numbers of molecular labels with distinct sequences associated with the each cell label; (c) determining a cluster for the each cell label of the plurality of barcoded targets based on the feature vector; and (d) identifying the each cell label of the plurality of barcoded targets as a signal cell label or a noise cell label based on a number of cell labels in the cluster and a cluster size threshold.

In some embodiments, determining the cluster for the each cell label of the plurality of barcoded targets based on the feature vector comprises clustering the each cell label of the plurality of barcoded targets into the cluster based on a distance of the feature vector to the cluster in a feature vector space. Determining the cluster for the each cell label of the plurality of barcoded targets based on the feature vector comprises: projecting the feature vector from a feature vector space into a lower dimensional space; and clustering the each cell label into the cluster based on a distance of the feature vector to the cluster in the lower dimensional space. The lower dimensional space can be a two dimensional space.

In some embodiments, projecting the feature vector from the feature vector space into the lower dimensional space comprises projecting the feature vector from the feature vector space into the lower dimensional space using a t-distributed stochastic neighbor embedding (tSNE) method. Clustering the each cell label into the cluster based on the distance of the feature vector to the cluster in the lower dimensional space can comprise clustering the each cell label into the cluster based on the distance of the feature vector to the cluster in the lower dimensional space using a density-based method. The density-based method can comprises a density-based spatial clustering of applications with noise (DBSCAN) method.

In some embodiments, the cell label can be identified as the signal cell label if the number of cell labels in the cluster is below the cluster size threshold. The cell label can be identified as a noise cell label if the number of cell labels in the cluster is not below the cluster size threshold.

In some embodiments, the method comprises determining the cluster size threshold based on the number of cell labels of the plurality of barcoded targets. The cluster size threshold can be a percentage of the number of cell labels of the plurality of barcoded targets. In some embodiments, determining the cluster size threshold based on the number of cell labels of the plurality of barcodes. The cluster size threshold can be a percentage of the number of cell labels of the plurality of barcodes. In some embodiments, the method comprises determining the cluster size threshold based on numbers of molecular labels with distinct sequences associated with each cell label of the plurality of barcodes.

In some embodiments, the method comprises: (e) for one or more of the plurality of targets: (1) counting the number of molecular labels with distinct sequences associated with the target in the sequencing data; and (2) estimating the number of the target based on the number of molecular labels with distinct sequences associated with the target in the sequencing data counted in (1).

Disclosed herein are embodiments of a method for identifying a signal cell label. In some embodiments, the method comprises: (a) obtaining sequencing data of a plurality of first targets of cells, wherein each first target is associated with a number of molecular labels with distinct sequences associated with each cell label of a plurality of cell labels; (b) identifying each of the cell labels as a signal cell label or a noise cell label based on the number of molecular labels with distinct sequences associated with each of the cell labels and an identification threshold; and (c) re-identifying at least one of the plurality of cell labels as a signal cell label identified as a noise cell label in (b) or re-identifying at least one of the cell label as a noise cell label identified as a signal cell label in (b). Identifying each of the cell labels, re-identifying at least one of the plurality of cells labels as a signal cell label, or re-identifying at least one of the plurality of cell labels as a noise cell label can be based on an identical cell label identification method or different cell label identification methods of the disclosure. The identification threshold can comprise a cell label threshold, a cluster size threshold, or any combination thereof. The method can comprise: removing one or more cell labels of the plurality of cell labels each associated with a number of molecular labels with distinct sequences below threshold of a number of molecular labels.

In some embodiments, re-identifying at least one of the plurality of cell labels as a signal cell label identified as a noise cell label in (b) comprises: determining a plurality of second targets of the plurality of first targets each with one or more variability indications, amongst the plurality of first targets, above a variability threshold; and re-identifying at least one of the plurality of cell labels as a signal cell label identified as a noise cell label in (b) based on, for each of the plurality of cell labels, the number of molecular labels with distinct sequences associated with the plurality of second targets and the identification threshold. The one or more variability indications of the second target can comprise an average, a maximum, a median, a minimum, a dispersion, or any combinations thereof, of the numbers of molecular labels with distinct sequences associated with the second target and cell labels of the plurality of cell labels in the sequencing data. The one or more variability indications of the second target can comprise a standard deviation, a normalized dispersion, or any combinations thereof, variability indications of a subset of the plurality of second targets. The variability threshold can be smaller than or equal to the size of the subset of the plurality of second targets.

In some embodiments, re-identifying at least one of the plurality of cell labels as a noise cell label identified as a signal cell label in (b) comprises: determining a plurality of third targets of the plurality of first targets each with an association with cell labels identified as noise cell labels in (c) above an association threshold; and re-identifying at least one of the cell label as a noise cell label identified as a signal cell label in (b), for each of the plurality of cell labels, based on the number of molecular labels with distinct sequences associated with the plurality of third targets, and the identification threshold. Determining the plurality of third targets of the plurality of first targets each with an association with cell labels identified as noise cell labels in (c) above the association threshold can comprise: determining a plurality of remaining cells labels identified as signal cell labels after re-identifying at least one of the cell label as a signal cell label identified as a noise cell label in (b); determining the plurality of third targets based on for each of the plurality of cell labels, the number of molecular labels with distinct sequences associated with the plurality of targets, and for each of the plurality of remaining cell labels, the number of molecular labels with distinct sequences associated with the plurality of targets.

Disclosed herein are systems for identifying a signal cell label. In some embodiments, the system comprises: a hardware processor; and non-transitory memory having instructions stored thereon, which when executed by the hardware processor causes the processor to perform any of the methods disclosed herein. Disclosed herein are computer readable media for identifying a signal cell label. In some embodiments, the computer readable medium comprises code for performing any of the methods disclosed herein.

BRIEF DESCRIPTION OF THE DRAWINGS

FIGS. 13A-13B are the common cells detected by both methods. The dots labeled as red in FIG. 13A are the cells identified as noise by method 600a. The dots labeled as red in FIG. 13B are the additional true cells identified by method 600a.

FIGS. 15A-15B are the common cells detected by both methods. The dots labeled as red in FIG. 15A are the cells identified as noise by the method 600a. The dots labeled as red in FIG. 15B are the additional cells identified by the method 600a.

In FIG. 16A, the cells labeled as red are the cells identified as noise by the method 600a. In FIG. 16B, the cells are colored by expression of a group of Monocyte marker genes, such as CD14 and S100A6. The "noise" cells identified by the improved algorithm were mostly low expressers of the Monocytes.

DETAILED DESCRIPTION

Figure 1:
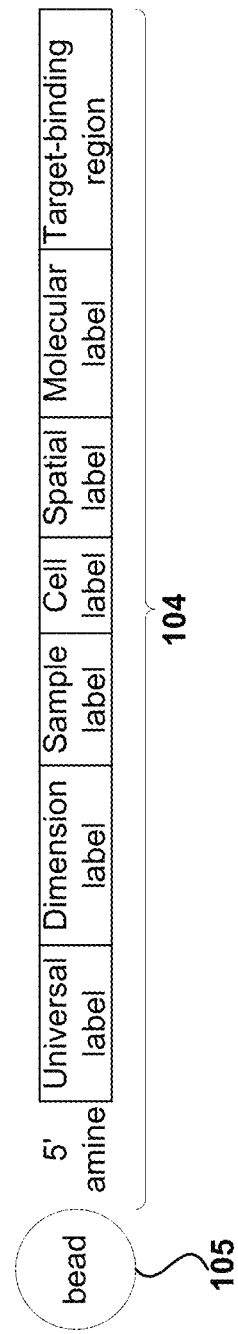
FIG. 1 illustrates a non-limiting exemplary barcode (e.g., a stochastic barcode).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Quantifying small numbers of nucleic acids or targets, for example messenger ribonucleotide acid (mRNA) molecules, is clinically important for determining, for example, the genes that are expressed in a cell at different stages of development or under different environmental conditions. However, it can be very challenging to determine the absolute number of nucleic acid molecules (e.g., mRNA molecules), especially when the number of molecules is very small. One method to determine the absolute number of molecules in a sample is digital polymerase chain reaction (PCR). Ideally, PCR produces an identical copy of a molecule at each cycle. However, PCR can have disadvantages such that each molecule replicates with a stochastic probability, and this probability varies by PCR cycle and gene sequence, resulting in amplification bias and inaccurate gene expression measurements.

Barcodes (e.g., stochastic barcodes) with unique molecular labels (MLs, also referred to as molecular indexes (MIs)) can be used to count the numbers of molecules. Barcodes with molecular labels that are unique for each cell label can be used to count the numbers of molecules in each cell. Non-limiting exemplary assays for barcoding include the Precise™ assay (Cellular Research, Inc. (Palo Alto, Calif.)), the Resolve™ assay (Cellular Research, Inc. (Palo Alto, Calif.)), or the Rhapsody™ assay (Cellular Research, Inc. (Palo Alto, Calif.)). However, these methods and techniques can introduce errors, if uncorrected, may result in overestimated cell counts.

The Rhapsody™ assay can utilize a non-depleting pool of barcodes (e.g., stochastic barcodes) with large number, for example 6561 to 65536, unique molecular labels on poly(T) oligonucleotides to hybridize to all poly(A)-mRNAs in a sample during the RT step. In addition to molecular labels, cell labels of the barcodes can be used to identify each single cell in each well of a microwell plate. A barcode can comprise a universal PCR priming site. During RT, target gene molecules react randomly with barcodes. Each target molecule can hybridize to a barcode (e.g., a stochastic barcode) resulting to generate barcoded complementary ribonucleotide acid (cDNA) molecules (e.g., stochastically barcoded cDNA molecules. After labeling, barcoded cDNA molecules from microwells of a microwell plate can be pooled into a single tube for PCR amplification and sequencing. Raw sequencing data can be analyzed to produce the numbers of barcodes with unique molecular labels.

Methods and systems for identifying a signal cell label are disclosed herein. In some embodiments, the method comprises: (a) barcoding (e.g., stochastically barcoding) a plurality of targets in a sample of cells using a plurality of barcodes (e.g., stochastic barcodes) to create a plurality of barcoded targets (e.g., stochastically barcoded targets), wherein each of the plurality of barcodes comprises a cell label and a molecular label; (b) obtaining sequencing data of the plurality of barcoded targets; (c) determining the number of molecular labels with distinct sequences associated with each of the cell labels of the plurality of barcodes; (d) determining a rank of each of the cell labels of the plurality of barcodes based on the number of molecular labels with distinct sequences associated with each of the cell labels; (e) generating a cumulative sum plot based on the number of molecular labels with distinct sequences associated with each of the cell labels determined in (c) and the rank of each of the cell labels determined in (d); (f) generating a second derivative plot of the cumulative sum plot; (g) determining a minimum of the second derivative plot of the cumulative sum plot, wherein the minimum of the second derivative plot corresponds to a cell label threshold; and (h) identifying the cell label as a signal cell label or a noise cell label based on the number of molecular labels with distinct sequences associated with the cell label determined in (c) and the cell label threshold.

In some embodiments, the method comprises: (a) obtaining sequencing data of a plurality of barcoded targets (e.g., stochastically barcoded targets), wherein the sequencing data of the plurality of barcoded targets are from a plurality of targets in a sample of cells that are barcoded (e.g., stochastically barcoded) using a plurality of barcodes (e.g., stochastic barcodes) to create the plurality of barcoded targets (e.g., stochastically barcoded targets), wherein each of the plurality of barcodes comprises a cell label and a molecular label; (b) determining a rank of each of the cell labels of the plurality of barcodes based on the number of molecular labels with distinct sequences associated with each of the cell labels; (c) determining a minimum of a second derivative plot of a cumulative sum plot, wherein the cumulative sum plot is based on the number of molecular labels with distinct sequences associated with each of the cell labels and the rank of each of the cell labels determined in (b), and wherein the minimum of the second derivative plot corresponds to a cell label threshold; and (d) identifying the cell label as a signal cell label (associated with a cell) or a noise cell label (not associated with a cell based on the number of molecular labels with distinct sequences associated with the cell label and the cell label threshold.

Disclosed herein are methods for identifying a signal cell label. In some embodiments, the method comprises: (a) barcoding (e.g., stochastically barcoding) a plurality of targets in a sample of cells using a plurality of barcodes (e.g., stochastic barcodes) to create a plurality of barcoded targets (e.g., stochastically barcoded targets), wherein each of the plurality of barcodes comprises a cell label and a molecular label, wherein barcoded targets created from targets of different cells have different cell labels, and wherein barcoded targets created from targets of one cell of the plurality of cells have different molecular labels; (b) obtaining sequencing data of the barcoded targets; (c) determining a feature vector of the cell label, wherein the feature vector comprise the numbers of the molecular labels with distinct sequences associated with the cell label; (d) determining a cluster for the cell label based on the feature vector; and (e) identifying the cell label as a signal cell label or a noise cell label based on the number of the cells in the cluster and a cluster size threshold.

Disclosed herein are systems for identifying a signal cell label. In some embodiments, the system comprises: a hardware processor; and non-transitory memory having instructions stored thereon, which when executed by the hardware processor causes the processor to perform any of the methods disclosed herein. Disclosed herein are computer readable media for identifying a signal cell label. In some embodiments, the computer readable medium comprises code for performing any of the methods disclosed herein.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, barcodes, stochastic barcodes, or molecular labels. The adapters can be linear. The adaptors can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can, in some embodiments, comprise a universal sequence. A universal sequence can be a region of nucleotide sequence that is common to two or more nucleic acid molecules. The two or more nucleic acid molecules can have regions of different sequence. Thus, for example, the 5' adapters can comprise identical and/or universal nucleic acid sequences and the 3' adapters can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adapters (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can be a physical association. In some embodiments, two or more associated species are "tethered", "attached", or "immobilized" to one another or to a common solid or semisolid surface. An association may refer to covalent or non-covalent means for attaching labels to solid or semisolid supports such as beads. An association may be a covalent bond between a target and a label.

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This stochastic methodology transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of stochastic barcodes made up of many different labels. A non-depleting reservoir can comprise large numbers of different stochastic barcodes such that when the non-depleting reservoir is associated with a pool of targets each target is likely to be associated with a unique stochastic barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of stochastic barcodes detected then allows calculation of the number of target molecules present in the original collection or sample. When the ratio of the number of copies of a target molecule present to the number of unique stochastic barcodes is low, the labeled target molecules are highly unique (i.e. there is a very low probability that more than one target molecule will have been labeled with a given label).

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of stochastic barcodes may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A plurality of solid supports spaced in an array may not comprise a substrate. A solid support may be used interchangeably with the term "bead."

A solid support can refer to a "substrate." A substrate can be a type of solid support. A substrate can refer to a continuous solid or semi-solid surface on which the methods of the disclosure may be performed. A substrate can refer to an array, a cartridge, a chip, a device, and a slide, for example.

As used here, the term, "spatial label" can refer to a label which can be associated with a position in space.

As used herein, the term "stochastic barcode" can refer to a polynucleotide sequence comprising labels. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "gene-specific stochastic barcoding."

As used here, the term "target" can refer to a composition which can be associated with a stochastic barcode. Exemplary suitable targets for analysis by the disclosed methods, devices, and systems include oligonucleotides, DNA, RNA, mRNA, microRNA, tRNA, and the like. Targets can be single or double stranded. In some embodiments targets can be proteins. In some embodiments targets are lipids.

As used herein, the term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transciptases, and group II intron reverse transcriptases. Examples of group II intron reverse transcriptases include the *Lactococcus lactis* Ll.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

Disclosed herein are systems and methods for identifying a signal cell label. In some embodiments, the method comprises: (a) stochastically barcoding a plurality of targets in a sample of cells using a plurality of stochastic barcodes to create a plurality of stochastically barcoded targets, wherein each of the plurality of stochastic barcodes comprises a cell label and a molecular label; (b) obtaining sequencing data of the plurality of stochastically barcoded targets; (c) determining the number of molecular labels with distinct sequences associated with each of the cell labels of the plurality of stochastic barcodes; (d) determining a rank of each of the cell labels of the plurality of stochastic barcodes based on the number of molecular labels with distinct sequences associated with each of the cell labels; (e) generating a cumulative sum plot based on the number of molecular labels with distinct sequences associated with each of the cell labels determined in (c) and the rank of each of the cell labels determined in (d); (f) generating a second derivative plot of the cumulative sum plot; (g) determining a minimum of the second derivative plot of the cumulative sum plot, wherein the minimum of the second derivative plot corresponds to a cell label threshold; and (h) identifying each of the cell labels as a signal cell label or a noise cell label based on the number of molecular labels with distinct sequences associated with each of the cell labels determined in (c) and the cell label threshold determined in (g).

Barcodes

Barcoding, such as stochastic barcoding, has been described in, for example, US20150299784, WO2015031691, and Fu et al, Proc Natl Acad Sci U.S.A. 2011 May 31; 108(22):9026-31 and Fan et al., Science (2015) 347(6222):1258367; the content of these publications is incorporated hereby in its entirety. In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be, for example, an mRNA species comprising mRNA molecules with identical or nearly identical sequences. Barcodes can be referred to as stochastic barcodes if the ratio of the number of different barcode sequences of the stochastic barcodes and the number of occurrence of any of the targets to be labeled is at least, or at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 1 illustrates an exemplary barcode 104 with a spatial label. The barcode 104 can comprise a 5' amine that may link the barcode to a solid support 105. The barcode can comprise a universal label, a dimension label, a spatial label, a cell label, and/or a molecular label. The order of different labels (including but not limited to the universal label, the dimension label, the spatial label, the cell label, and the molecule label) in the barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo (dT) sequence which can interact with poly(A) tails of mRNAs. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, or 20 or more nucleotides.

A label, for example the cell label, can comprise a unique set of nucleic acid sub-sequences of defined length, e.g. seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequence (e.g., a molecular label)) can be separated by a spacer from another one or two of the remaining labels of the barcode. The spacer can be, for example, 1, 2, 3, 4, 5, 6, 7, 8, 9, 10, 11, 12, 13, 14, 15, 16, 17, 18, 19, or 20 or more nucleotides. In some embodiments, none of the labels of the barcode is separated by spacer.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of beads. In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was stochastically barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were stochastically barcoded. For example, a population of cells can be stochastically barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be stochastically labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, or 10 or more times. The dimension label can be reversibly activatable, for example, at least 1, 2, 3, 4, 5, 6, 7, 8, 9, or 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., bead), but different for different solid supports (e.g., beads). In some embodiments, at least 60%, 70%, 80%, 85%, 90%, 95%, 97%, 99% or 100% of barcodes on the same solid support can comprise the same dimension label. In some embodiments, at least 60% of barcodes on the same solid support can comprise the same dimension label. In some embodiments, at least 95% of barcodes on the same solid support can comprise the same dimension label.

There can be as many as $10^6$ or more unique dimension label sequences represented in a plurality of solid supports (e.g., beads). A dimension label can be, or be about 1, 2, 3, 4, 5, 10, 15, 20, 25, 30, 35, 40, 45, 50, or a number or a range between any two of these values, nucleotides in length. A dimension label can be at least, or at most, 1, 2, 3, 4, 5, 10, 15, 20, 25, 30, 35, 40, 45, 50, 100, 200, or 300 nucleotides in length. A dimension label can comprise between about 5 to about 200 nucleotides. A dimension label can comprise between about 10 to about 150 nucleotides. A dimension label can comprise between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g. a well, a container, or a droplet). In some embodiments, multiple spatial labels are used together to encode one or more positions in space.

The spatial label can be identical for all barcodes attached to a given solid support (e.g., bead), but different for different solid supports (e.g., beads). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or at most, 60%, 70%, 80%, 85%, 90%, 95%, 97%, 99%, or 100%. In some embodiments, at least 60% of barcodes on the same solid support can comprise the same spatial label. In some embodiments, at least 95% of barcodes on the same solid support can comprise the same spatial label.

There can be as many as $10^6$ or more unique spatial label sequences represented in a plurality of solid supports (e.g., beads). A spatial label can be, or be about, 1, 2, 3, 4, 5, 10, 15, 20, 25, 30, 35, 40, 45, 50, or a number or a range between any two of these values, nucleotides in length. A spatial label can be at least or at most 1, 2, 3, 4, 5, 10, 15, 20, 25, 30, 35, 40, 45, 50, 100, 200, or 300 nucleotides in length. A spatial label can comprise between about 5 to about 200 nucleotides. A spatial label can comprise between about 10 to about 150 nucleotides. A spatial label can comprise between about 20 to about 125 nucleotides in length.

Cell Labels

A barcode can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., bead), but different for different solid supports (e.g., beads). In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about 60%, 70%, 80%, 85%, 90%, 95%, 97%, 99%, or 100%. For example, at least 60% of barcodes on the same solid support can comprise the same cell label. As another example, at least 95% of barcodes on the same solid support can comprise the same cell label.

There can be as many as $10^6$ or more unique cell label sequences represented in a plurality of solid supports (e.g., beads). A cell label can be, or be about, 1, 2, 3, 4, 5, 10, 15, 20, 25, 30, 35, 40, 45, 50, or a number or a range between any two of these values, nucleotides in length. A cell label can be at least, or at most, 1, 2, 3, 4, 5, 10, 15, 20, 25, 30, 35, 40, 45, 50, 100, 200, or 300 nucleotides in length. For example, a cell label can comprise between about 5 to about 200 nucleotides. As another example, a cell label can comprise between about 10 to about 150 nucleotides. As yet another example, a cell label can comprise between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or at most, $10^2$, $10^3$, $10^4$, $10^5$, $10^6$, $10^7$, $10^8$, or $10^9$, unique barcode sequences. The unique molecular label sequences can be attached to a given solid support (e.g., bead).

A barcode can be, or be about, 1, 2, 3, 4, 5, 10, 15, 20, 25, 30, 35, 40, 45, 50, or a number or a range between any two of these values, nucleotides in length. A barcode can be at least, or at most, 1, 2, 3, 4, 5, 10, 15, 20, 25, 30, 35, 40, 45, 50, 100, 200, or 300 nucleotides in length.

Molecular Labels

A stochastic barcode can comprise one or more molecular labels. Molecular labels can include barcode sequences. In some embodiments, a molecular label can comprise a nucleic acid sequence that provides identifying information for the specific type of target nucleic acid species hybridized to the stochastic barcode. A molecular label can comprise a nucleic acid sequence that provides a counter for the specific occurrence of the target nucleic acid species hybridized to the stochastic barcode (e.g., target-binding region).

In some embodiments, a diverse set of molecular labels are attached to a given solid support (e.g., bead). In some embodiments, there can be, or be about, $10^2$, $10^3$, $10^4$, $10^5$, $10^6$, $10^7$, $10^8$, $10^9$, or a number or a range of unique molecular label sequences. For example, a plurality of stochastic barcodes can comprise about 6561 molecular labels with distinct sequences. As another example, a plurality of stochastic barcodes can comprise about 65536 molecular labels with distinct sequences. In some embodiments, there can be at least, or at most, $10^2$, $10^3$, $10^4$, $10^5$, $10^6$, $10^7$, $10^8$, or $10^9$, unique molecular label sequences. Stochastic barcodes with the unique molecular label sequences can be attached to a given solid support (e.g., bead).

For stochastic barcoding using a plurality of stochastic barcodes, the ratio of the number of different molecular label sequences and the number of occurrence of any of the targets can be, or about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or at most, 1, 2, 3, 4, 5, 10, 15, 20, 25, 30, 35, 40, 45, 50, 100, 200, or 300 nucleotides in length.

Target-Binding Region

A barcode can comprise one or more target binding regions, such as capture probes. In some embodiments, a target-binding region can hybridize with a target of interest. In some embodiments, the target binding regions can comprise a nucleic acid sequence that hybridizes specifically to a target (e.g. target nucleic acid, target molecule, e.g., a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g. an EcoRI sticky-end overhang). The barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, or an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all barcodes attached to a given bead. In some embodiments, the target binding regions for the plurality of barcodes attached to a given bead can comprise two or more different target binding sequences. A target binding region can be, or be about, 5, 10, 15, 20, 25, 30, 35, 40, 45, 50, or a number or a range between any two of these values, nucleotides in length. A target binding region can be at most about 5, 10, 15, 20, 25, 30, 35, 40, 45, 50 or more nucleotides in length.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

Orientation Property

A barcode can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be stochastically labeled. The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like.

In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A barcode can comprise one or more universal adaptor primers. For example, a gene-specific barcode, such as a gene-specific stochastic barcode, can comprise a universal adaptor primer. A universal adaptor primer can refer to a nucleotide sequence that is universal across all barcodes. A universal adaptor primer can be used for building gene-specific barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these nucleotides in length. A universal adaptor primer can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Linker

When a barcode comprises more than one of a type of label (e.g., more than one cell label or more than one barcode sequence, such as one molecular label), the labels may be interspersed with a linker label sequence. A linker label sequence can be at least about 5, 10, 15, 20, 25, 30, 35, 40, 45, 50 or more nucleotides in length. A linker label sequence can be at most about 5, 10, 15, 20, 25, 30, 35, 40, 45, 50 or more nucleotides in length. In some instances, a linker label sequence is 12 nucleotides in length. A linker label sequence can be used to facilitate the synthesis of the barcode. The linker label can comprise an error-correcting (e.g., Hamming) code.

Solid Supports

Barcodes, such as stochastic barcodes, disclosed herein can, in some embodiments, be associated with a solid support. The solid support can be, for example, a synthetic particle. In some embodiments, some or all of the barcode sequence, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The bead can be, for example, a silica gel bead, a controlled pore glass bead, a magnetic bead, a Dynabead, a Sephadex/Sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof.

In some embodiments, the bead can be a polymeric bead, for example a deformable bead or a gel bead, functionalized with barcodes or stochastic barcodes (such as gel beads from 10× Genomics (San Francisco, Calif.). In some implementation, a gel bead can comprise a polymer based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the particle can be degradable. For example, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combinations thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some embodiments, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte. In some embodiments, at least one barcode of the plurality of barcodes can be immobilized on the particle, partially immobilized on the particle, enclosed in the particle, partially enclosed in the particle, or any combination thereof.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the beads. Examples of these chemical changes may include, but are not limited to pH-mediated changes to the bead wall, disintegration of the bead wall via chemical cleavage of cross-link bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption, dissolution, or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules may allow triggered rupture of the beads as well as guide the beads in an array. A device of this disclosure may comprise magnetic beads for either purpose. In one example, incorporation of $Fe_3O_4$ nanoparticles into polyelectrolyte containing beads triggers rupture in the presence of an oscillating magnetic field stimulus.

A bead may also be disrupted, dissolved, or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches result in a bead wall that may disintegrate or become more porous upon the application of a light trigger.

Figure 2:
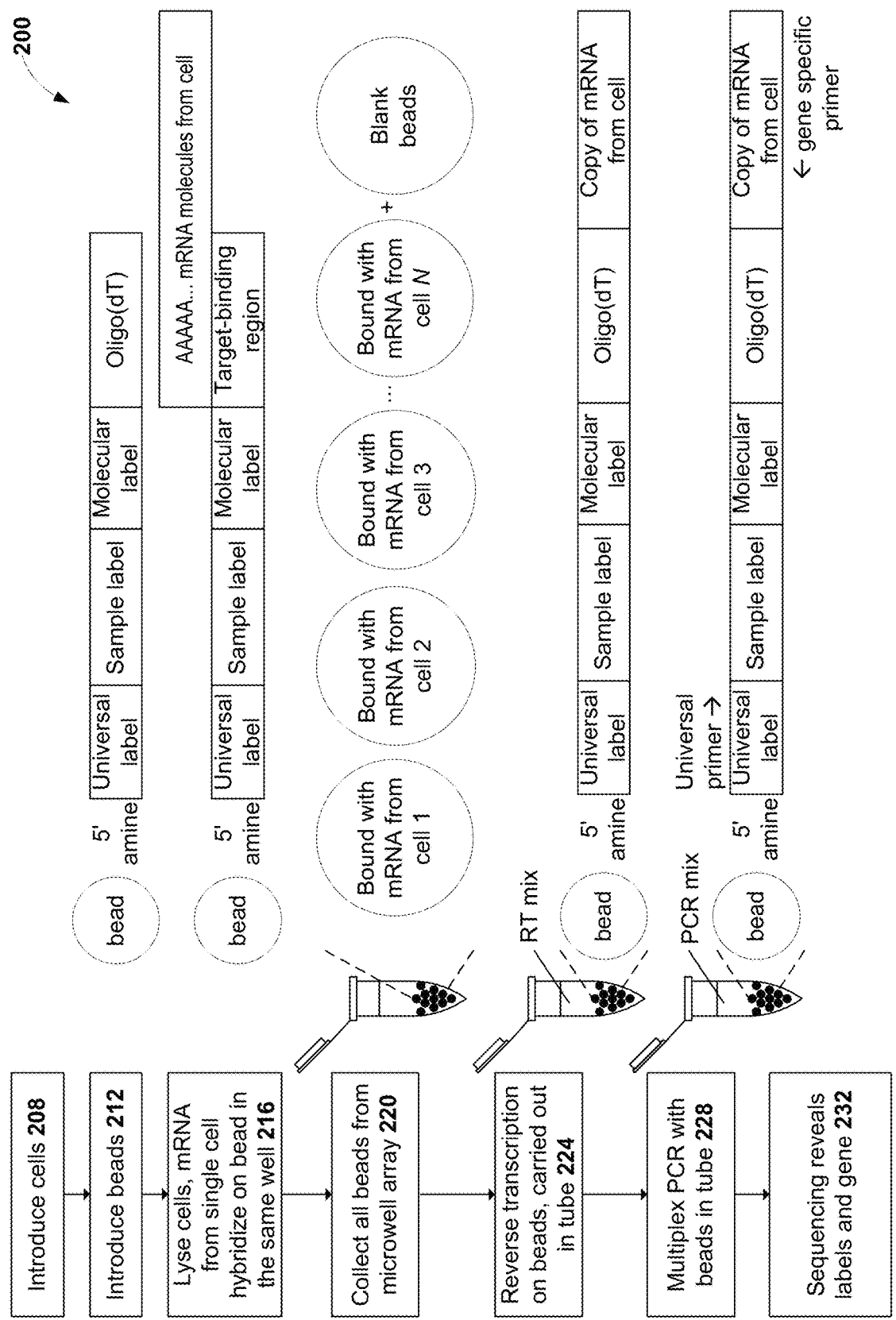
FIG. 2 shows a non-limiting exemplary workflow of barcoding and digital counting (e.g., stochastic barcoding and digital counting).

For example, in a non-limiting example of barcoding (e.g., stochastic barcoding) illustrated in FIG. 2, after introducing cells such as single cells onto a plurality of microwells of a microwell array at block 208, beads can be introduced onto the plurality of microwells of the microwell array at block 212. Each microwell can comprise one bead. The beads can comprise a plurality of barcodes. A barcode can comprise a 5' amine region attached to a bead. The barcode can comprise a universal label, a barcode sequence (e.g., a molecular label), a target-binding region, or any combination thereof.

The barcodes disclosed herein can be associated with (e.g., attached to) a solid support (e.g., a bead). The barcodes associated with a solid support can each comprise a barcode sequence selected from a group comprising at least 100 or 1000 barcode sequences with unique sequences. In some embodiments, different barcodes associated with a solid support can comprise barcode sequences of different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a bead). In some embodiments, stochastically barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate.

As used herein, the terms "tethered," "attached," and "immobilized" are used interchangeably, and can refer to covalent or non-covalent means for attaching barcodes to a solid support. Any of a variety of different solid supports can be used as solid supports for attaching pre-synthesized barcodes or for in situ solid-phase synthesis of barcodes.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g. magnesium, molybdenum, lithium, and tantalum), superparamagnetic materials (e.g. ferrite ($Fe_3O_4$; magnetite) nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

In some embodiments, the bead (e.g., the bead to which the labels are attached) is a hydrogel bead. In some embodiments, the bead comprises hydrogel.

Some embodiments disclosed herein include one or more particles (for example beads). Each of the particles can comprise a plurality of oligonucleotides (e.g., barcodes). Each of the plurality of oligonucleotides can comprise a barcode sequence (e.g., a molecular label), a cell label, and a target-binding region (e.g., an oligo(dT) sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% or more. In some embodiments, none of the plurality of the particles has the same cell label sequence.

The plurality of oligonucleotides on each particle can comprise different barcode sequences (e.g., molecular labels). In some embodiments, the number of barcode sequences can be, or about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of barcode sequences can be at least, or at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different barcode sequences. As another example, in a single particle, at least 100, 500, 1000, 5000, 10000, 15000, 20000, 50000, a number or a range between any two of these values, or more of the plurality of oligonucleotides comprise different barcode sequences. Some embodiments provide a plurality of the particles comprising barcodes. In some embodiments, the ratio of an occurrence (or a copy or a number) of a target to be labeled and the different barcode sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of the beads can vary. For example, the diameter of the bead can range from 0.1 micrometer to 50 micrometer. In some embodiments, the diameters of beads can be, or be about, 0.1, 0.5, 1, 2, 3, 4, 5, 6, 7, 8, 9, 10, 20, 30, 40, 50 micrometer, or a number or a range between any two of these values.

The diameters of the bead can be related to the diameter of the wells of the substrate. In some embodiments, the diameters of the bead can be, or be about, 10%, 20%, 30%, 40%, 50%, 60%, 70%, 80%, 90%, 100%, or a number or a range between any two of these values, longer or shorter than the diameter of the well. The diameter of the beads can be related to the diameter of a cell (e.g., a single cell entrapped by a well of the substrate). In some embodiments, the diameters of the bead can be at least, or at most, 10%, 20%, 30%, 40%, 50%, 60%, 70%, 80%, 90%, or 100% longer or shorter than the diameter of the well. The diameter of the beads can be related to the diameter of a cell (e.g., a single cell entrapped by a well of the substrate). In some embodiments, the diameters of the beads can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell. In some embodiments, the diameters of the beads can be at least, or at most, 10%, 20%, 30%, 40%, 50%, 60%, 70%, 80%, 90%, 100%, 150%, 200%, 250%, or 300% longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g. impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a barcode. A bead can change size, for example due to swelling in an organic or inorganic solution. A bead can be hydrophobic. A bead can be hydrophilic. A bead can be biocompatible.

A solid support (e.g., bead) can be visualized. The solid support can comprise a visualizing tag (e.g., fluorescent dye). A solid support (e.g., bead) can be etched with an identifier (e.g., a number). The identifier can be visualized through imaging the beads.

A solid support can comprise an insoluble, semi-soluble, or insoluble material. A solid support can be referred to as "functionalized" when it includes a linker, a scaffold, a building block, or other reactive moiety attached thereto, whereas a solid support may be "nonfunctionalized" when it lack such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

A solid support can be a biological molecule. For example a solid support can be a nucleic acid, a protein, an antibody, a histone, a cellular compartment, a lipid, a carbohydrate, and the like. Solid supports that are biological molecules can be amplified, translated, transcribed, degraded, and/or modified (e.g., pegylated, sumoylated, acetylated, methylated). A solid support that is a biological molecule can provide spatial and time information in addition to the spatial label that is attached to the biological molecule. For example, a biological molecule can comprise a first confirmation when unmodified, but can change to a second confirmation when modified. The different conformations can expose barcodes (e.g., stochastic barcodes) of the disclosure to targets. For example, a biological molecule can comprise barcodes that are inaccessible due to folding of the biological molecule. Upon modification of the biological molecule (e.g., acetylation), the biological molecule can change conformation to expose the barcodes. The timing of the modification can provide another time dimension to the method of barcoding of the disclosure.

In some embodiments, the biological molecule comprising barcode reagents of the disclosure can be located in the cytoplasm of a cell. Upon activation, the biological molecule can move to the nucleus, whereupon barcoding can take place. In this way, modification of the biological molecule can encode additional space-time information for the targets identified by the barcodes.

Substrates and Microwell Array

As used herein, a substrate can refer to a type of solid support. A substrate can refer to a solid support that can comprise barcodes and stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., bead). A microwell can comprise combinatorial barcode reagents of the disclosure.

Methods of Barcoding

The disclosure provides for methods for estimating the number of distinct targets at distinct locations in a physical sample (e.g., tissue, organ, tumor, cell). The methods can comprise placing the barcodes (e.g., stochastic barcodes) in close proximity with the sample, lysing the sample, associating distinct targets with the barcodes, amplifying the targets and/or digitally counting the targets. The method can further comprise analyzing and/or visualizing the information obtained from the spatial labels on the barcodes. In some embodiments, a method comprises visualizing the plurality of targets in the sample. Mapping the plurality of targets onto the map of the sample can include generating a two dimensional map or a three dimensional map of the sample. The two dimensional map and the three dimensional map can be generated prior to or after barcoding (e.g., stochastically barcoding) the plurality of targets in the sample. Visualizing the plurality of targets in the sample can include mapping the plurality of targets onto a map of the sample. Mapping the plurality of targets onto the map of the sample can include generating a two dimensional map or a three dimensional map of the sample. The two dimensional map and the three dimensional map can be generated prior to or after barcoding the plurality of targets in the sample. in some embodiments, the two dimensional map and the three dimensional map can be generated before or after lysing the sample. Lysing the sample before or after generating the two dimensional map or the three dimensional map can include heating the sample, contacting the sample with a detergent, changing the pH of the sample, or any combination thereof.

In some embodiments, barcoding the plurality of targets comprises hybridizing a plurality of barcodes with a plurality of targets to create barcoded targets (e.g., stochastically barcoded targets). Barcoding the plurality of targets can comprise generating an indexed library of the barcoded targets. Generating an indexed library of the barcoded targets can be performed with a solid support comprising the plurality of barcodes (e.g., stochastic barcodes).

Contacting a Sample and a Barcode

The disclosure provides for methods for contacting a sample (e.g., cells) to a substrate of the disclosure. A sample comprising, for example, a cell, organ, or tissue thin section, can be contacted to barcodes (e.g., stochastic barcodes). The cells can be contacted, for example, by gravity flow wherein the cells can settle and create a monolayer. The sample can be a tissue thin section. The thin section can be placed on the substrate. The sample can be one-dimensional (e.g., forms a planar surface). The sample (e.g., cells) can be spread across the substrate, for example, by growing/culturing the cells on the substrate.

When barcodes are in close proximity to targets, the targets can hybridize to the barcode. The barcodes can be contacted at a non-depletable ratio such that each distinct target can associate with a distinct barcode of the disclosure. To ensure efficient association between the target and the barcode, the targets can be crosslinked to the barcode.

Cell Lysis

Following the distribution of cells and barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g. SDS, Li dodecyl sulfate, Triton X-100, Tween-20, or NP-40), an organic solvent (e.g. methanol or acetone), or digestive enzymes (e.g. proteinase K, pepsin, or trypsin), or any combination thereof. To increase the association of a target and a barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 M or more Tris HCL. A lysis buffer can comprise about 0.1 M Tris HCl. The pH of the lysis buffer can be at least about 1, 2, 3, 4, 5, 6, 7, 8, 9, or 10 or more. The pH of the lysis buffer can be at most about 1, 2, 3, 4, 5, 6, 7, 8, 9, or 10 or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sulfate, triton X, tween, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7% or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7% or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Barcodes to Target Nucleic Acid Molecules

Following lysis of the cells and release of nucleic acid molecules therefrom, the nucleic acid molecules can randomly associate with the barcodes of the co-localized solid support. Association can comprise hybridization of a barcode's target recognition region to a complementary portion of the target nucleic acid molecule (e.g., oligo(dT) of the barcode can interact with a poly(A) tail of a target). The assay conditions used for hybridization (e.g. buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of barcoding illustrated in FIG. 2, at block 216, mRNA molecules can hybridize to barcodes on beads. For example, single-stranded nucleotide fragments can hybridize to the target-binding regions of barcodes.

Attachment can further comprise ligation of a barcode's target recognition region and a portion of the target nucleic acid molecule. For example, the target binding region can comprise a nucleic acid sequence that can be capable of specific hybridization to a restriction site overhang (e.g. an EcoRI sticky-end overhang). The assay procedure can further comprise treating the target nucleic acids with a restriction enzyme (e.g. EcoRI) to create a restriction site overhang. The barcode can then be ligated to any nucleic acid molecule comprising a sequence complementary to the restriction site overhang. A ligase (e.g., T4 DNA ligase) can be used to join the two fragments.

For example, in a non-limiting example of barcoding illustrated in FIG. 2, at block 220, the labeled targets from a plurality of cells (or a plurality of samples) (e.g., target-barcode molecules) can be subsequently pooled, for example, into a tube. The labeled targets can be pooled by, for example, retrieving the barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription

The disclosure provides for a method to create a target-barcode conjugate using reverse transcription (e.g., at block 224 of FIG. 2). The target-barcode conjugate can comprise the barcode and a complementary sequence of all or a portion of the target nucleic acid (i.e. a barcoded cDNA molecule, such as a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of the labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A)+ tail at the 3' end of mammalian mRNA. Random hexanucleotide primers can bind to mRNA at a variety of complementary sites. Target-specific oligonucleotide primers typically selectively prime the mRNA of interest.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions (e.g., at block 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cell label and/or barcode sequence (e.g., molecular label). The amplification reactions can comprise amplifying at least a portion of a sample tag, a cell label, a spatial label, a barcode (e.g., a molecular label), a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a barcode sequence (e.g., a molecular label).

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a labeled-amplicon (e.g., a stochastically labeled-amplicon). The labeled-amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a barcode sequence (e.g., a molecular label). The labeled-amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of labeled targets (e.g., stochastically labeled targets). The one or more primers can anneal to the 3' end or 5' end of the plurality of labeled targets. The one or more primers can anneal to an internal region of the plurality of labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a barcode sequence (e.g., a molecular label), a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and barcode sequence (e.g., molecular label) on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, barcoding (e.g., stochastically barcoding) the plurality of targets in the sample further comprises generating an indexed library of the barcoded fragments. The barcodes sequences of different barcodes (e.g., the molecular labels of different stochastic barcodes) can be different from one another. Generating an indexed library of the barcoded targets (e.g., stochastically barcoded targets) includes generating a plurality of indexed polynucleotides from the plurality of targets in the sample. For example, for an indexed library of the barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Stochastic barcoding can use nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, barcode sequences (e.g., molecular labels), and sequences of nucleotide fragments of the one or more copies of the targets, for example at block 232 of FIG. 2.

Figure 3:
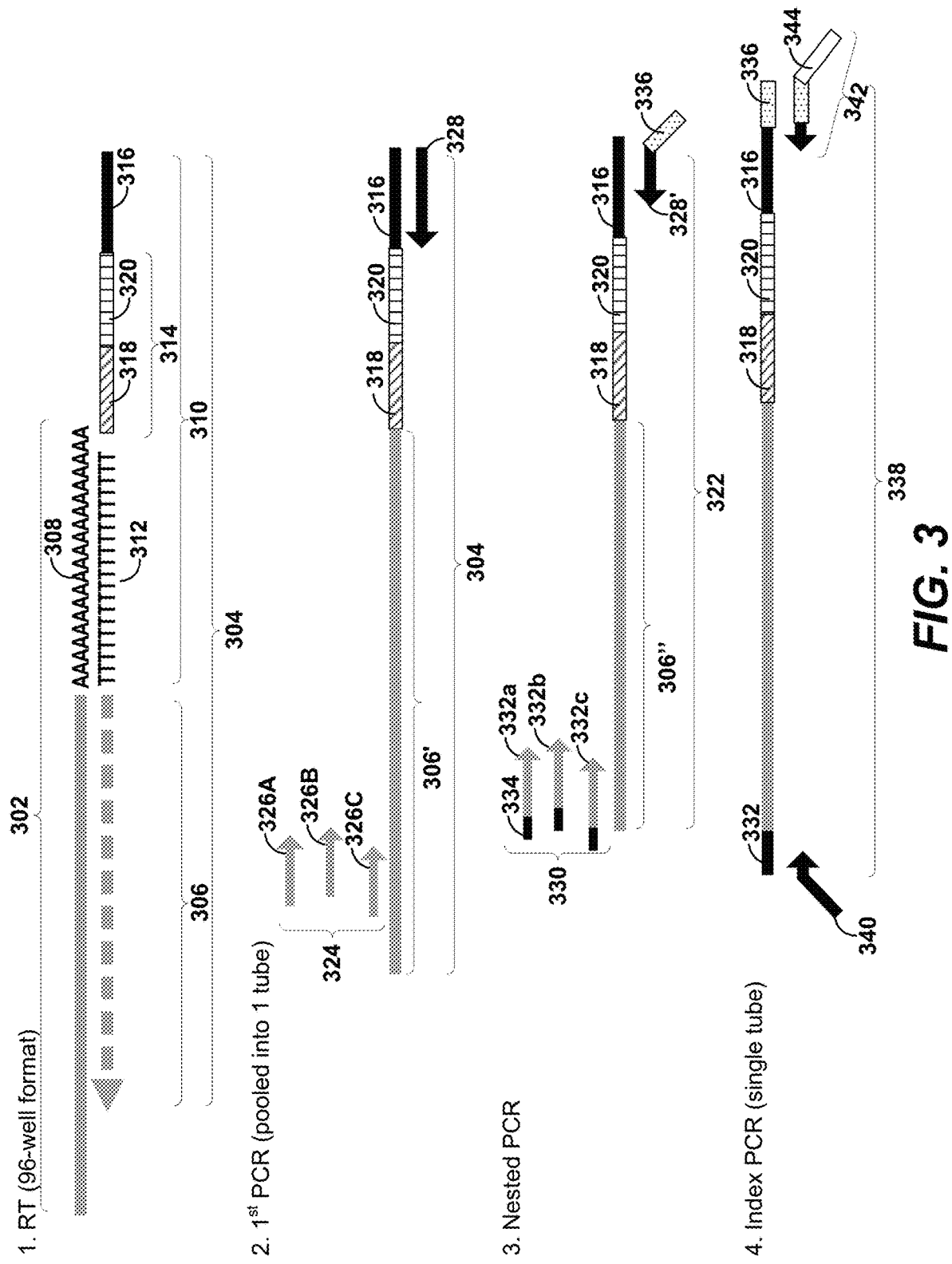
FIG. 3 is a schematic illustration showing a non-limiting exemplary process for generating an indexed library of the barcoded targets (e.g., stochastically barcoded targets) from a plurality of targets.

FIG. 3 is a schematic illustration showing a non-limiting exemplary process of generating an indexed library of the barcoded targets (e.g., stochastically barcoded targets), for example mRNAs. As shown in step 1, the reverse transcription process can encode each mRNA molecule with a unique barcode sequence (e.g., molecular label), a cell label, and a universal PCR site. For example, RNA molecules 302 can be reverse transcribed to produce labeled cDNA molecules 304, including a cDNA region 306, by the hybridization (e.g., stochastic hybridization) of a set of barcodes (e.g., stochastic barcodes) 310) to the poly(A) tail region 308 of the RNA molecules 302. Each of the barcodes 310 can comprise a target-binding region, for example a poly(dT) region 312, a barcode sequence or a molecular label 314, and a universal PCR region 316.

In some embodiments, the cell label can include 3 to 20 nucleotides. In some embodiments, the barcode sequence (e.g., molecular label) can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a barcode sequence or a molecular label 318 and a cell label 320. In some embodiments, the label region 314 can include one or more of a universal label, a dimension label, and a cell label. The barcode sequence or molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a barcode sequence or a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of barcodes or stochastic barcodes 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, barcodes or stochastic barcodes 310. And the set of barcodes or stochastic barcodes 310 can, for example, each contain a unique label region 314. The labeled cDNA molecules 304 can be purified to remove excess barcodes or stochastic barcodes 310. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise $1^{st}$ PCR primer pool 324 of custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a $2^{nd}$ universal PCR primer. Nested PCR can minimize PCR amplification bias. For example, the nested PCR labeled amplicons 322 can be further amplified by nested PCR. The nested PCR can comprise multiplex PCR with nested PCR primers pool 330 of nested PCR primers 332a-c and a $2^{nd}$ universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306" of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the $2^{nd}$ universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of barcodes or stochastic barcodes 310 can be sequenced in one sequencing reaction using next generation sequencing (NGS).

Errors in Cell Label Identification

Barcoding, such as stochastic barcoding, for example the Rhapsody™ assay (Cellular Research, Inc. (Palo Alto, Calif.)), can be based on beads. Molecules or targets such as mRNAs from different cells can hybridize to barcodes (e.g., stochastic barcodes) on different beads. Barcodes on different beads can have different cell labels, and barcodes on the same beads can have the cell labels. For example, a single cell and a single bead can be added to a microwell of a microwell plate such that prior to one bead is paired with one cell. Thus, cell labels are the same for all oligonucleotides on a bead, but differ between different beads, so that all molecules from one cell can be identified with the same cell label in the sequencing data. In some embodiments, the raw sequencing data from barcoding (e.g., stochastic barcoding) can include a higher number of cell labels than the number of cell input of the experiment. For example, some molecules of 1,000 cells can be barcoded (e.g., stochastically barcoded); however the raw sequencing data may indicate 20000-200000 cell labels.

The sources of the higher number of cell labels may be different in different implementations. Without being bound by any particular theory, it is believed that in some embodiments, cells paired with no bead can be lysed, and their nucleic acid contents can diffuse and associate with beads not paired with any cells to result in false cell label signals. In some embodiments, during the manufacturing process of the beads, the cell labels may have a mutation in them which converts one cell label into another cell label. In this case, molecules from the same cell can appear to be from two different cells (e.g., as if they were from two different beads because the cell label has mutated). Furthermore, substitution errors and non-substitution errors in the cell labels can occur during PCR amplification prior to sequencing. In some embodiments, exonuclease treatment (e.g., at steps 216 in FIG. 2), may not be efficient such that single stranded DNA on the bead can hybridize and form PCR chimeras during the PCR process.

If uncorrected, the excess numbers of cell labels in raw sequencing data can result in overestimated cell counts. Methods disclosed herein can separate or distinguish signal cell labels (also referred to as true cell labels) from noise cell labels.

Identifying a Cell Label as a Signal Cell Label or a Noise Cell Label Based on Second Derivatives Disclosed herein are methods for identifying a signal cell label. In some embodiments, the method comprises: (a) stochastically barcoding a plurality of targets in a sample of cells using a plurality of stochastic barcodes to create a plurality of stochastically barcoded targets, wherein each of the plurality of stochastic barcodes comprises a cell label and a molecular label; (b) obtaining sequencing data of the plurality of stochastically barcoded targets; (c) determining the number of molecular labels with distinct sequences associated with each of the cell labels of the plurality of stochastic barcodes; (d) determining a rank of each of the cell labels of the plurality of stochastic barcodes based on the number of molecular labels with distinct sequences associated with each of the cell labels; (e) generating a cumulative sum plot based on the number of molecular labels with distinct sequences associated with each of the cell labels determined in (c) and the rank of each of the cell labels determined in (d); (f) generating a second derivative plot of the cumulative sum plot; (g) determining a minimum of the second derivative plot of the cumulative sum plot, wherein the minimum of the second derivative plot corresponds to a cell label threshold; and (h) identifying each of the cell labels as a signal cell label (associated with a cell) or a noise cell label (not associated with cells) based on the number of molecular labels with distinct sequences associated with each of the cell labels determined in (c) and the cell label threshold determined in (g).

The cause of a noise cell label can be different in different implementations. In some embodiments, a noise cell label can arise from one or more PCR or sequencing errors. In some embodiments, a noise cell label can arise from RNA molecules being released from dead cells. In some embodiments, a noise cell label can arise from RNA molecules that are released from cells not associated with beads attaching to beads not associated with cells.

In some embodiments, the method comprises: (a) obtaining sequencing data of a plurality of barcoded targets (e.g., stochastically barcoded targets), wherein the plurality of barcoded targets is created from a plurality of targets in a sample of cells that are barcoded (e.g., stochastically barcoded) using a plurality of barcodes (e.g., stochastic barcodes), and wherein each of the plurality of barcodes comprises a cell label and a molecular label; (b) determining a rank of each of the cell labels of the plurality of barcoded targets (or barcodes) based on the number of molecular labels with distinct sequences associated with each of the cell labels of the plurality of barcoded targets (or barcodes); (c) determining a cell label threshold based on the number of molecular labels with distinct sequences associated with each of the cell labels and the rank of each of the cell labels of the plurality of barcoded targets (or barcodes) determined in (b); and identifying each of the cell labels as a signal cell label or a noise cell label based on the number of molecular labels with distinct sequences associated with each of the cell labels and the cell label threshold determined in (c).

Figure 4:
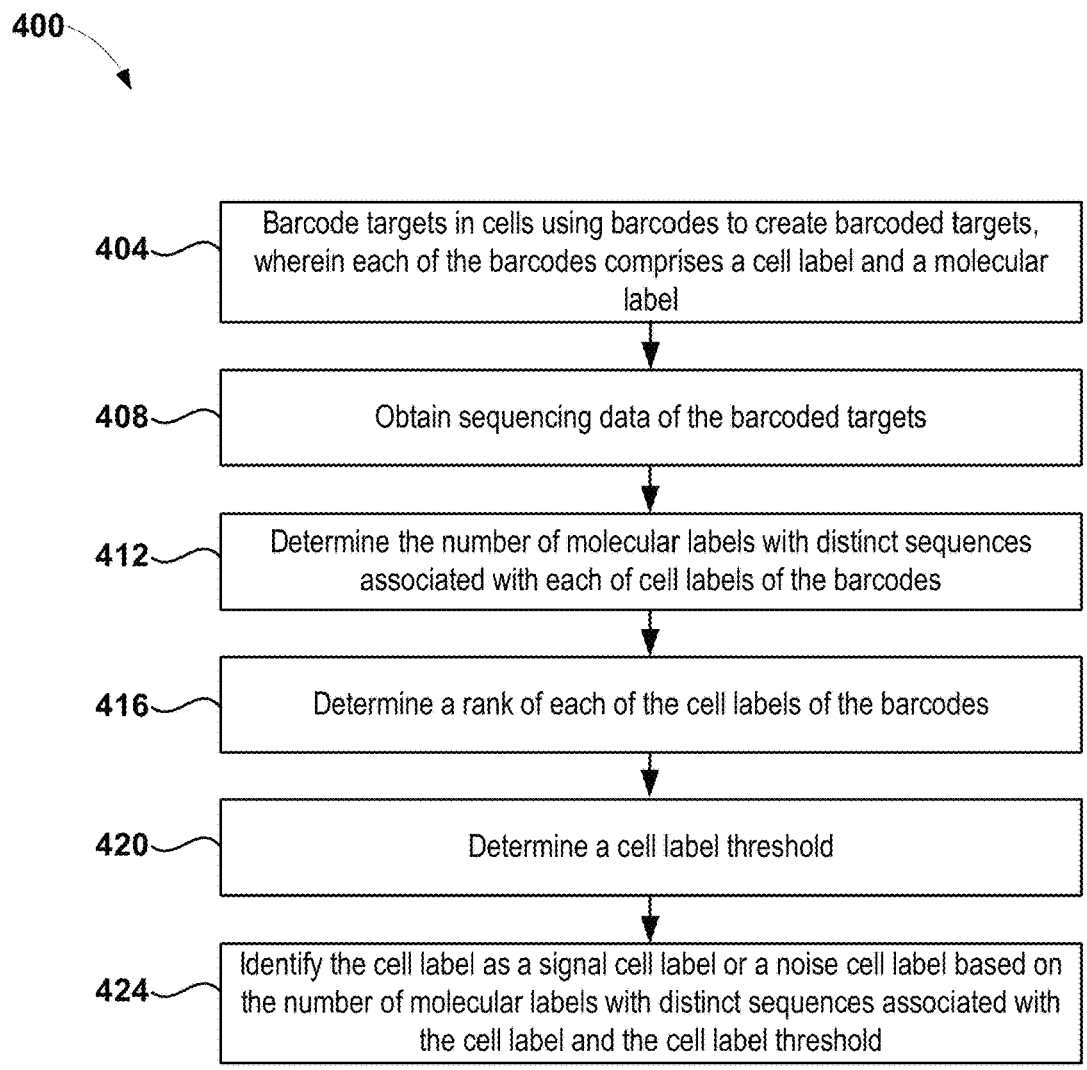
FIG. 4 is a flowchart showing a non-limiting exemplary method of identifying a cell as a signal cell label or a noise cell label.

FIG. 4 is a flowchart showing a non-limiting exemplary method 400 of identifying a cell as a signal cell label or a noise cell label. At block 404, the method 400 can optionally barcode (e.g., stochastically barcode) targets in cells using barcodes (e.g., stochastic barcodes) to create barcoded targets (e.g., stochastically barcoded targets) as described with reference to FIGS. 2-3. Each of the barcodes can comprise a cell label and a molecular label. Barcoded targets created from targets of different cells of the plurality of cells can have different cell labels. Barcoded targets created from targets of the same cell of the plurality of cells can have different molecular labels.

At block 408, the method 400 can obtain sequencing data of the barcoded targets (e.g., stochastically barcoded targets) as described herein in the section titled Sequencing. At block 412, the method 400 can optionally determine the number of molecular labels with distinct sequences associated with each of the cell labels of the barcodes (or barcoded targets). Determining the number of molecular labels with distinct sequences associated with each of the cell labels of the barcodes (or barcoded targets) can comprise: (1) counting the number of molecular labels with distinct sequences associated with the target in the sequencing data; and (2) estimating the number of the target based on the number of molecular labels with distinct sequences associated with the target in the sequencing data counted in (1). In some embodiments, the sequencing data obtained at block 408 includes the number of molecular labels with distinct sequences associated with each of the cell labels of the barcodes (or barcoded targets).

In some embodiments, the method can comprise removing sequencing information associated with molecular labels with distinct sequences associated with a target of the plurality of targets from the sequencing data obtained in at block 408 if the number of the molecular labels with distinct sequences associated with the target of the plurality of targets is above or below a molecular label occurrence threshold. The molecular label occurrence threshold can be different in different implementations. In some embodiments, the molecular label occurrence threshold can be, or be about, 1000, 2000, 3000, 4000, 5000, 6000, 7000, 8000, 9000, 10000, 20000, 30000, 40000, 50000, 60000, 70000, 80000, 90000, 100000, or a number or a range between any two of these values. In some embodiments, the molecular label occurrence threshold can be at least, or at most, 1000, 2000, 3000, 4000, 5000, 6000, 7000, 8000, 9000, 10000, 20000, 30000, 40000, 50000, 60000, 70000, 80000, 90000, or 100000. In some embodiments, the molecular label occurrence threshold can be, or be about, 1%, 2%, 3%, 4%, 5%, 6%, 8%, 9%, 10%, 20%, 30%, 40%, 50%, 60%, 80%, 90%, 91%, 92%, 93%, 94%, 95%, 96%, 97%, 98%, 99%, or a number or a range between any two of these values. In some embodiments, the molecular label occurrence threshold can be at least, or at most, 10%, 20%, 30%, 40%, 50%, 60%, 80%, 90%, 91%, 92%, 93%, 94%, 95%, 96%, 97%, 98%, or 99%.

At block 416, the method 400 can determine a rank of each of the cell labels of the barcodes (or barcoded targets). The rank of each of the cell labels of the barcodes (or barcoded targets) can be based on the number of molecular labels with distinct sequences associated with each of the cell labels of the plurality of barcodes (or barcoded targets).

At block 420, the method 400 can determine a cell label threshold associated with each of the cell labels of the plurality of barcodes (or barcoded targets) and the rank of each of the cell labels of the plurality of barcodes (or barcoded targets) determined at block 416. In some embodiments, determining the cell label threshold based on the number of molecular labels with distinct sequences associated with each of the cell labels of the plurality of barcodes (or barcoded targets) comprises: determining the cell label with the largest change in a cumulative sum for the cell label with a rank n and a cumulative sum for the cell label with the next rank n+1, wherein a number of molecular labels with distinct sequences associated with the cell label corresponds to the cell label threshold.

In some embodiments, determining the cell label threshold based on the number of molecular labels with distinct sequences associated with each of the cell labels of the plurality of barcodes (or barcoded targets) and the rank of each of the cell labels of the plurality of barcodes (or barcoded targets) determined at block 416 comprises: determining a cumulative sum for each rank of the cell labels, wherein the cumulative sum for the rank comprises a summation of a number of molecular labels with distinct sequences associated with each of the cell labels with a lower rank; and determining a rank n of the cell labels with the largest change in a cumulative sum for the rank n and a cumulative sum for the next rank n+1, wherein the rank n of the cell labels with the largest change in the cumulative sum and the cumulative sum for the next rank n+1 corresponds to the cell label threshold.

In some embodiments, determining the cell label threshold can comprise: generating a cumulative sum plot based on the number of molecular labels with distinct sequences associated with each of the cell labels and the rank of each of the cell labels determined in 416. Determining the cell label threshold can further comprise: generating a second derivative plot of the cumulative sum plot and determining a minimum of the second derivative plot of the cumulative sum plot. The minimum of the second derivative plot can correspond to the cell label threshold.

In some embodiments, generating the cumulative sum plot based on the number of molecular labels with distinct sequences associated with each of the cell labels and the rank of each of the cell labels determined at block 416 can comprise: determining a cumulative sum for each rank of the cell labels, wherein the cumulative sum for the rank comprises a summation of a number of molecular labels with distinct sequences associated with each of the cell labels with a lower rank. Generating the second derivative plot of the cumulative sum plot can comprise determining a difference between a cumulative sum of a first rank of the cell labels and a cumulative sum of a second rank of the cell labels over a difference between the first rank and the second rank. In some embodiments, the difference between the first rank and the second rank is one. The cumulative sum plot can be a log-log plot. The log-log plot can be a log 10-log 10 plot.

In some embodiments, the minimum is a global minimum. Determining the minimum of the second derivative plot can comprise determining a minimum of the second derivative plot above a threshold of a minimum number of molecular labels associated with each of the cell labels. The threshold of the minimum number of molecular labels associated with each of the cell labels can be a percentile threshold. The threshold of the minimum number of molecular labels associated with each of the cell labels can be determined based on the number of cells in the sample of cells. For example, the threshold of the minimum number of molecular labels associated with each of the cell labels can be greater if the number of cells in the sample of cells is greater.

The threshold of the minimum number of molecular labels associated with each of the cell labels can be different in different implementations. In some embodiments, the threshold of the minimum number of molecular labels associated with each of the cell labels can be, or be about, 1000, 2000, 3000, 4000, 5000, 6000, 7000, 8000, 9000, 10000, 20000, 30000, 40000, 50000, 60000, 70000, 80000, 90000, 100000, or a number or a range between any two of these values. In some embodiments, the threshold of the minimum number of molecular labels associated with each of the cell labels can be at least, or at most, 1000, 2000, 3000, 4000, 5000, 6000, 7000, 8000, 9000, 10000, 20000, 30000, 40000, 50000, 60000, 70000, 80000, 90000, or 100000. In some embodiments, the threshold of the minimum number of molecular labels associated with each of the cell labels can be, or be about, 1%, 10%, 20%, 30%, 40%, 45%, 50%, 60%, 80%, 90%, or a number or a range between any two of these values. In some embodiments, the molecular label occurrence threshold can be at least, or at most, 1%, 10%, 20%, 30%, 40%, 45%, 50%, 60%, 80%, or 90%.

In some embodiments, determining the minimum of the second derivative plot comprises determining a minimum of the second derivative plot below a threshold of a maximum number of molecular labels associated with each of the cell labels. The threshold of the maximum number of molecular labels associated with each of the cell labels can be a percentile threshold. The threshold of the maximum number of molecular labels associated with each of the cell labels can be determined based on the number of cells in the sample of cells. For example, the threshold of the maximum number of molecular labels associated with each of the cell labels can be greater if the number of cells in the sample of cells is greater.

The threshold of the maximum number of molecular labels associated with each of the cell labels can be different in different implementations. In some embodiments, the threshold of the maximum number of molecular labels associated with each of the cell labels can be, or be about, 1000, 2000, 3000, 4000, 5000, 6000, 7000, 8000, 9000, 10000, 20000, 30000, 40000, 50000, 60000, 70000, 80000, 90000, 100000, or a number or a range between any two of these values. In some embodiments, the threshold of the maximum number of molecular labels associated with each of the cell labels can be at least, or at most, 1000, 2000, 3000, 4000, 5000, 6000, 7000, 8000, 9000, 10000, 20000, 30000, 40000, 50000, 60000, 70000, 80000, 90000, or 100000. In some embodiments, the threshold of the maximum number of molecular labels associated with each of the cell labels can be, or be about, 10%, 20%, 30%, 40%, 45%, 50%, 60%, 80%, 90%, 91%, 92%, 93%, 94%, 95%, 96%, 97%, 98%, 99%, or a number or a range between any two of these values. In some embodiments, the molecular label occurrence threshold can be at least, or at most, 10%, 20%, 30%, 40%, 45%, 50%, 60%, 80%, 90%, 91%, 92%, 93%, 94%, 95%, 96%, 97%, 98%, or 99%.

At block 432, the method 400 can identify the cell label as a signal cell label or a noise cell label based on the number of molecular labels with distinct sequences associated with the cell label and the cell label threshold. Each of the cell labels is identified as the signal cell label if the number of molecular labels with distinct sequences associated with the each of the cell labels determined in (c) is greater than the cell label threshold. Each of the cell labels can be identified as a noise cell label if the number of molecular labels with distinct sequences associated with the each of the cell labels determined in (c) is not greater than the cell label threshold. In some embodiments, the method comprises removing, if a cell label of the plurality of barcodes (or barcoded targets) is identified as a noise cell label in 432, sequencing information associated with the identified cell label from the sequencing data obtained at block 408.

Identifying a Cell Label as a Signal Cell Label or a Noise Cell Label Based on Clustering Disclosed herein are methods for identifying a signal cell label. In some embodiments, the method comprises: (a) barcoding (e.g., stochastically barcoding) a plurality of targets in a sample of cells using a plurality of barcodes (e.g., stochastic barcodes) to create a plurality of barcoded targets (e.g., stochastically barcoded targets), wherein each of the plurality of barcodes comprises a cell label and a molecular label, wherein barcoded targets created from targets of different cells of the plurality of cells have different cell labels, and wherein barcoded targets created from targets of the same cell of the plurality of cells have different molecular labels; (b) obtaining sequencing data of the plurality of barcoded targets; (c) determining a feature vector of each cell label of the plurality of barcodes (or barcoded targets), wherein the feature vector comprise numbers of molecular labels with distinct sequences associated with the each cell label; (d) determining a cluster for the each cell label of the plurality of barcodes (or barcoded targets) based on the feature vector; and (e) identifying the each cell label of the plurality of barcodes (or barcoded targets) as a signal cell label or a noise cell label based on a number of cell labels in the cluster and a cluster size threshold.

Disclosed herein are methods for identifying a signal cell label. In some embodiments, the method comprises: (a) obtaining sequencing data of a plurality of barcoded targets (e.g., stochastically barcoded targets), wherein the plurality of barcoded targets (e.g., stochastically barcoded targets) is create from a plurality of targets in a sample of cells that are barcoded (e.g., stochastically barcoded) using a plurality of barcodes (e.g., stochastic barcodes), wherein each of the plurality of barcodes comprises a cell label and a molecular label, wherein barcoded targets created from targets of different cells of the plurality of cells have different cell labels, and wherein barcoded targets created from targets of the same cell of the plurality of cells have different molecular labels; (b) determining a feature vector of each cell label of the plurality of barcoded targets, wherein the feature vector comprise numbers of molecular labels with distinct sequences associated with the each cell label; (c) determining a cluster for the each cell label of the plurality of barcoded targets based on the feature vector; and (d) identifying the each cell label of the plurality of barcoded targets as a signal cell label or a noise cell label based on a number of cell labels in the cluster and a cluster size threshold.

Figure 5:
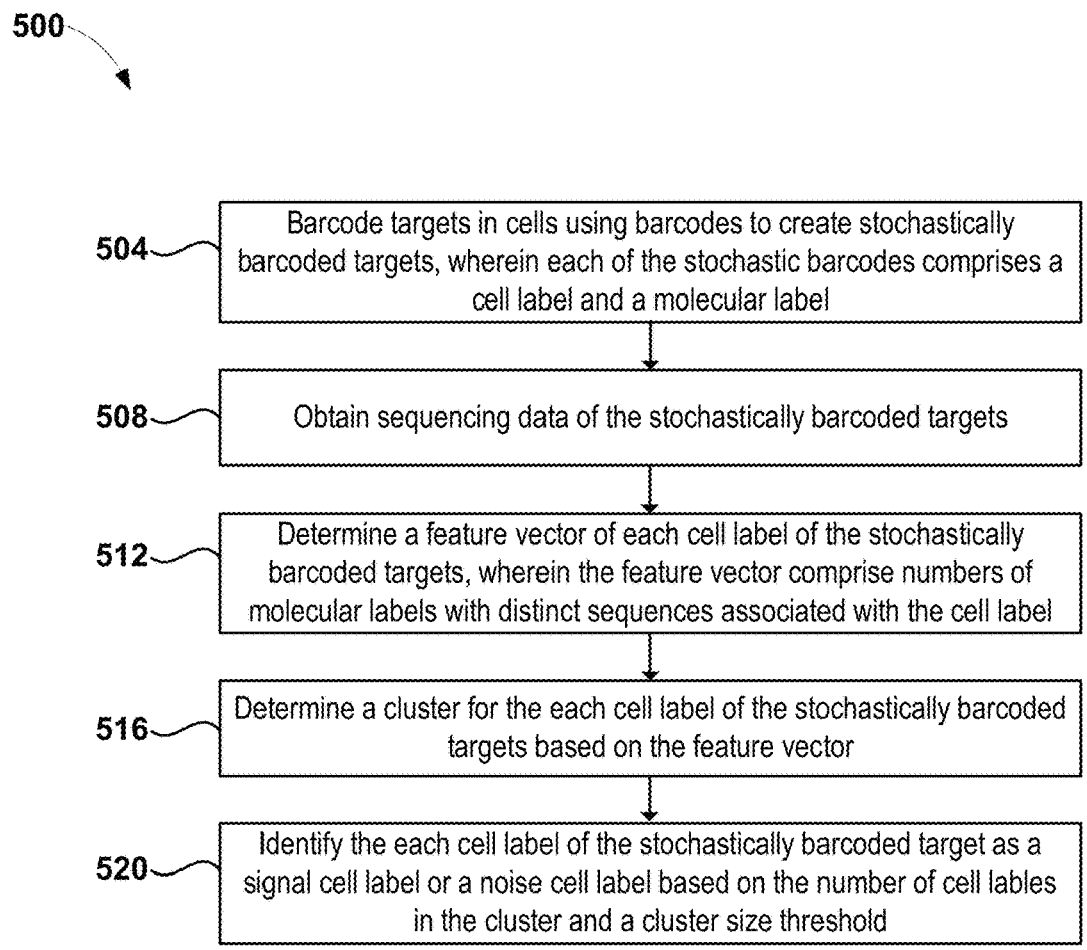
FIG. 5 is a flowchart showing another non-limiting exemplary method of identifying a cell as a signal cell label or a noise cell label.

FIG. 5 is a flowchart showing another non-limiting exemplary method of identifying a cell as a signal cell label or a noise cell label. At block 504, the method 500 can optionally barcode (e.g., stochastically barcode) targets in cells using stochastic barcodes to create barcoded targets (e.g., stochastically barcoded targets) as described with reference to FIGS. 2-3. Each of the barcodes comprises a cell label and a molecular label. Barcoded targets created from targets of different cells of the plurality of cells can have different cell labels. Barcoded targets created from targets of the same cell of the plurality of cells can have different molecular labels At block 508, the method 500 can obtain sequencing data of the barcoded targets. At block 508, the method 500 can optionally determine the number of molecular labels with distinct sequences associated with each of the cell labels of the barcodes (or barcoded targets). Determining the number of molecular labels with distinct sequences associated with each of the cell labels of the barcodes (or barcoded targets) can comprise: (1) counting the number of molecular labels with distinct sequences associated with the target in the sequencing data; and (2) estimating the number of the target based on the number of molecular labels with distinct sequences associated with the target in the sequencing data counted in (1). In some embodiments, the sequencing data obtained at block 508 includes the number of molecular labels with distinct sequences associated with each of the cell labels of the barcodes (or barcoded targets).

At block 512, the method 500 can determine a feature vector of the cell label. The feature vector can comprise the numbers of the molecular labels with distinct sequences associated with the cell label. For example, each element of the feature vector can comprise a number of a molecular label associated with the cell label. As another example, one element of the feature vector can comprise a number of a molecular label associated with the cell label, and another element of the feature vector can comprise a number of another molecular label associated with the cell label.

At block 516, the method 500 can determine a cluster for the cell label based on the feature vector. In some embodiments, determining the cluster for the each cell label of the plurality of barcodes (or barcoded targets) based on the feature vector comprises clustering the each cell label of the barcodes (or barcoded targets) into the cluster based on a distance of the feature vector to the cluster in a feature vector space. Determining the cluster for the each cell label of the plurality of barcoded targets based on the feature vector comprises: projecting the feature vector from a feature vector space into a lower dimensional space; and clustering the each cell label into the cluster based on a distance of the feature vector to the cluster in the lower dimensional space. The lower dimensional space can be a two dimensional space.

In some embodiments, projecting the feature vector from the feature vector space into the lower dimensional space comprises projecting the feature vector from the feature vector space into the lower dimensional space using a t-distributed stochastic neighbor embedding (tSNE) method. Clustering the each cell label into the cluster based on the distance of the feature vector to the cluster in the lower dimensional space can comprise clustering the each cell label into the cluster based on the distance of the feature vector to the cluster in the lower dimensional space using a density-based method. The density-based method can comprises a density-based spatial clustering of applications with noise (DBSCAN) method.

At block 520, the method 500 can identify the cell label as a signal cell label or a noise cell label based on the number of the cells in the cluster and a cluster size threshold. In some embodiments, the cell label can be identified as the signal cell label if the number of cell labels in the cluster is below the cluster size threshold. The cell label can be identified as a noise cell label if the number of cell labels in the cluster is not below the cluster size threshold.

In some embodiments, the method comprises determining the cluster size threshold based on the number of cell labels of the plurality of barcodes (or barcoded targets). The cluster size threshold can be a percentage of the number of cell labels of the plurality of barcoded targets. In some embodiments, determining the cluster size threshold based on the number of cell labels of the plurality of barcodes (or barcoded targets). The cluster size threshold can be a percentage of the number of cell labels of the plurality of barcodes (or barcoded targets). In some embodiments, the method comprises determining the cluster size threshold based on numbers of molecular labels with distinct sequences associated with each cell label of the plurality of barcodes (or barcoded targets).

Distinguishing Cell Labels Associated with True Cells from Noise Cells

Disclosed herein are embodiments of a method for reliably distinguishing between labels (e.g., cell labels) associated with true cells and noise cells. Cell labels associated with true cells are referred to herein as signal cell labels. Noise cells are referred to herein as noise cell labels. The method may detect or identify most of the true cells (or signal cell labels) corresponding to different cell types/clusters in some embodiments. The method may be able to automatically eliminate noise cells that are low expressers within certain cell types, such as monocytes and plasma.

Figure 6A:
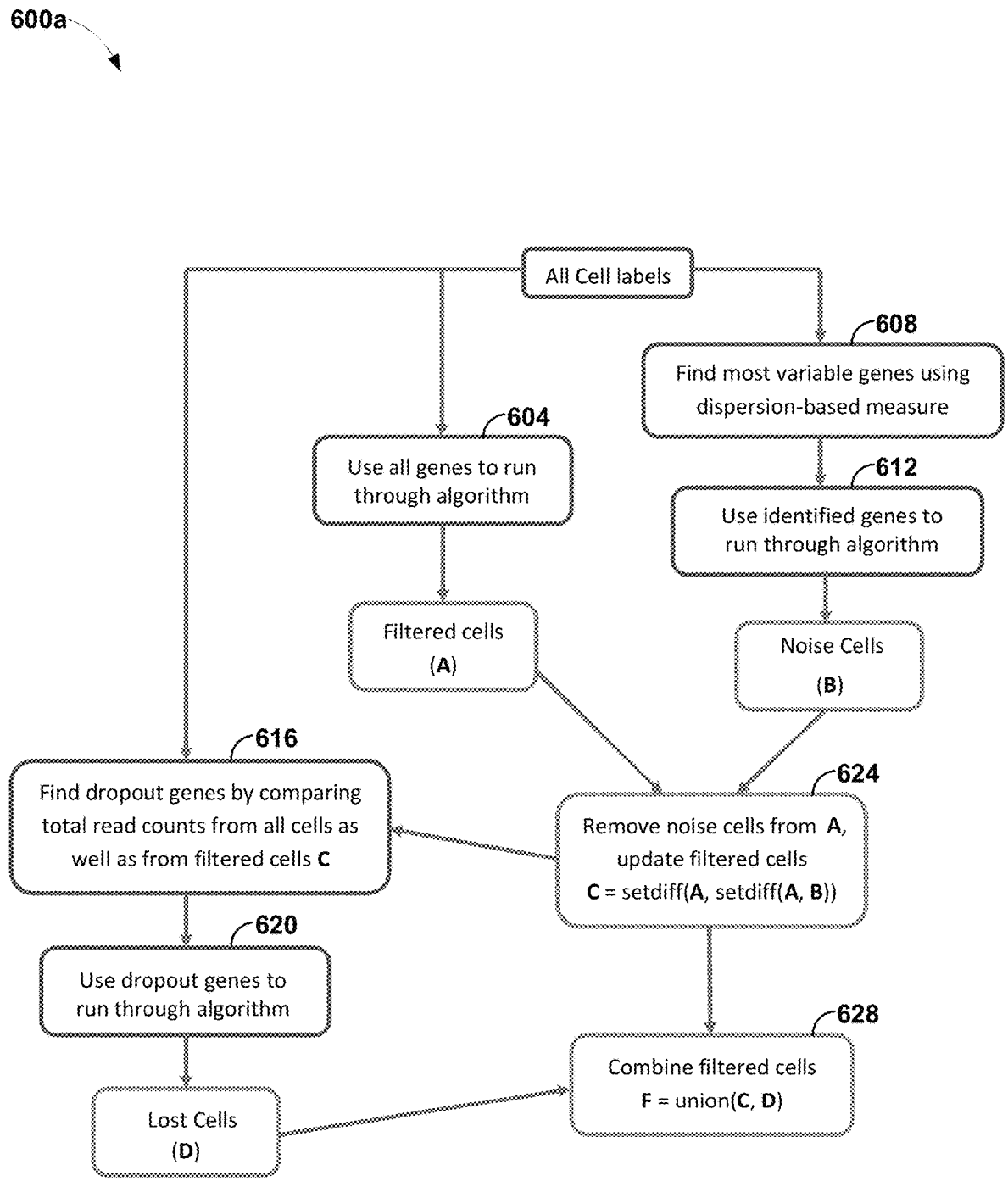
FIG. 6A is a flow diagram showing a non-limiting exemplary method for distinguishing labels associated with true cells from noise cells.

FIG. 6A is a flow diagram showing a non-limiting exemplary method 600a for distinguishing labels associated with true cells from noise cells. The method 600a can be based on one or more cell label identification or classification methods (e.g., the method 400 or 500 described with reference to FIG. 4 or 5). The method 600a can improve on these cell label identification methods in some embodiments. The method can be used for classifying cell labels in the Rhapsody™ pipeline.

The method 600a comprises multiple steps or actions. At block 604, the method 600a includes performing (or running) a cell label identification method (e.g., the method 400 or 500 described with reference to FIG. 4 or 5) to determine a plurality of true cells (or signal cell labels, referred to as filtered cells (A) in FIG. 6). For example, the cell label identification method can be based on a log 10-transformed cumulative reads curve. The cell label identification method can be used to determine the inflection point where the curve starts to level off. For example, the major inflection point can be the separation between true cells and noise cells.

The method 600a can include removing noise cells by, for example, restricting to genes that are highly variable (e.g., most variable) across a majority of cells (e.g., all cells) and performing a cell label identification method. For example, the method 600a can include re-running the cell label identification method, run at block 604, on most variable genes across all cells. The method 600a can include identifying highly variable genes across a majority of cells (e.g., all cells) at block 608. A cell label identification method can be performed, at block 612, on the most variable genes identified at block 608 to determine one or more true cells (or signal cell labels, where are referred to as noise cells (B) in FIG. 6). To identify the highly variable genes, the method 600a can optionally include: log-transforming read counts of each gene within each cell (e.g., the number of molecular labels with distinct sequences associated of each gene for each cell label) to determine a gene expression. For example, a read count can be log-transformed using Equation [1] below.

$$\log 10(\text{count}+1) \qquad \text{Eq. [1]}$$

At block 608, the method 600a can include: determining one or more measures or indications of the expression of each gene, such as the average expression (or maximum, median, or minimum expression) and dispersion (e.g., variance/mean). The method 600a can include: assigning each gene (or expression profile of each gene) into one of a plurality of bins. For example, genes can be assigned into 20 bins based on each gene's average (or maximum, median, or minimum) expression. The number of bins can be different in different implementations. In some embodiments, the number of bins can be, or be about, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 300, 400, 500, 600, 700, 800, 900, 1000, or a number or a range between any two of these values. In some embodiments, the number of bins can be at least, or at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 300, 400, 500, 600, 700, 800, 900, or 1000.

At block 608, the method 600a can include: within each bin, determining one or more measures or indications of the dispersion measures of all genes. For example, the mean and standard deviation (STD) of the dispersion measure of all genes can be determined. The method 600a can include determining the normalized dispersion measure of each gene using, for example, Equation [2].

$$\text{Normalized dispersion}=(\text{dispersion}-\text{mean})/\text{standard deviation} \qquad \text{Eq. [2]}$$

At block 608, the method 600a can include: applying one or more different cutoff values to the normalized dispersion to identify genes whose expression values are highly variable (e.g., with a variability above a threshold) even when compared to genes with similar average expression. The number of cutoff values can be different in different implementations. In some embodiments, the number of cutoff values can be, or be about, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 300, 400, 500, 600, 700, 800, 900, 1000, or a number or a range between any two of these values. In some embodiments, the number of cutoff values can be at least, or at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 300, 400, 500, 600, 700, 800, 900, or 1000.

Figure 7:
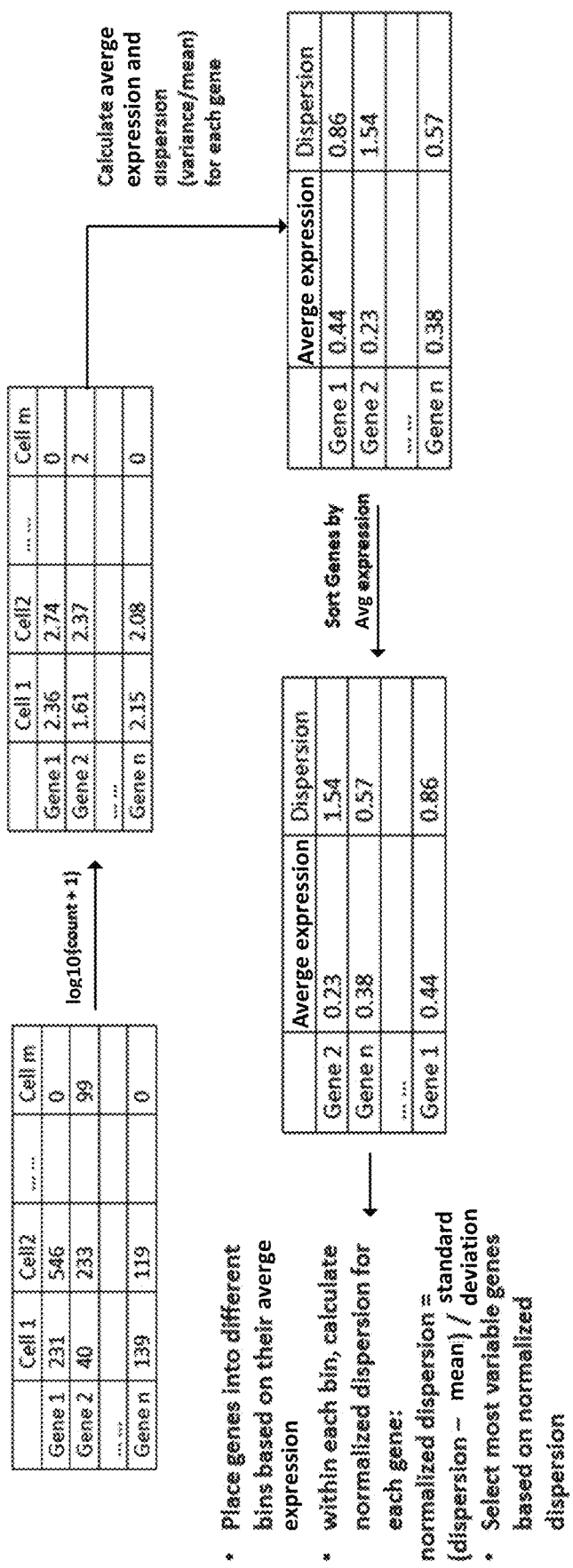
FIG. 7 is a non-limiting exemplary schematic illustration showing identification of the most variable genes. A method for distinguishing labels associated with true cells from noise cells (e.g., the method 600a described with reference to FIG. 6A, illustrated in Example 4) can include identification of the most variable genes.

In some embodiments, the method 600a can determine a cell as a noise cell (or a cell label or a noise cell label) if, or only if, the cell is identified as a noise cell in a threshold number of cutoff values or a threshold percentage of all cutoff values (e.g., a minority, a majority, or all cutoff values). In some embodiments, the threshold number of cutoff values can be, or be about, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 300, 400, 500, 600, 700, 800, 900, 1000, or a number or a range between any two of these values. In some embodiments, the threshold number of cutoff values can be at least, or at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 300, 400, 500, 600, 700, 800, 900, or 1000. In some embodiments, the threshold percentage of all cutoff values can be, or be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, 100%, or a number or a range between any two of these values. In some embodiments, the threshold percentage of all cutoff values can be at least, or at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or 100%. In some embodiments, such noise cell identification can improve the accuracy of the noise cells identified (e.g., decrease the possibility of identifying a true cell as a noise cell). FIG. 7 is a non-limiting exemplary schematic illustration showing identification of the most variable genes.

Referring to FIG. 6A, at block 616, the method 600a can include: determining or identifying true cells (or signal cell labels) that may be mis-determined (e.g., not identified) at block 604, for example, by determining if there are any dropout genes. If so, the method 600a can include, at block 620, running or re-running a cell label identification method (e.g., the cell label identification method used at block 604 or 612) to determine one or more lost true cells (or lost signal cell labels) not identified at block 604. The lost true cells determined at block 620 are referred to as lost cells (D) in FIG. 6A. Identifying dropout genes can include: for each gene, determining the total read counts from all cells as well as from the clean-up cells determined at block 625. The clean-up cells can be determined using Equation [3a] or Equation [3b], where C denotes the clean-up cells, A denotes the filtered or true cells determined at block 604, and B denotes lose cells determined at block 612.

$$C=\text{set\_difference}(A,\text{set\_difference}(A,B)) \quad \text{Eq. [3a]}$$

$$C=A-(A-B) \quad \text{Eq. [3a]}$$

Figure 8B:
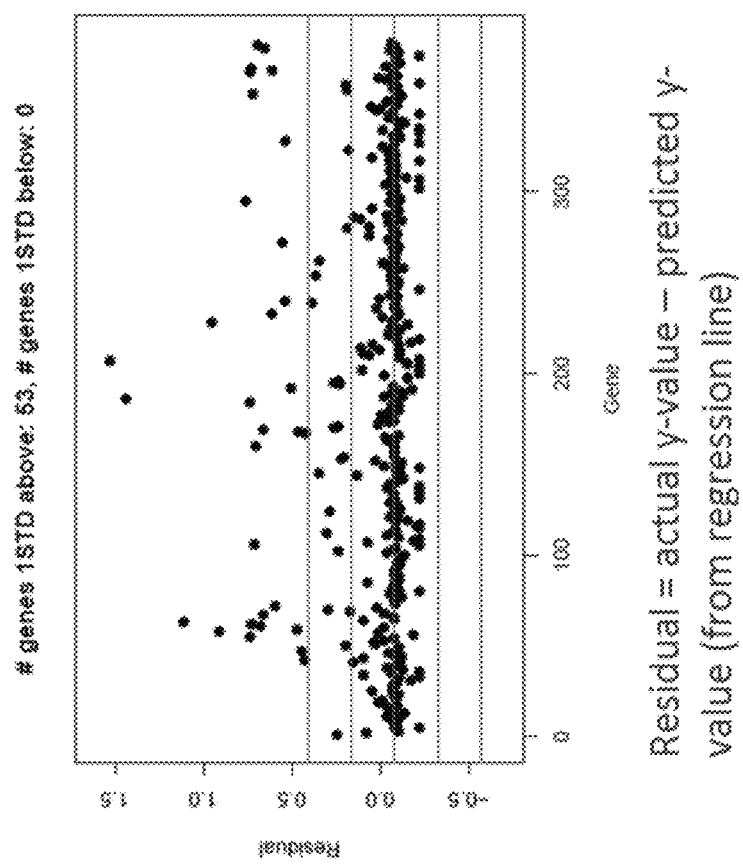
FIGS. 8A-8B are non-limiting exemplary plots illustrating identification of genes with biggest lose in the number of molecular labels with distinct sequences associated for each gene. A method for distinguishing labels associated with true cells from noise cells (e.g., the method 600a described with reference to FIG. 6A, illustrated in Example 4) can include identification of genes with biggest lose in the number of molecular labels associated with distinct sequences for each gene.
Figure 8A:
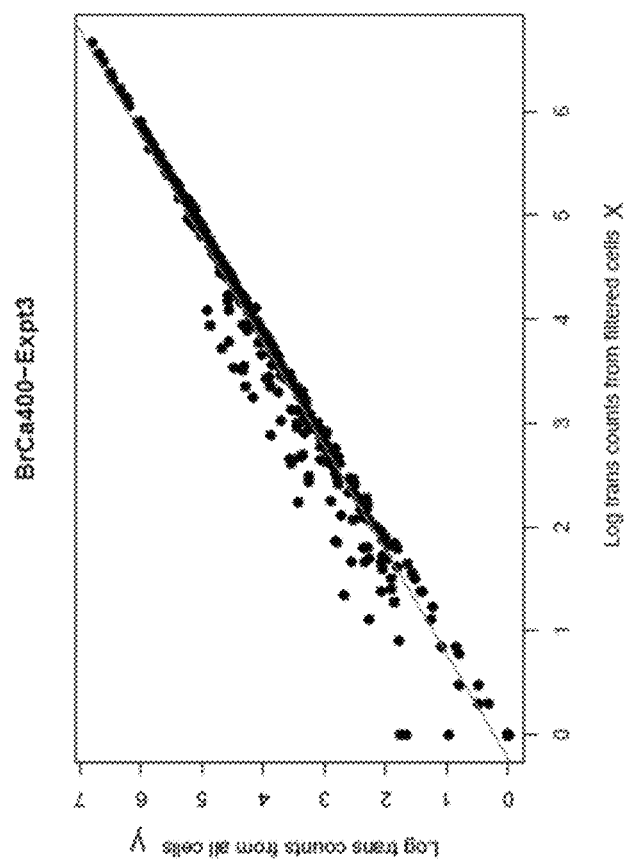

Identifying dropout genes can include: identifying the genes that have big loses (e.g., the biggest lose) in the count from clean-up cells compared to the count from all cells. For example, the genes with biggest loss can be determined by plotting total counts, and finding the best line of fit to determining the genes with large residuals (e.g., the largest residuals), such as at least one a threshold number of standard deviation away from the median of residuals of all genes (see FIGS. 8A-8B). The median can be used instead of the mean to minimize the impact of outliers in some embodiments. The threshold number of standard deviation can be different in different implementations. In some embodiments, the threshold number of standard deviation can be, or be about, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, or a number or a range between any two of these values. In some embodiments, the threshold number of standard deviation can be at least, or at most, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, or 10.

At block 624, the method 600a can include combining the cells (or cell labels) identified at block 620 and block 624 to determine a final set of true cells (referred to as filtered cells F in FIG. 6).

Figure 6B:
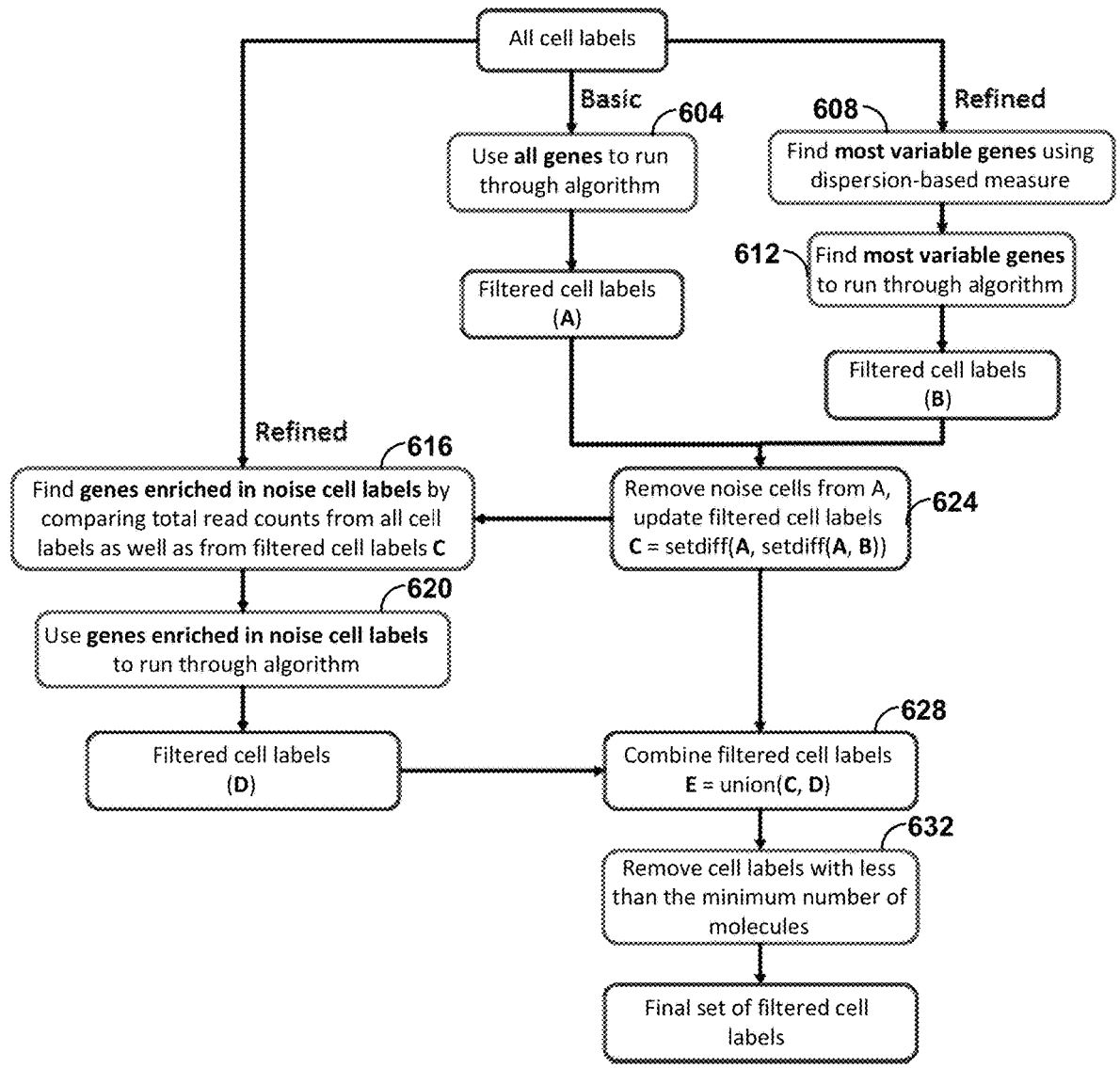
FIG. 6B is a flow diagram showing another non-limiting exemplary method for distinguishing labels associated with true cells from noise cells.

FIG. 6B is a flow diagram showing another non-limiting exemplary method 600b for distinguishing labels associated with true cells from noise cells. Actions performed at blocks 604-628 in FIG. 6B can be similar to the actions performed at corresponding blocks of method 600a described with reference to FIG. 6A. The method 600b can include, running an algorithm based on log 10-transformed cumulative reads curve and find the inflection point where the curve starts to level off at block 604. The major inflection point is the separation between cells and noise. The method 600b can include one or more of the following steps. Start from all cells, get the most variable genes using z-score cutoff of dispersion measure of genes. Focus on the most variable genes only and run through current algorithm to infer true cells, denote this set as B. Determine cells detected by other cell label identification methods using all genes in the panel but not detected by the algorithm using the most variable genes only, i.e. setdiff(A, B), are determined as noise cells. In some embodiments, to be more conservative, try multiple dispersion z-cutoff values, and determine a cell as noise only if the cell is classified as noise for some, a majority, or all cutoff values. Remove the noise cells from set A and get an updated cell set, using Equation [3a] or [3b] above.

The method 600b can include removing noise cells by restricting to genes that are most variable or highly variable across all cells, at block 608, and re-running the algorithm (e.g., run at block 604) at block 612. For example, the method can include one or more of the following steps. Retrieve true cells. For each gene, calculate the total read counts of all cells as well as from cells in set C. Find the genes that are mostly dropped out in the set C. Focus on the dropped out genes and run through the method run at block 604 to retrieve any true cells that may get lost, denote cells identified in this step as D.

The method 600b can include recovering true cells that may be mis-detected or mis-determined at block 604 by checking if there are any dropout genes at block 616. If so, the method 600b can include restricting to the dropped out genes (also referred to as under-represented genes) and re-running the algorithm (e.g., run at block 604) to pick up the lost true cells at block 620. The final list of cells, F, can be determined using Equation [4].

$$F=\text{union}(C,D) \quad \text{Equation [4]}$$

In some embodiments, at block 632, cells from block 628 can be cleaned up or polished by removing cells that do not carry high enough number of molecules. For example, the minimum threshold of the molecule count can be determined by the following rules. Step (a) Find a big gap (e.g., the biggest gap, the second biggest gap, the third biggest gap, etc.) in the total molecule counts of the cells lying at the bottom quarter, and determine the cutoff as the value of the gap. Step (b) Find the cells with molecule counts less than the cutoff determined at step (a), and, optionally, calculate the percent of cells removed due to low molecule count. Step (c) Under one or both of the following two conditions, do not use the adaptive cutoff determined above, but rather use the fixed cutoff of, for example, 20 molecules: condition (i) percent of cells removed due to low molecule count is greater than, or at least, a threshold percentage (e.g., 20%) and/or the gap is less than a threshold number (e.g., 500); and condition (ii) the biggest gap in the total molecule count of all cells is, for example, 1. The cells after the clean-up are part of the final set of filtered cells detected by the method 600b.

The fixed cutoff at step (c) can be different in different implementations. In some embodiments, the cutoff can be, or be about, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, or a number or a range between any two of these values. In some embodiments, the cutoff can be at least, or at most, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100. The threshold percentage in condition (i) can be different in different implementations. In some embodiments, the threshold percentage can be, or be about, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or a number or a range between any two of these values. In some embodiments, the threshold percentage can be at least, or at most, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%. The threshold number of the gap in condition (i) can be different in different implementations. In some embodiments, threshold number of gap can be, or be about, 50, 100, 150, 200, 250, 300, 350, 400, 450, 500, 550, 600, 650, 700, 750, 800, 850, 900, 950, 1000, or a number or a range between any two of these values. In some embodiments, threshold number of gap can be at least, or at most, 50, 100, 150, 200, 250, 300, 350, 400, 450, 500, 550, 600, 650, 700, 750, 800, 850, 900, 950, 1000, or a number or a range between any two of these values. The biggest gap in condition (ii) can be different in different implementations. In some embodiments, the biggest gap can be, or be about, 1, 2, 3, 4, 5, 6, 7, 8, 9, 10, 20, 30, 40, 50, 60, 70, 80, 90, 100, or a number or a range between any two of these values. In some embodiments, the biggest gap can be at least, or at most, 1, 2, 3, 4, 5, 6, 7, 8, 9, 10, 20, 30, 40, 50, 60, 70, 80, 90, or 100.

Disclosed herein are embodiments of a method for identifying a signal cell label. In some embodiments, the method comprises: (a) obtaining sequencing data of a plurality of first targets of cells, wherein each first target is associated with a number of molecular labels with distinct sequences associated with each cell label of a plurality of cell labels; (b) identifying each of the cell labels as a signal cell label or a noise cell label based on the number of molecular labels with distinct sequences associated with each of the cell labels and an identification threshold, such as at block 604 of method 600a or 600b, using the method 400 or 500; and (c) re-identifying at least one of the plurality of cell labels as a signal cell label identified as a noise cell label in (b), such as blocks 608, 612 of method 600a or 600b, using the method 400 or 500, or re-identifying at least one of the cell label as a noise cell label identified as a signal cell label in (b), such as blocks 616, 620 of the method 600a or 600b, using the method 400 or 500. Identifying each of the cell labels, re-identifying at least one of the plurality of cells labels as a signal cell label, or re-identifying at least one of the plurality of cell labels as a noise cell label can be based on an identical cell label identification method or different cell label identification methods of the disclosure (such as the method 400 or 500 described with reference to FIG. 4 or FIG. 5). The identification threshold can comprise a cell label threshold, a cluster size threshold, or any combination thereof. The method can comprise: removing one or more cell labels of the plurality of cell labels each associated with a number of molecular labels with distinct sequences below threshold of a number of molecular labels, such as at block 628 of method 600b described with reference to FIG. 6A.

In some embodiments, re-identifying at least one of the plurality of cell labels as a signal cell label identified as a noise cell label in (b) comprises: determining a plurality of second targets of the plurality of first targets each with one or more variability indications, amongst the plurality of first targets, above a variability threshold, such as at block 608 of the method 600a or 600b; and re-identifying at least one of the plurality of cell labels as a signal cell label identified as a noise cell label in (b) based on, for each of the plurality of cell labels, the number of molecular labels with distinct sequences associated with the plurality of second targets and the identification threshold, such as at block 612 of the method 600a or 600b. The one or more variability indications of the second target can comprise an average, a maximum, a median, a minimum, a dispersion, or any combinations thereof, of the numbers of molecular labels with distinct sequences associated with the second target and cell labels of the plurality of cell labels in the sequencing data. The one or more variability indications of the second target can comprise a standard deviation, a normalized dispersion, or any combinations thereof, variability indications of a subset of the plurality of second targets. The variability threshold can be smaller than or equal to the size of the subset of the plurality of second targets.

In some embodiments, re-identifying at least one of the plurality of cell labels as a noise cell label identified as a signal cell label in (b) comprises: determining a plurality of third targets of the plurality of first targets each with an association with cell labels identified as noise cell labels in (c) above an association threshold, such as at block 616 of the method 600a or 600b; and re-identifying at least one of the cell label as a noise cell label identified as a signal cell label in (b), for each of the plurality of cell labels, based on the number of molecular labels with distinct sequences associated with the plurality of third targets, and the identification threshold, such as at block 620 of the method 600a or 600b. Determining the plurality of third targets of the plurality of first targets each with an association with cell labels identified as noise cell labels in (c) above the association threshold can comprise: determining a plurality of remaining cells labels identified as signal cell labels after re-identifying at least one of the cell label as a signal cell label identified as a noise cell label in (b); determining the plurality of third targets based on for each of the plurality of cell labels, the number of molecular labels with distinct sequences associated with the plurality of targets, and for each of the plurality of remaining cell labels, the number of molecular labels with distinct sequences associated with the plurality of targets.

Sequencing

In some embodiments, estimating the number of different barcoded targets (e.g., stochastically barcoded targets) can comprise determining the sequences of the labeled targets, the spatial label, the molecular label, the sample label, the cell label, or any product thereof (e.g. labeled-amplicons, or labeled-cDNA molecules). An amplified target can be subjected to sequencing. Determining the sequence of a barcoded target (e.g., a stochastically barcoded target) or any product thereof can comprise conducting a sequencing reaction to determine the sequence of at least a portion of a sample label, a spatial label, a cell label, a molecular label, at least a portion of the labeled target (e.g., stochastically labeled target), a complement thereof, a reverse complement thereof, or any combination thereof.

Determination of the sequence of a barcoded target or a stochastically barcoded target (e.g. amplified nucleic acid, labeled nucleic acid, cDNA copy of a labeled nucleic acid, etc.) can be performed using variety of sequencing methods including, but not limited to, sequencing by hybridization (SBH), sequencing by ligation (SBL), quantitative incremental fluorescent nucleotide addition sequencing (QIF-NAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads, wobble sequencing, multiplex sequencing, polymerized colony (POLONY) sequencing; nanogrid rolling circle sequencing (ROLONY), allele-specific oligo ligation assays (e.g., oligo ligation assay (OLA), single template molecule OLA using a ligated linear probe and a rolling circle amplification (RCA) readout, ligated padlock probes, or single template molecule OLA using a ligated circular padlock probe and a rolling circle amplification (RCA) readout), and the like.

In some embodiments, determining the sequence of the barcoded target (e.g., stochastically barcoded target) or any product thereof comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of the barcoded target or any product thereof can be determined by electron microscopy or a chemical-sensitive field effect transistor (chemFET) array.

High-throughput sequencing methods, such as cyclic array sequencing using platforms such as Roche 454, Illumina Solexa, ABI-SOLiD, ION Torrent, Complete Genomics, Pacific Bioscience, Helicos, or the Polonator platform, can be utilized. In some embodiment, sequencing can comprise MiSeq sequencing. In some embodiment, sequencing can comprise HiSeq sequencing.

The labeled targets (e.g., stochastically labeled targets) can comprise nucleic acids representing from about 0.01% of the genes of an organism's genome to about 100% of the genes of an organism's genome. For example, about 0.01% of the genes of an organism's genome to about 100% of the genes of an organism's genome can be sequenced using a target complimentary region comprising a plurality of multimers by capturing the genes containing a complimentary sequence from the sample. In some embodiments, the barcoded targets comprise nucleic acids representing from about 0.01% of the transcripts of an organism's transcriptome to about 100% of the transcripts of an organism's transcriptome. For example, about 0.501% of the transcripts of an organism's transcriptome to about 100% of the transcripts of an organism's transcriptome can be sequenced using a target complimentary region comprising a poly(T) tail by capturing the mRNAs from the sample.

Determining the sequences of the spatial labels and the molecular labels of the plurality of the barcodes (e.g., stochastic barcodes) can include sequencing 0.00001%, 0.0001%, 0.001%, 0.01%, 0.1%, 1%, 2%, 3%, 4%, 5%, 6%, 7%, 8%, 9%, 10%, 20%, 30%, 40%, 50%, 60%, 70%, 80%, 90%, 99%, 100%, or a number or a range between any two of these values, of the plurality of barcodes. Determining the sequences of the labels of the plurality of barcodes, for example the sample labels, the spatial labels, and the molecular labels, can include sequencing 1, 10, 20, 30, 40, 50, 60, 70, 80, 90, 100, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or a number or a range between any two of these values, of the plurality of barcodes. Sequencing some or all of the plurality of barcodes can include generating sequences with read lengths of, of about, of at least, or of at most, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values, of nucleotides or bases.

Sequencing can comprise sequencing at least or at least about 10, 20, 30, 40, 50, 60, 70, 80, 90, 100 or more nucleotides or base pairs of the barcoded targets. For example, sequencing can comprise generating sequencing data with sequences with read lengths of 50, 75, or 100, or more nucleotides by performing polymerase chain reaction (PCR) amplification on the plurality of barcoded targets. Sequencing can comprise sequencing at least or at least about 200, 300, 400, 500, 600, 700, 800, 900, 1,000 or more nucleotides or base pairs of the barcoded targets. Sequencing can comprise sequencing at least or at least about 1500, 2000, 3000, 4000, 5000, 6000, 7000, 8000, 9000, or 10000 or more nucleotides or base pairs of the barcoded targets.

Sequencing can comprise at least about 200, 300, 400, 500, 600, 700, 800, 900, 1,000 or more sequencing reads per run. In some embodiments, sequencing comprises sequencing at least or at least about 1500, 2000, 3000, 4000, 5000, 6000, 7000, 8000, 9000, or 10000 or more sequencing reads per run. Sequencing can comprise less than or equal to about 1,600,000,000 sequencing reads per run. Sequencing can comprise less than or equal to about 200,000,000 reads per run.

Samples

In some embodiments, the plurality of targets can be comprised in one or more samples. A sample can comprise one or more cells, or nucleic acids from one or more cells. A sample can be a single cell or nucleic acids from a single cell. The one or more cells can be of one or more cell types. At least one of the one or more cell types can be brain cell, heart cell, cancer cell, circulating tumor cell, organ cell, epithelial cell, metastatic cell, benign cell, primary cell, circulatory cell, or any combination thereof.

A sample for use in the method of the disclosure can comprise one or more cells. A sample can refer to one or more cells. In some embodiments, the plurality of cells can include one or more cell types. At least one of the one or more cell types can be brain cell, heart cell, cancer cell, circulating tumor cell, organ cell, epithelial cell, metastatic cell, benign cell, primary cell, circulatory cell, or any combination thereof. In some embodiments, the cells are cancer cells excised from a cancerous tissue, for example, breast cancer, lung cancer, colon cancer, prostate cancer, ovarian cancer, pancreatic cancer, brain cancer, melanoma and non-melanoma skin cancers, and the like. In some embodiments, the cells are derived from a cancer but collected from a bodily fluid (e.g. circulating tumor cells). Non-limiting examples of cancers can include, adenoma, adenocarcinoma, squamous cell carcinoma, basal cell carcinoma, small cell carcinoma, large cell undifferentiated carcinoma, chondrosarcoma, and fibrosarcoma. The sample can include a tissue, a cell monolayer, fixed cells, a tissue section, or any combination thereof. The sample can include a biological sample, a clinical sample, an environmental sample, a biological fluid, a tissue, or a cell from a subject. The sample can be obtained from a human, a mammal, a dog, a rat, a mouse, a fish, a fly, a worm, a plant, a fungus, a bacterium, a virus, a vertebrate, or an invertebrate.

In some embodiments, the cells are cells that have been infected with virus and contain viral oligonucleotides. In some embodiments, the viral infection can be caused by a virus such as single-stranded (+ strand or "sense") DNA viruses (e.g. parvoviruses), or double-stranded RNA viruses (e.g. reoviruses). In some embodiments, the cells are bacteria. These can include either gram-positive or gram-negative bacteria. In some embodiments, the cells are fungi. In some embodiments, the cells are protozoans or other parasites.

As used herein, the term "cell" can refer to one or more cells. In some embodiments, the cells are normal cells, for example, human cells in different stages of development, or human cells from different organs or tissue types. In some embodiments, the cells are non-human cells, for example, other types of mammalian cells (e.g. mouse, rat, pig, dog, cow, or horse). In some embodiments, the cells are other types of animal or plant cells. In other embodiments, the cells can be any prokaryotic or eukaryotic cells.

In some embodiments the cells are sorted prior to associating a cell with a bead. For example the cells can be sorted by fluorescence-activated cell sorting or magnetic-activated cell sorting, or more generally by flow cytometry. The cells can be filtered by size. In some embodiments a retentate contains the cells to be associated with the bead. In some embodiments the flow through contains the cells to be associated with the bead.

A sample can refer to a plurality of cells. The sample can refer to a monolayer of cells. The sample can refer to a thin section (e.g., tissue thin section). The sample can refer to a solid or semi-solid collection of cells that can be place in one dimension on an array.

Execution Environment

Figure 9:
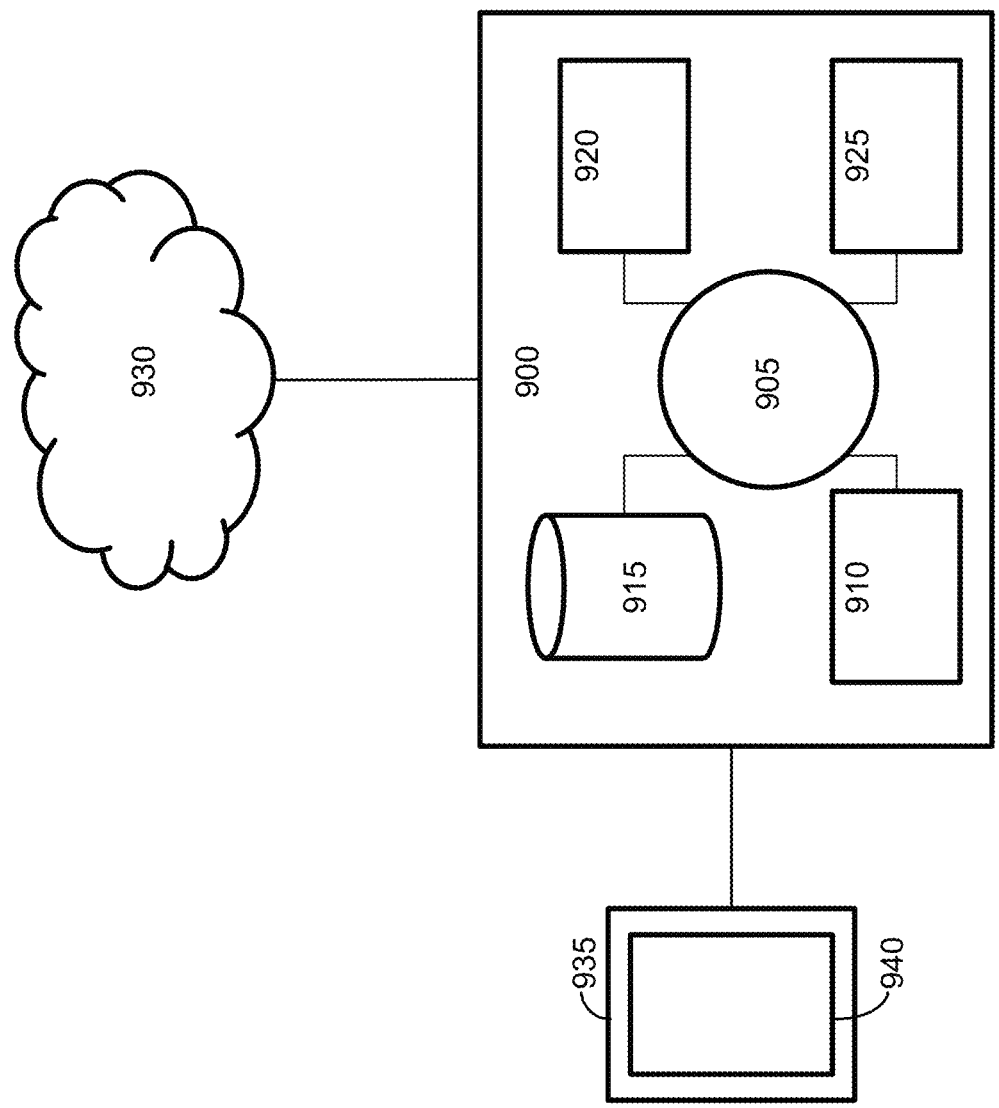
FIG. 9 is a block diagram of an illustrative computing system configured to implement methods of the disclosure.

The present disclosure provides computer systems that are programmed to implement methods (e.g., the method 400, the method 500, the method 600a, or the method 600b described with reference to FIGS. 4, 5, 6A, and 6B) of the disclosure. FIG. 9 shows a computer system 900 that is programmed or otherwise configured to implement any of the methods disclosed herein. The computer system 900 can be an electronic device of a user or a computer system that is remotely located with respect to the electronic device. The electronic device can be a mobile electronic device.

The computer system 900 includes a central processing unit (CPU, also "processor" and "computer processor" herein) 905, which can be a single core or multi core processor, or a plurality of processors for parallel processing. The computer system 900 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 900 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include one or more computer servers, which can enable distributed computing, such as cloud computing. The network 930, in some cases with the aid of the computer system 900, can implement a peer-to-peer network, which may enable devices coupled to the computer system 900 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and writeback. The CPU 905 can be part of a circuit, such as an integrated circuit. One or more other components of the system 900 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 900 in some cases can include one or more additional data storage units that are external to the computer system 900, such as located on a remote server that is in communication with the computer system 900 through an intranet or the Internet.

The computer system 900 can communicate with one or more remote computer systems through the network 930. For instance, the computer system 900 can communicate with a remote computer system of a user (e.g., a microbiologist). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 900 via the network 930.

The computer system 900 can include or be in communication with an electronic display 935 that comprises a user interface (UI) 940 for providing, for example, an output indicative of string co-occurrence or interactions of a plurality of taxa of microorganisms, as represented by strings. Examples of UI's include, without limitation, a graphical user interface (GUI) and web-based user interface.

Methods as described herein can be implemented by way of machine (e.g., computer processor) executable code stored on an electronic storage location of the computer system 900, such as, for example, on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 900, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

In some embodiments, some or all of the analysis functionality of the computer system 900 can be packaged in a single software package. In some embodiments, the complete set of data analysis capabilities can comprise a suite of software packages. In some embodiments, the data analysis software can be a standalone package that is made available to users independently of an assay instrument system. In some embodiments, the software can be web-based, and can allow users to share data. In some embodiments, commercially-available software can be used to perform all or a portion of the data analysis, for example, the Seven Bridges (https://www.sbgenomics.com/) software can be used to compile tables of the number of copies of one or more genes occurring in each cell for the entire collection of cells.

Methods and systems of the present disclosure can be implemented by way of one or more algorithms or methods. A method can be implemented by way of software upon execution by the central processing unit 905. Exemplary applications of algorithms or methods implemented by way of software include bioinformatics methods for sequence read processing (e.g., merging, filtering, trimming, clustering), alignment and calling, and processing of string data and optical density data (e.g., most probable number and cultivable abundance determinations).

In an exemplary embodiment, the computer system 900 can perform data analysis of the sequence datasets generated by performing single cell, stochastic barcoding assays. Examples of data analysis functionality include, but are not limited to, (i) algorithms for decoding/demultiplexing of the sample label, cell label, spatial label, and molecular label, and target sequence data provided by sequencing the stochastic barcode library created in running the assay, (ii) algorithms for determining the number of reads per gene per cell, and the number of unique transcript molecules per gene per cell, based on the data, and creating summary tables, (iii) statistical analysis of the sequence data, e.g., for clustering of cells by gene expression data, or for predicting confidence intervals for determinations of the number of transcript molecules per gene per cell, etc., (iv) algorithms for identifying sub-populations of rare cells, for example, using principal component analysis, hierarchical clustering, k-mean clustering, self-organizing maps, neural networks etc., (v) sequence alignment capabilities for alignment of gene sequence data with known reference sequences and detection of mutation, polymorphic markers and splice variants, and (vi) automated clustering of molecular labels to compensate for amplification or sequencing errors. In some embodiments, the computer system 900 can output the sequencing results in useful graphical formats, e.g., heatmaps that indicate the number of copies of one or more genes occurring in each cell of a collection of cells. In some embodiments, the computer system 900 can execute algorithms for extracting biological meaning from the sequencing results, for example, by correlating the number of copies of one or more genes occurring in each cell of a collection of cells with a type of cell, a type of rare cell, or a cell derived from a subject having a specific disease or condition. In some embodiment, the computer system 900 can execute algorithms for comparing populations of cells across different biological samples.

EXAMPLES

Some aspects of the embodiments discussed above are disclosed in further detail in the following examples, which are not in any way intended to limit the scope of the present disclosure.

Example 1

Separation of Signal Cell Labels and Noise Cell Labels—Second Derivatives

This example describes separating signal cell labels (also referred to as true cell labels) and noise cell labels based on the number of reads (or molecules) associated with the cell labels.

In some instances, noise cell labels may have fewer reads (or molecules) associated with them than signal cell labels. For example, noise cell labels can be caused by cells paired with no bead being lysed and their nucleic acid contents diffusing and associating with beads not paired with any cells. This type of noise cell labels can contain a portion of total nucleic acid contents of a cell. Thus, molecules from the same cell can appear to be from two different cells (e.g., as if they were from two different beads because the cell label has mutated).

As another example, noise cell labels can be caused by mutations during the manufacturing process of the beads. Also, noise cell labels can be caused by insufficient exonuclease treatment (e.g., at steps 216 shown in FIG. 2) such that single stranded DNA on the bead can hybridize and form PCR chimeras during the PCR process. These two types of noise cell labels can occur randomly and rarely.

Figure 10:
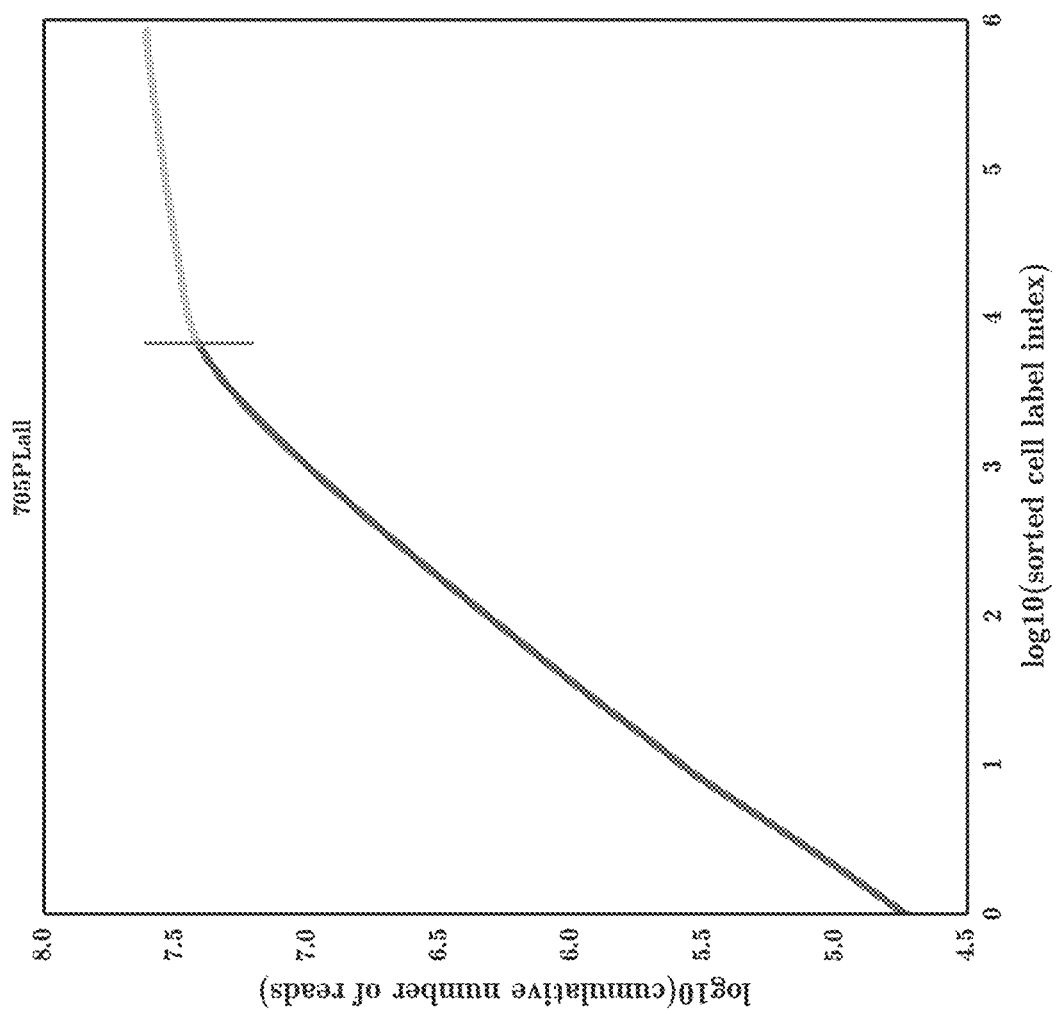
FIG. 10 shows a non-limiting exemplary cumulative sum plot.
Figure 11:
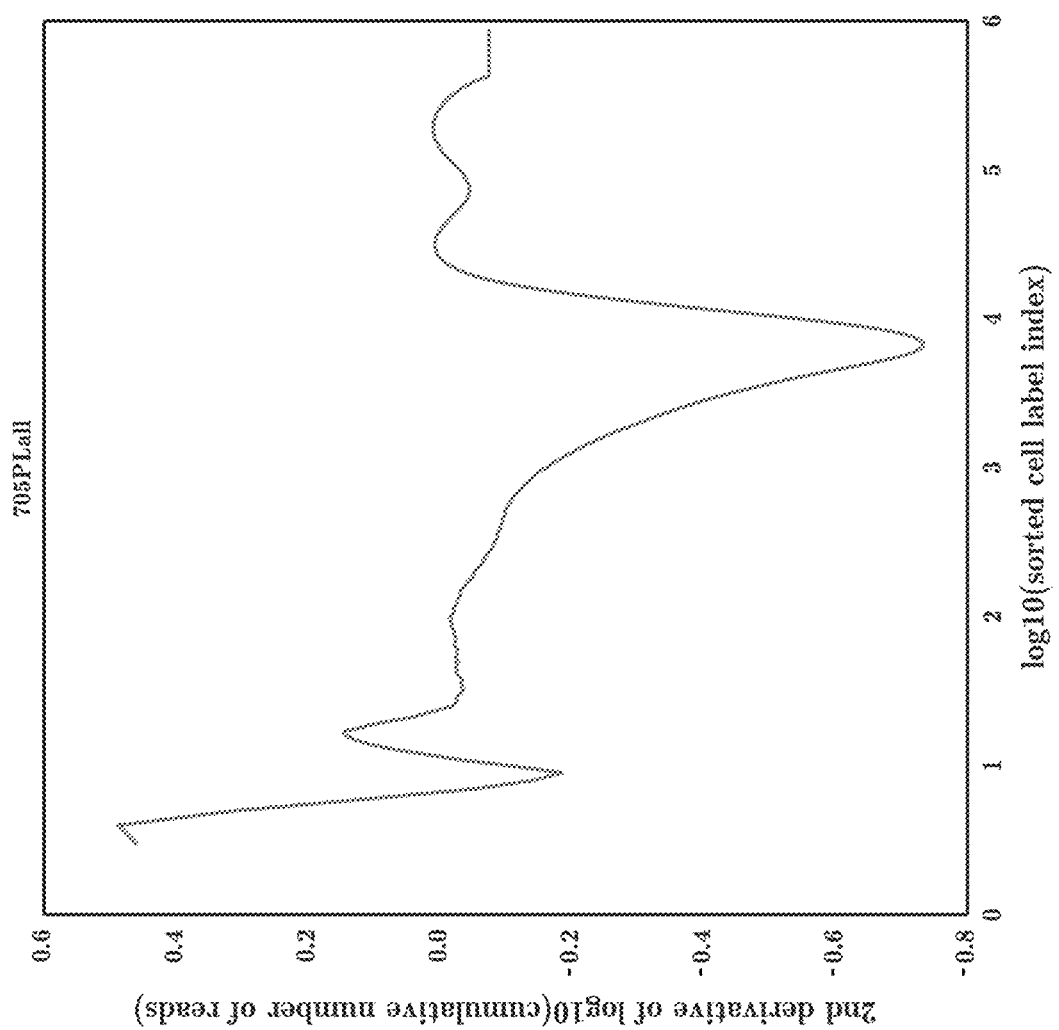
FIG. 11 shows a non-limiting second derivative plot of the cumulative sum plot in FIG. 10.

FIG. 10 shows a non-limiting exemplary cumulative sum plot. Cumulative number of reads versus sorted cell label index on log-log scale. The red line shows the cutoff between true cell labels and noise cell labels. In FIG. 10, a sudden slope change in the cumulative number of reads (or molecules) was observed when sorting all cell labels based on number of reads. To find the cutoff between true cell labels and noise cell labels, the second derivatives of the log-log plot were calculated. FIG. 11 shows a non-limiting second derivative plot of the cumulative sum plot in FIG. 10. Second derivatives of log 10-transformed cumulative number of reads versus log 10-transformed sorted cell label index. The global minimum was inferred as the cutoff between true cell labels and noise cell labels.

In some embodiments, the cell number inferred may not agree with the cell number input and cell number observed in the image analysis. Instead, the cutoff determined using FIG. 11 might either reflect the separation between signal cells of high and low expressing levels, or the separation between different types of noise labels. To correctly infer cell number in these cases, a constraint of percentage of reads (or molecules) in signal cell labels is set in the range of 45% to 92%, based on the empirical data. The number of cells observed from image analysis can be set as a constraint optionally when this value is available.

Altogether, these data demonstrate identifying true cell labels (also referred to as signal cell labels) and noise cell labels can be achieved by determining a minimum of a second derivative plot which corresponds to a cell label threshold for distinguishing true cell labels and noise cell labels.

Example 2

Separation of Signal Cell Labels and Noise Cell Labels—Clustering

This example describes separating signal cell labels (also referred to as true cell labels) and noise cell labels based on their expression patterns (also referred to as feature vectors).

In some embodiments, samples for stochastic barcoding experiments can contain cell types with wide range of expression levels. In such experiments, some cell types could have very similar number of molecules to noise cell labels. To separate true cell labels from noise cell labels when numbers of molecules associated are indistinguishable, clustering techniques can be used to classify noise cell labels and each cell type with low expression level. The method can be based on the assumption that cell labels within the same cell type would have more similar expression patterns than cell labels between different cell types, and noise cell labels would also have more similar feature vectors to each other than to true cell labels.

Figure 12:
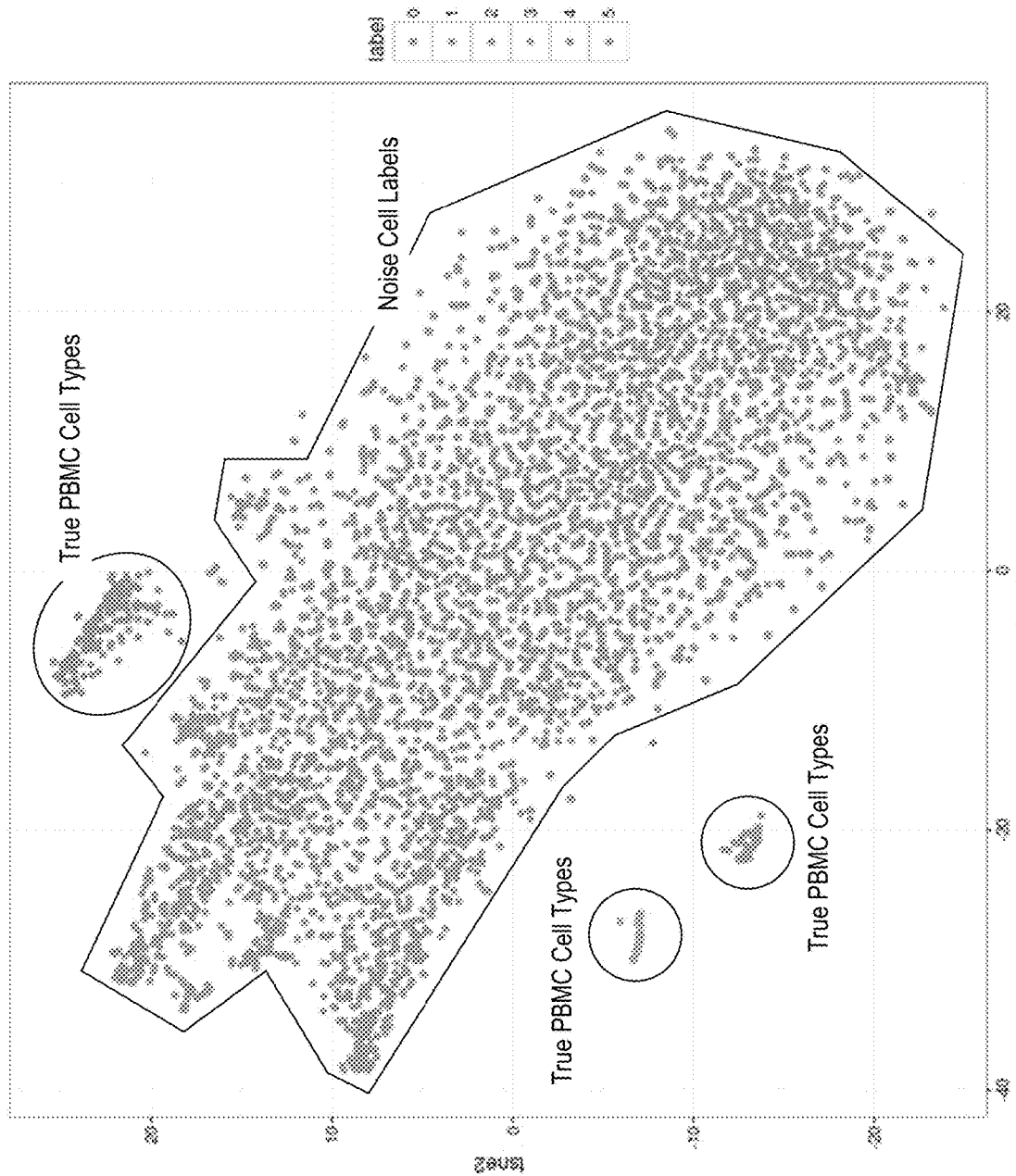
FIG. 12 shows a non-limiting tSNE plot of signal or noise cell labels.

FIG. 12 shows a non-limiting tSNE plot of signal or noise cell labels. PBMC cell were stochastically barcoded. The 5450 cell labels in FIG. 12 contained 240 true cell labels with low expression levels and 5210 noise cell labels. In particular, the classification was done by first projecting the expression vectors into a two dimensional (2D) space using a t-distributed stochastic neighbor embedding (tSNE), and clustering the 2D coordinates by a density-based spatial clustering of applications with noise (DBScan) method. With the knowledge that most of the 5450 cell labels are noise cell labels, the dominant cluster was concluded to be noise label cluster, and the other three compact clusters were concluded to be true cell labels of three different cell types.

Altogether, these data demonstrate that identifying true cell labels and noise cell labels can be achieved by clustering of expression patterns associated with the cell labels.

Example 3

Identification of True Cells and Noise Cell Labels—Second Derivatives

This example describes separating true cells (also referred to as signal cell labels or true cell labels) and noise (also referred to as noise cells or noise cell labels) based on the number of reads (or molecules) associated with the cells (or cell labels).

Example Dataset 1.

Figure 13B:
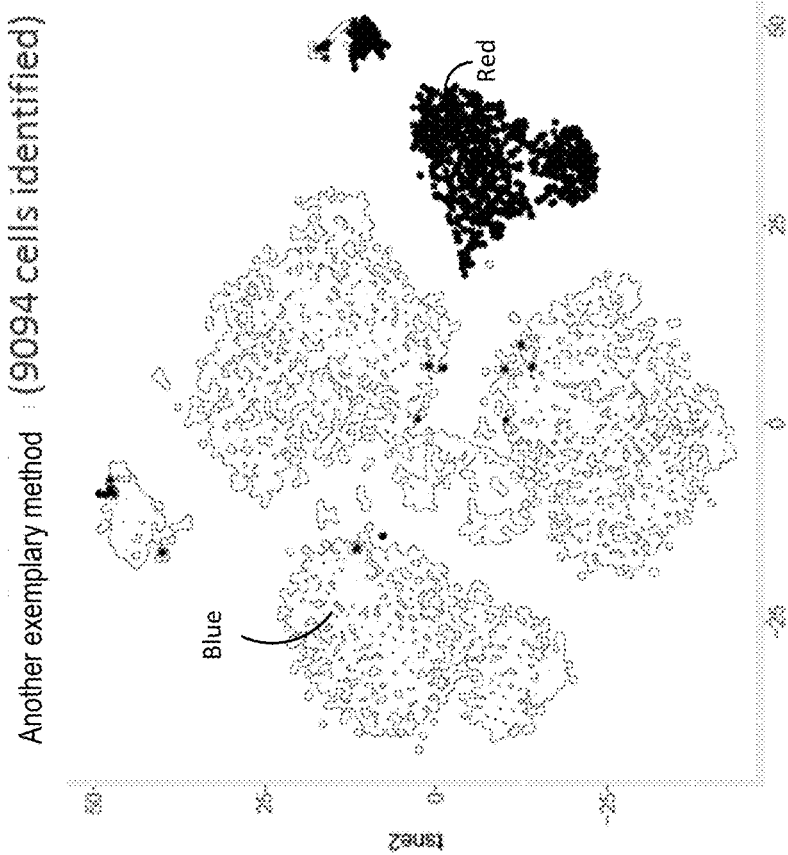
FIGS. 13A-13B are non-limiting exemplary plots illustrating comparison of cells identified by the method 400 illustrated with reference to FIG. 4 (FIG. 13A) and the method 600a illustrated with reference to FIG. 6A (FIG. 13B) for a sample processed using the BD™ Breast Cancer gene panel with three distinct breast cancer cell lines and donor isolated PBMCs. The dots labeled as blue in both
Figure 13A:
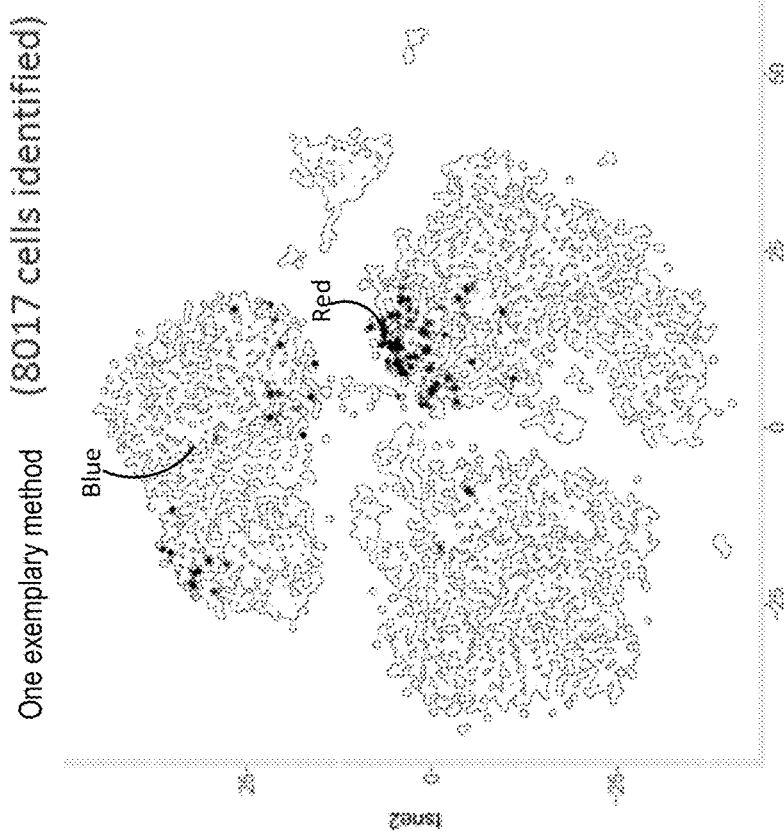
Figure 14B:
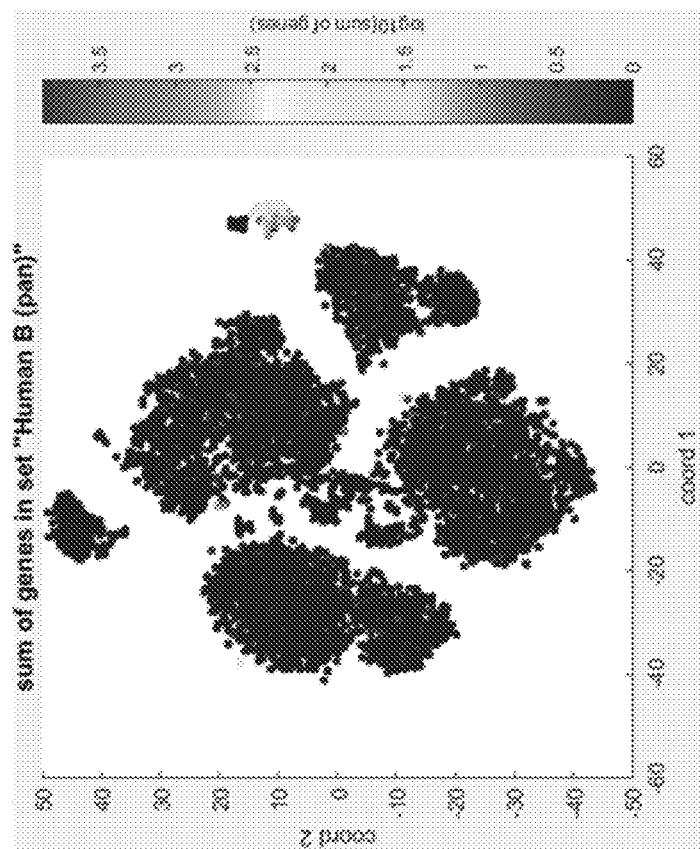
FIGS. 14B-14D show that the additional cells identified by the method 600a are indeed true cells.
Figure 14A:
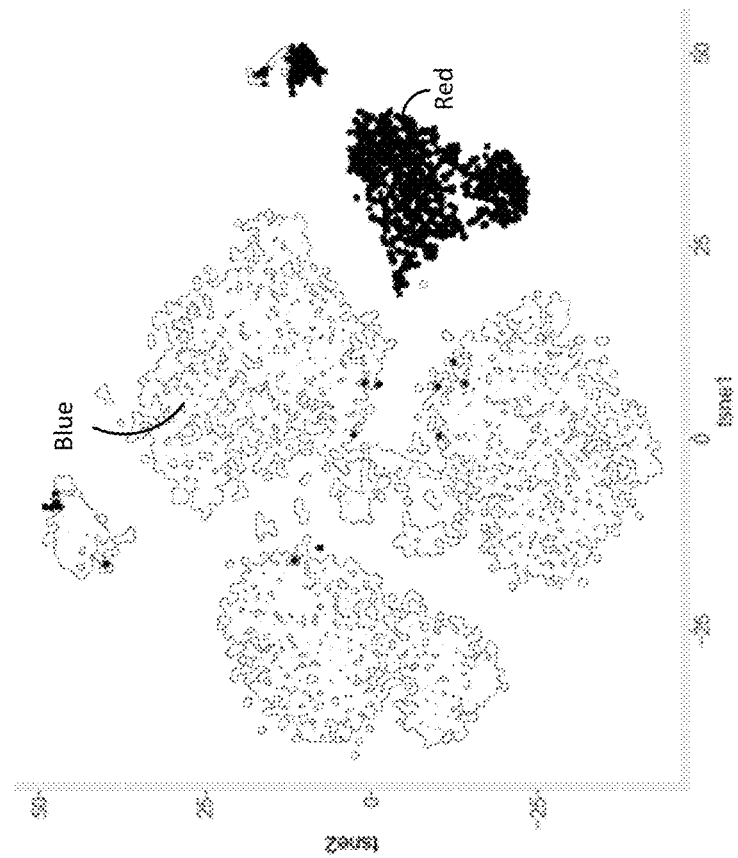
FIG. 14A is non-limiting exemplary plot showing the cells identified by the method 600a, where the cells labeled red are the additional cells identified (compared to the cells identified by method 400 illustrated with reference to FIG. 4). The cells are colored by expression of PBMCs, such as B cells (FIG. 14B), NK cells (FIG. 14C), and T cells (FIG. 14D).
Figure 14:
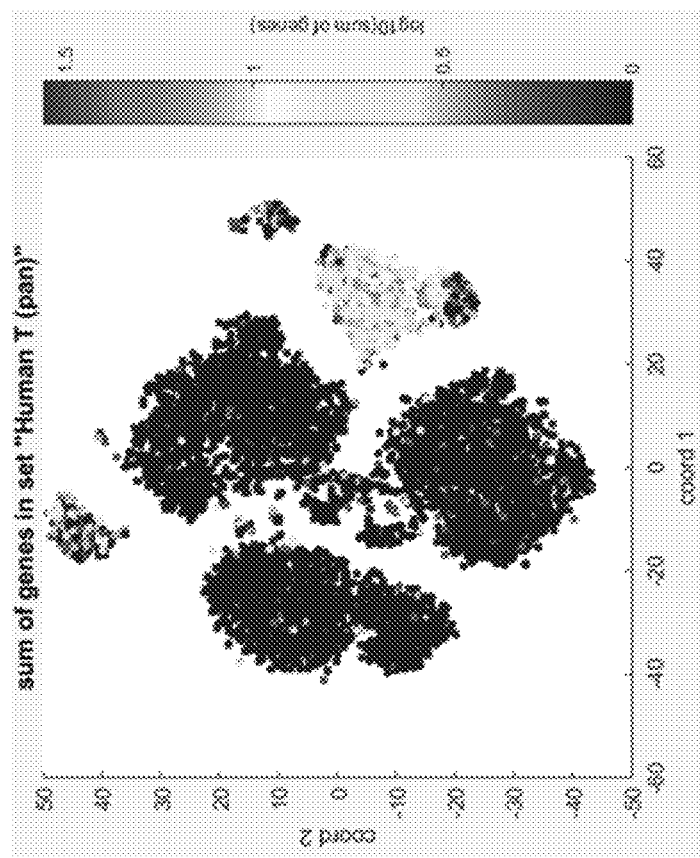
Figure 14:
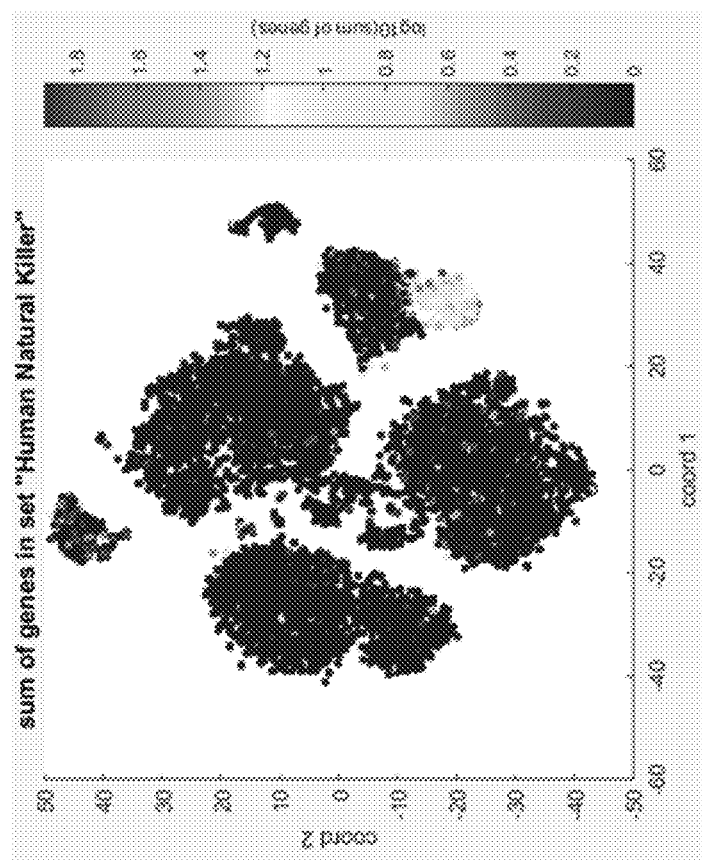

This dataset was processed using the BD™ Breast Cancer gene panel (BrCa400) with three distinct breast cancer cell lines and donor isolated PBMCs (Peripheral Blood Mononuclear Cells). The method 400b, described with reference to FIG. 4, identified 8017 cells, among which 186 cells were identified as noise cells by the method 600a, described with reference to FIG. 6. The method 600a detected additional 1263 cells, which were confirmed to be mostly PBMCs, see FIGS. 13A-13B, 14A-14D. FIGS. 13A-13B are non-limiting exemplary plots illustrating comparison of cells identified by the method 400 illustrated with reference to FIG. 4 (FIG. 13A) and the method 600a illustrated with reference to FIG. 6A (FIG. 13B) for a sample processed using the BD™ Breast Cancer gene panel with three distinct breast cancer cell lines and donor isolated PBMCs. The dots labeled as blue in both FIGS. 13A-13B are the common cells detected by both methods. The dots labeled as red in FIG. 13A are the cells identified as noise by method 600a. The dots labeled as red in FIG. 13B are the additional true cells identified by method 600a. FIG. 14A is non-limiting exemplary plot showing the cells identified by the method 600a, where the cells labeled red are the additional cells identified (compared to the cells identified by method 400 illustrated with reference to FIG. 4). The cells are colored by expression of PBMCs, such as B cells (FIG. 14B), NK cells (FIG. 14C), and T cells (FIG. 14D). FIGS. 14B-14D show that the additional cells identified by the method 600a are indeed true cells.

Example Dataset 2.

Figure 15A:
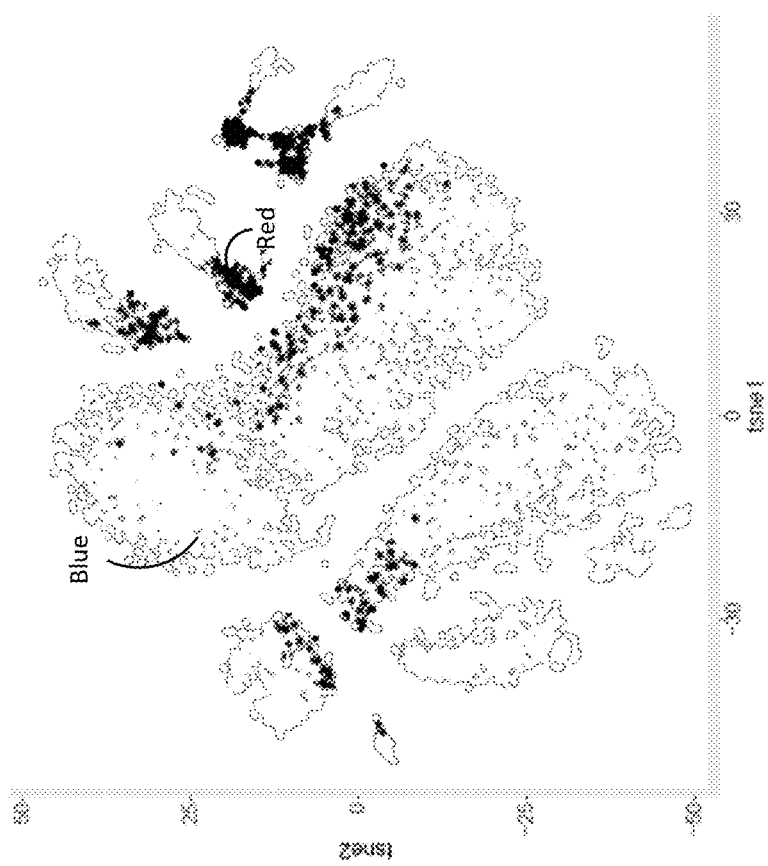
FIGS. 15A-15B are non-limiting exemplary plots illustrating comparison of cells identified by the method 400 illustrated with reference to FIG. 4 (FIG. 15A) and the method 600a illustrated with reference to FIG. 6A (FIG. 15B) for a sample processed using the BD™ Blood gene panel with a healthy donor isolated PBMCs. The dots labeled as blue in both
Figure 15B:
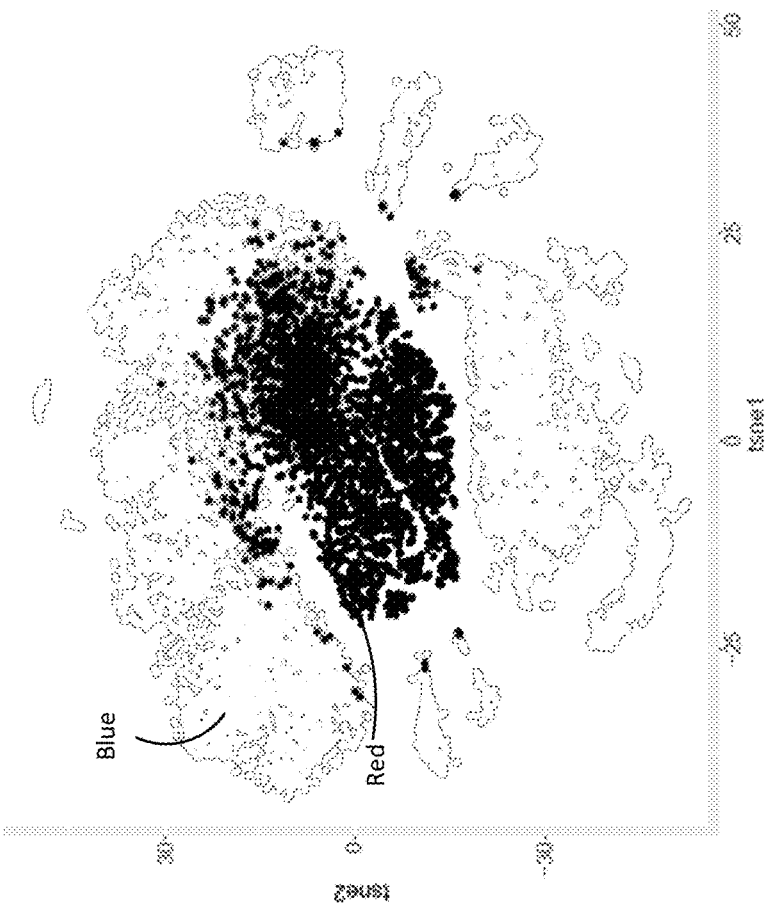
Figure 16B:
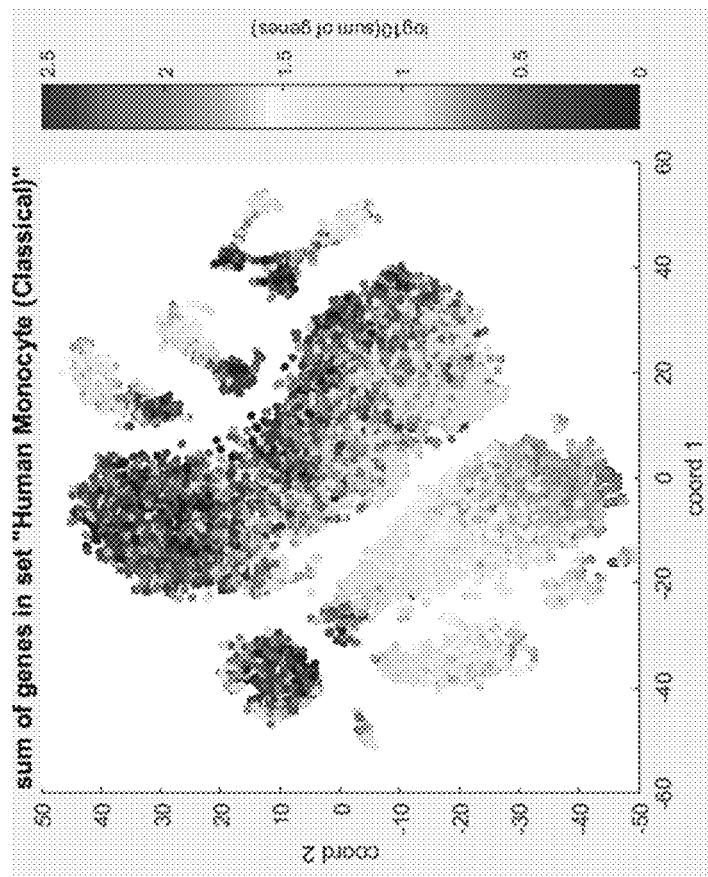
FIG. 16A-16B are non-limiting exemplary plots showing the cells identified by the method 400.
Figure 16A:
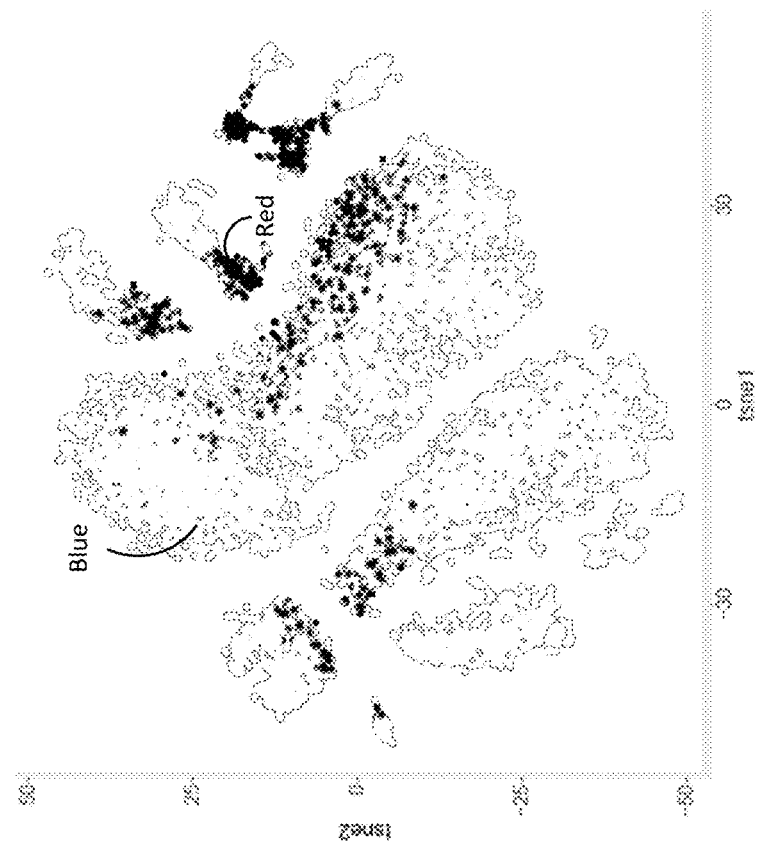
Figure 17B:
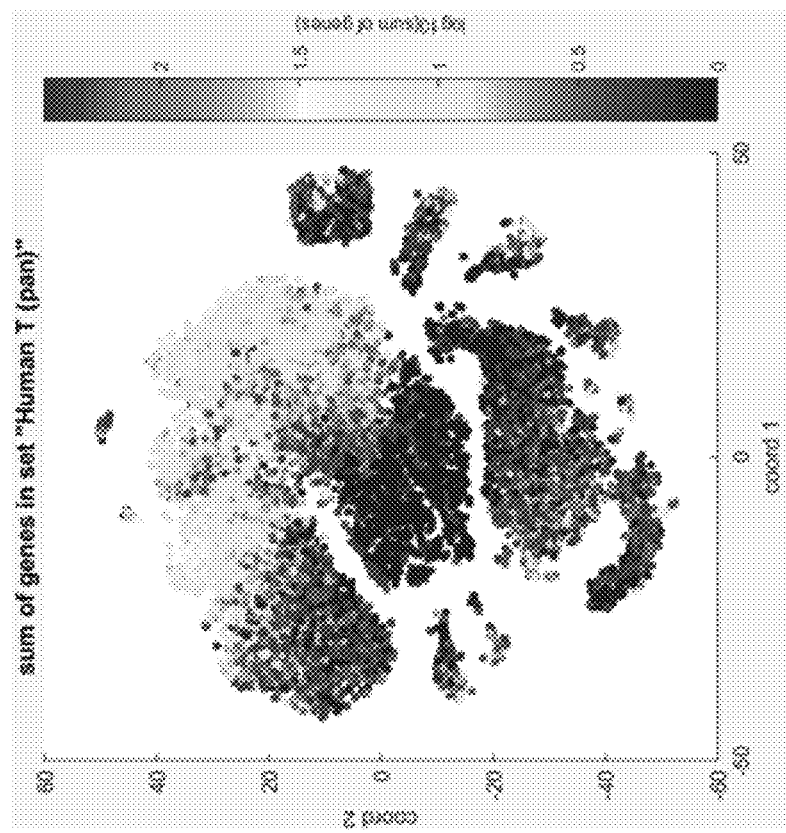
FIG. 17A is a non-limiting exemplary plot showing the cells identified by the method 600a, where the cells labeled as are the additional cells identified. The cells are colored by expression of T cells (FIG. 17B), expression of important genes LAT (FIG. 17C) and IL7R (FIG. 17D).
Figure 17A:
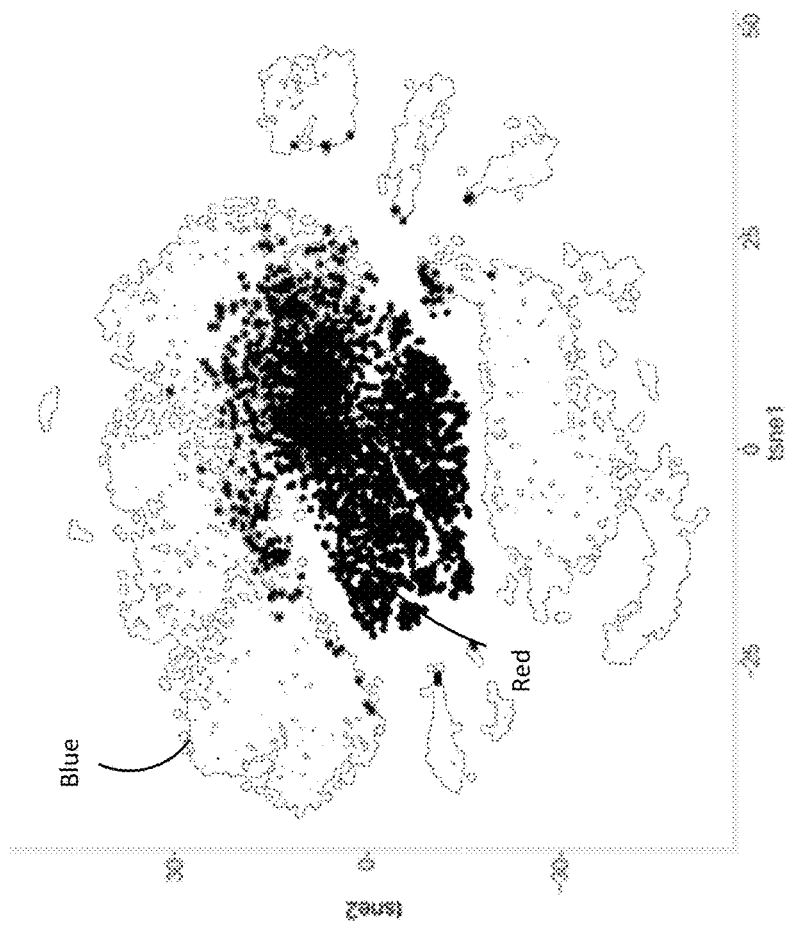
Figure 17:
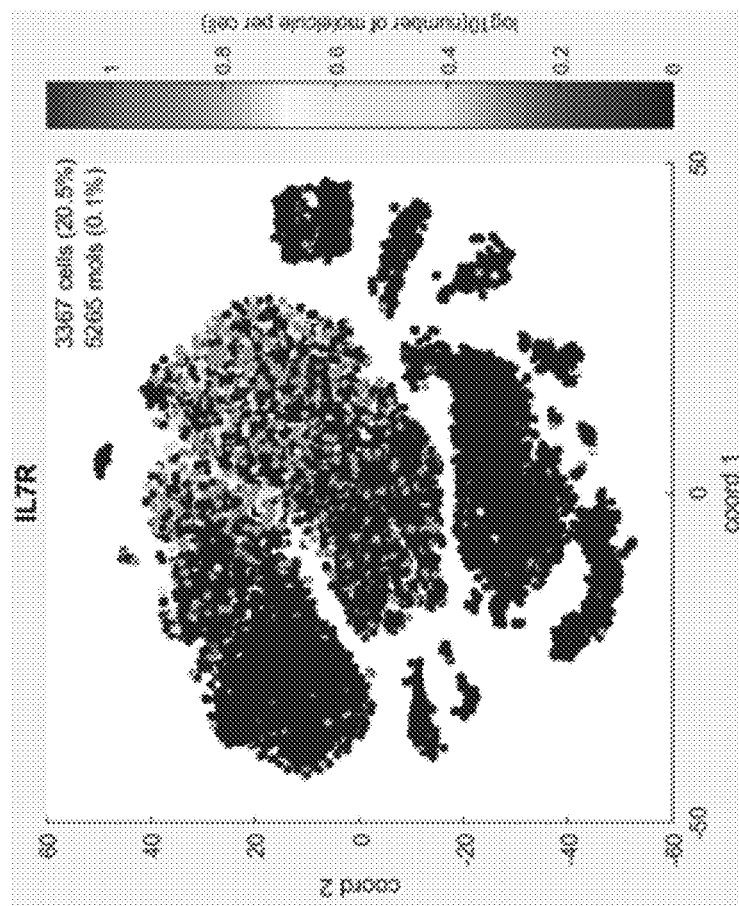
Figure 17:
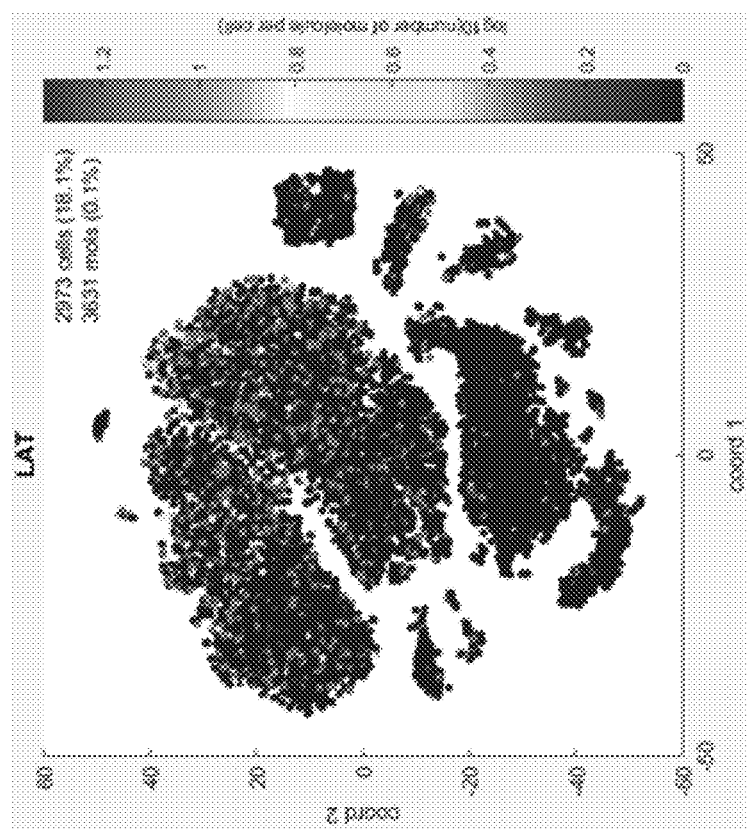

This dataset was processed using the BD™ Blood gene panel (Blood500) with a healthy donor isolated PBMCs. The method 400b, described with reference to FIG. 4, identified 13,950 cells, among which 1,333 cells were identified as noise cells by the method 600a, described with reference to FIG. 6. The method 600a detected additional 3,842 cells, which were confirmed to be mostly T cells, as well as expressed in important genes such as LAT (Linker for Activation of T cells) and IL7R (Interleukin 7 Receptor), see FIGS. 15A-15B, 16A-16B, and 17A-17D. FIG. 15A-15B are non-limiting exemplary plots illustrating comparison of cells identified by the method 400 illustrated with reference to FIG. 4 (FIG. 15A) and the method 600a illustrated with reference to FIG. 6A (FIG. 15B) for a sample processed using the BD™ Blood gene panel with a healthy donor isolated PBMCs. The dots labeled as blue in both FIGS. 15A-15B are the common cells detected by both methods. The dots labeled as red in FIG. 15A are the cells identified as noise by the method 600a. The dots labeled as red in FIG. 15B are the additional cells identified by the method 600a. FIG. 16A-16B are non-limiting exemplary plots showing the cells identified by the method 400. In FIG. 16A, the cells labeled red are the cells identified as noise by the method 600a. In FIG. 16B, the cells are colored by expression of a group of Monocyte marker genes, such as CD14 and S100A6. The "noise" cells identified by the improved algorithm were mostly low expressers of the Monocytes. FIG. 17A is a non-limiting exemplary plot showing the cells identified by the method 600a, where the cells labeled red are the additional cells identified. The cells are colored by expression of T cells (FIG. 17B), expression of important genes LAT (FIG. 17C) and IL7R (FIG. 17D).

Altogether, the data that different embodiments of the method of identifying signal cell labels or true cells have different performance and may be complementary to one another.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of identifying cell types in a biological sample, comprising:
    (a) obtaining sequencing data comprising a plurality of nucleic acid sequences, each nucleic acid sequence comprising:
        a stochastic barcode comprising a cell label and a molecular label; and
        a target sequence,
        wherein the plurality of nucleic acid sequences comprises target sequences from a plurality of stochastically barcoded nucleic acid targets of a plurality of cells of a biological sample,
        wherein stochastically barcoded nucleic acid targets from a single cell of the plurality of cells are associated with the same cell label in the sequencing data, and stochastically barcoded nucleic acid targets from different single cells of the plurality of cells are associated with different cell labels,
        and wherein the number of distinct cell labels in the sequencing data is greater than the number of cells in the plurality of cells;
    (b) determining a rank of each of the cell labels of the plurality of nucleic acid sequences based on the number of molecular labels with distinct sequences associated with each of the cell labels,
        and further determining a cumulative sum for each rank of the cell labels, wherein the cumulative sum for the rank comprises a summation of a number of molecular labels with distinct sequences associated with each of the cell labels with a lower rank;
    (c) determining a cell label threshold based on the number of molecular labels with distinct sequences associated with each of the cell labels and the rank of each of the cell labels determined in (b);

(d) identifying at least one cell label as a noise cell label based on the number of molecular labels with distinct sequences associated with each of the cell labels and the cell label threshold determined in (c), wherein the number of molecular labels with distinct sequences associated with each of the at least one cell label identified as a noise cell label is not greater than the cell label threshold;

(e) generating noise-reduced sequencing data by, for each of the at least one cell label identified as a noise cell label in (d), removing from the sequencing data nucleic acid sequences associated with the identified cell label;

(f) estimating the number of the nucleic acid targets in single cells of the plurality of cells based on the number of molecular labels with distinct sequences and the cell label associated with the nucleic acid target in the noise-reduced sequencing data, thereby estimating the expression level of one or more genes in single cells of the plurality of cells in the sample; and (g) identifying a cell type of each of the plurality of cells by correlating the expression level of one or more genes estimated in (f) with the cell type.

2. The method of claim 1, wherein estimating the number of the nucleic acid targets comprises removing sequencing information associated with non-unique molecular labels associated with each of the cell labels from the sequencing data.

3. The method of claim 1, wherein determining the cell label threshold in (c) comprises:
determining a rank n of the cell labels with the largest change in a cumulative sum for the rank n and a cumulative sum for the next rank n+1, wherein the rank n of the cell labels with the largest change in the cumulative sum and the cumulative sum for the next rank n+1 corresponds to the cell label threshold.

4. The method of claim 1, wherein determining the cell label threshold in (c) comprises:
determining the cell label with the largest change in a cumulative sum for the cell label with a rank n and a cumulative sum for the cell label with the next rank n+1, wherein a number of molecular labels with distinct sequences associated with the cell label corresponds to the cell label threshold.

5. The method of claim 1, wherein determining the cell label threshold in (c) comprises:
generating a cumulative sum plot based on the cumulative sum for each rank of the cell labels;
generating a second derivative plot of the cumulative sum plot; and
determining a minimum of the second derivative plot of the cumulative sum plot, wherein the minimum of the second derivative plot corresponds to the cell label threshold.

6. The method of claim 5, wherein generating the second derivative plot of the cumulative sum plot comprises determining a difference between a cumulative sum of a first rank of the cell labels and a cumulative sum of a second rank of the cell labels over a difference between the first rank and the second rank.

7. The method of claim 6, wherein the difference between the first rank and the second rank is one.

8. The method of claim 5, wherein the cumulative sum plot is a log-log plot.

9. The method of claim 8, wherein the log-log plot is a $\log_{10}$-$\log_{10}$ plot.

10. The method of claim 5, wherein the minimum is a global minimum.

11. The method of claim 5, wherein determining the minimum of the second derivative plot comprises determining a minimum of the second derivative plot above a threshold of a minimum number of molecular labels associated with each of the cell labels.

12. The method of claim 11, wherein the threshold of the minimum number of molecular labels associated with each of the cell labels is a percentile threshold.

13. The method of claim 11, wherein the threshold of the minimum number of molecular labels associated with each of the cell labels is determined based on the number of cells in the plurality of cells.

14. The method of claim 5, wherein determining the minimum of the second derivative plot comprises determining a minimum of the second derivative plot below a threshold of a maximum number of molecular labels associated with each of the cell labels.

15. The method of claim 14, wherein the threshold of the maximum number of molecular labels associated with each of the cell labels is a percentile threshold.

16. The method of claim 14, wherein the threshold of the maximum number of molecular labels associated with each of the cell labels is determined based on the number of cells in the plurality of cells.

17. The method of claim 1, wherein each of the cell labels is identified as a signal cell label if the number of molecular labels with distinct sequences associated with the each of the cell labels determined is greater than the cell label threshold.

18. The method of claim 1, comprising:
for one or more of the plurality of nucleic acid targets:
(1) counting the number of molecular labels with distinct sequences associated with the nucleic acid target in the noise-reduced sequencing data; and
(2) estimating the number of the nucleic acid target based on the number of molecular labels with distinct sequences associated with the nucleic acid target in the noise-reduced sequencing data counted in (1).

19. The method of claim 1, further comprising:
(A) re-identifying at least one cell label that is identified as a noise cell label in (d) as a signal cell label; and
for each of the at least one cell label re-identified as a signal cell label, adding back to the noise-reduced sequencing data nucleic acid sequences associated with the cell label re-identified as a signal cell label; and/or
(B) re-identifying at least one cell label in the noise-reduced sequencing data as a noise cell label; and
for each of the at least one cell label re-identified as a noise cell label, removing from the noise-reduced sequencing data nucleic acid sequences associated with the cell label re-identified as a noise cell label.

20. The method of claim 19, wherein re-identifying at least one cell label in the noise-reduced sequencing data as a noise cell label comprises:
determining a plurality of second nucleic acid targets of the nucleic acid targets, each second nucleic acid target having one or more variability indications above a variability threshold; and
re-identifying at least one cell label in the noise-reduced sequencing data as a noise cell label based on (1) the number of molecular labels with distinct sequences associated with the plurality of second nucleic acid targets, and (2) the cell label threshold.

21. The method of claim 19, wherein re-identifying at least one cell label that is identified as a noise cell label in (d) as a signal cell label comprises:
- determining a plurality of third nucleic acid targets of the nucleic acid targets, each third nucleic acid target having an association with the at least one cell label identified as noise cell labels in (d) above an association threshold; and
- re-identifying at least one cell label that is identified as a noise cell label in (e) as a signal cell label, for each of the plurality of cell labels, based on (1) the number of molecular labels with distinct sequences associated with the plurality of third nucleic acid targets, and (2) the cell label threshold.

22. The method of claim 1, further comprising (h) before obtaining sequencing data in (a), stochastically barcoding the plurality of nucleic acid targets in the plurality of cells using the plurality of barcodes to create stochastically barcoded nucleic acid targets, wherein each of the plurality of barcodes comprises the stochastic barcode comprising the cell label and the molecular label.

23. The method of claim 1, wherein the biological sample comprises a clinical sample from a subject having a disease or condition,
- the method further comprising altering a therapeutic regimen for treating the disease or condition based on the identified cell type.

24. The method of claim 22, wherein the biological sample comprises a clinical sample from a subject having a disease or condition,
- the method further comprising:
- treating a second plurality of cells of the biological sample with a drug or therapy; and
- repeating (a)-(h) for the treated second plurality of cells, to thereby determine the biological sample's response to the drug or therapy.

* * * * *